United States Patent
Ahlfors et al.

(10) Patent No.: US 9,562,069 B2
(45) Date of Patent: *Feb. 7, 2017

(54) SELECTIVE CASPASE INHIBITORS AND USES THEREOF

(71) Applicant: Genesis Technologies Limited, Warrens, St. Michael (BB)

(72) Inventors: Jan-Eric Ahlfors, Laval (CA); Khalid Mekouar, Laval (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/307,025

(22) Filed: Jun. 17, 2014

(65) Prior Publication Data

US 2015/0011458 A1    Jan. 8, 2015

Related U.S. Application Data

(63) Continuation of application No. 12/993,565, filed as application No. PCT/CA2009/000696 on May 21, 2009, now Pat. No. 8,791,235.

(60) Provisional application No. 61/128,253, filed on May 21, 2008.

(51) Int. Cl.

| | | |
|---|---|---|
| C07K 5/08 | (2006.01) | |
| C07K 5/10 | (2006.01) | |
| C07K 5/062 | (2006.01) | |
| C07C 271/22 | (2006.01) | |
| C07C 317/50 | (2006.01) | |
| C07D 209/16 | (2006.01) | |
| C07D 213/81 | (2006.01) | |
| C07D 215/12 | (2006.01) | |
| C07D 295/26 | (2006.01) | |
| C07F 9/40 | (2006.01) | |
| C07F 9/6533 | (2006.01) | |
| C07K 5/02 | (2006.01) | |
| C07K 5/087 | (2006.01) | |
| C07K 5/093 | (2006.01) | |
| C07K 14/81 | (2006.01) | |
| C07K 5/083 | (2006.01) | |
| C07K 5/103 | (2006.01) | |
| A61K 38/00 | (2006.01) | |
| C07K 5/065 | (2006.01) | |
| C07K 5/072 | (2006.01) | |
| C07K 5/078 | (2006.01) | |

(52) U.S. Cl.
CPC ......... *C07K 5/06034* (2013.01); *C07C 271/22* (2013.01); *C07C 317/50* (2013.01); *C07D 209/16* (2013.01); *C07D 213/81* (2013.01); *C07D 215/12* (2013.01); *C07D 295/26* (2013.01); *C07F 9/4006* (2013.01); *C07F 9/6533* (2013.01); *C07K 5/0202* (2013.01); *C07K 5/081* (2013.01); *C07K 5/0812* (2013.01); *C07K 5/0819* (2013.01); *C07K 5/1013* (2013.01); *C07K 14/8139* (2013.01); *A61K 38/00* (2013.01); *A61K 38/005* (2013.01); *C07C 2102/08* (2013.01); *C07K 5/06052* (2013.01); *C07K 5/06078* (2013.01); *C07K 5/06104* (2013.01); *C07K 5/06139* (2013.01)

(58) Field of Classification Search
CPC ....................................................... C07K 5/08
USPC ....................................................... 530/331
See application file for complete search history.

(56) References Cited

U.S. PATENT DOCUMENTS

| | | |
|---|---|---|
| 3,341,331 A | 9/1967 | Kimura et al. |
| 3,640,716 A | 2/1972 | Nagae et al. |
| 4,269,936 A | 5/1981 | Arai et al. |
| 5,278,148 A | 1/1994 | Branca et al. |
| 5,976,858 A | 11/1999 | Palmer et al. |
| 6,287,840 B1 | 9/2001 | Palmer et al. |
| 7,256,198 B2 | 8/2007 | Dollings et al. |
| 7,589,066 B2 | 9/2009 | Orlowski et al. |
| 2004/0005650 A1 | 1/2004 | Edris |
| 2008/0220416 A1 | 9/2008 | Miele et al. |
| 2008/0227976 A1 | 9/2008 | Mortimore et al. |
| 2011/0077190 A1 | 3/2011 | Ahlfors et al. |
| 2012/0157394 A1 | 6/2012 | Ahlfors et al. |
| 2014/0038903 A1 | 2/2014 | Ahlfors et al. |

FOREIGN PATENT DOCUMENTS

| | | |
|---|---|---|
| CA | 2589460 A1 | 6/2006 |
| JP | S 4818256 B1 | 6/1973 |
| JP | H 11503417 A | 3/1999 |
| JP | 2002145848 A | 5/2002 |
| WO | WO 97/43305 A1 | 11/1987 |

(Continued)

OTHER PUBLICATIONS

Burguillos, et al. Caspase Signalling Controls Microglia Activation and Neurotoxicity, Nature vol. 472, Apr. 21, 2011, pp. 319-325.

(Continued)

*Primary Examiner* — David Lukton
(74) *Attorney, Agent, or Firm* — Knobbe, Martens, Olson & Bear, LLP

(57) ABSTRACT

The present invention relates to compounds of Formula I, IA, II, IIA, III, or IIIA and their pharmaceutical uses. Particular aspects of the invention relate to the use of those compounds for the selective inhibition of one or more caspases. Also described are methods where the compounds of Formula I, IA, II, IIA, III, or IIIA are used in the prevention and/or treatment of various diseases and conditions in subjects, including caspase-mediated diseases such as sepsis, myocardial infarction, ischemic stroke, spinal cord injury (SCI), traumatic brain injury (TBI) and neurodegenerative disease (e.g. multiple sclerosis (MS) and Alzheimer's, Parkinson's, and Huntington's diseases).

25 Claims, No Drawings

(56) References Cited

FOREIGN PATENT DOCUMENTS

| WO | WO 95/23222 A1 | 8/1995 |
|---|---|---|
| WO | WO 96/30353 A1 | 10/1996 |
| WO | WO 96/30395 A2 | 10/1996 |
| WO | WO 98/42342 A1 | 10/1998 |
| WO | WO 99/31122 A2 | 6/1999 |
| WO | WO 99/48910 A1 | 9/1999 |
| WO | WO 99/57135 A1 | 11/1999 |
| WO | WO 01/42216 A2 | 6/2001 |
| WO | WO 01/90070 A2 | 11/2001 |
| WO | WO 01/94351 A1 | 12/2001 |
| WO | WO 02/22611 A2 | 3/2002 |
| WO | WO 02/42278 A2 | 5/2002 |
| WO | WO 03/016335 A2 | 2/2003 |
| WO | WO 2005/021516 A1 | 3/2005 |
| WO | WO 2006/032457 A1 | 3/2006 |
| WO | WO 2006/082434 A1 | 8/2006 |
| WO | WO 2008/008264 A2 | 1/2008 |
| WO | WO 2009/140765 A1 | 11/2009 |
| WO | WO 2010/133300 A1 | 11/2010 |
| WO | WO 2012/140500 A1 | 10/2012 |

OTHER PUBLICATIONS

Calignon, et al., Caspase Activation Precedes and Leads to Tangles, Nature, vol. 464, Apr. 22, 2010, pp. 1201-1205.
Gdynia, et al., Basal Caspase Activity Promotes Migration and Invasiveness in Glioblastoma Cell, Molecular Cancer Research 2007; 5(12), Dec. 2007, pp. 1232-1240.
Huang, et al., Caspase 3-Meditated Stimulation of Tumor Cell Repopulation During Cancer Radiotherapy, Nature Medicine, vol. 17, No. 7, Jul. 2011, pp. 860-867.
Hyman, Caspase Activation Without Apoptosis: Insight Into AB Initiation of Neurodegeneration, Nature Neuroscience, vol. 14, No. 1, Jan. 2011, pp. 5-6.
Kakinohana, et al. Delayed Paraplegia After Spinal Cord Ischemic Injury Requires Caspase-3 Activation in Mice, Stroke. Aug. 2011: 42 (8): 2302-2307.
LeBlanc, et al. Caspase-6 As a Novel Early Target in the Treatment of Alzheimer's Disease, European Journal of Neuroscience, vol. 37, pp. 2005-2018, 2013.
Li, et al. Caspase-Dependent Retinal Ganglion Cell Apoptosis in the Rat Model of Acute Diabetes, Chin Med. Journal 2008; 121(24):2566-2571, pp. 2566-2571.
Nikolaev, et al. N-App Binds DR6 to Cause Axon Pruning and Neuron Death Via Distinct Caspases, Nature, Feb. 19, 2009; 457(7232): 984-989.
Plant, et al. Absence of Caspase-3 Protects Against Denervation-Induced Skeletal Muscle Atrophy, Journal of Applied Physiology 107: 224-234, 2009.
Radziszewska, et a. Absence of Caspase-3 Protects Pancreatic B-Cells From C-Mycinduced Apoptosis Without Leading to Tumor Formation, The Journal of Biological Chemistry vol. 284, No. 16, pp. 10947-10956, Apr. 17, 2009.
Takagi, et al., Caspase Activation in Neuronal and Glial Apoptosis Following Spinal Cord Injury in Mice, Neurol. Med. Chir. (Tokyo) 43, Jan. 2003, pp. 20-30.
Kam, et al. Design and evaluation of inhibitors for dipeptidyul peptidase I (Cathepsin C), Archives of Biochemistry and Biophysics, 2004, pp. 123-134, vol. 427.
Talanian et al., Substrate Specificities Of Caspase Family Proteases. J. Biol. Chem., vol. 272, No. 15, pp. 9677-9682.
Friedrich-Bochnitschek, et al., Allyl Esters as Carboxy Protecting Groups in the Synthesis of O-Glycopeptide, J. Org. Chem., 1989, 54, 751-756.
Götz, et al., Aza-peptidyl Michael Acceptors. A New Class of Potent and Selective Inhibitors of Asparaginyl Endopeptidases (Legumains) from Evolutionarily Diverse Pathogens.
Isaacs, et al., Structure-based design of novel groups for use in the P1 position of thrombin inhibitor scaffolds. Part 1: Weakly basic azoles, Bioorganic & Medicinal Chemistry Letters, 2006,16, 338-342.

O'Donnell, et al., Serine-threonine protein phosphatase inhibitors derived from nodularin: role of the 2-methyl and 2-diene groups in the Adda residue and the effect of macrocyclic conformational restratint.
Entry from Seikagaku jitenn (a dictionary of biochemistry) (the $3^{rd}$ edition) Tokyo Kgaku Dojin, 2002, Jul. 1, the $5^{th}$ impression, pp. 290-291 (Japanese).
Adessi et al., Converting a Peptide into a Drug: Strategies to Improve Stability and Bioavailability, Current Medicinal Chemistry, vol. 9, No. 9, May 2002, pp. 963-978(16).
Bavikar et al., Pd-catalysed one-pot chemoselective hydrogenation protocol for the preparation of carboxamides directly from azides, Tetrahedron Letters, 51: 3815-3819 (2010).
Beaumont, et al., Design of ester prodrugs to enhance oral absorption of poorly permeable compound: Challenges to the discovery scientist, Curr Drug Metabolism, $:461-85 (2003).
Berdowska, Izabela, Cysteine proteases as disease markers, Clinica Chimica Acta, 342: 41-69 (2004).
Ettmayer et al., Lessons learned from marketed and investigational prodrugs, Med. Chem. 47 (10): 2394-2404 (2004).
Ewing et al., Design and Structure-Activity Relationships of Potent and Selective Inhibitors of Blood Coagulation Factor Za, J. Med. Chem., 42: 3557-3571 (1999).
Gloria et al., Aspartic vinyl sulfones: Inhibitors of a caspase-3-dependent pathway, European Journal of Medicinal Chemistry, 46: 2141-2146 (2011).
Grzonka et al., Cysteine Proteases, Industrial Enzymes, 181-195 (2007).
Han et al., Targeted prodrug design to optimize drug delivery, AAPS Pharmsci., 2(1):1-11 (2000).
Han et al., Papain-Like Protease 2 (PLP2) from Severe Acute Respiratory Syndrome Coronavirus (SARS-CoV): Expression, Purification, Characterization, and Inhibition, Biochemistry, 44: 10349-10359 (2005).
Hanzlik et al., "Vinylogous Amino Acid Esters: A New Class of Inactivators for Thiol Proteases," J. Med. Chem. 27:711-712, 1984.
Liu et al., "Structure-Activity Relationships for Inhibition of Papain by Peptide Michael Acceptors," J. Med. Chem. 35:1067-1075, 1992.
Merrifield, "Solid Phase Peptide Synthesis. I. The Synthesis of a Tetrapeptide," J. Am. Chem. Soc. 85:2149-2154, 1963.
Müller, Prodrug approaches for enhancing the bioavailability of drugs with low solubility, Chem & Biodiv., 6:2071-83 (2009).
Nazif et al., "Global Analysis of Proteasomal Substrate Specificity Using Positional-Scanning Libraries of Covalent Inhibitors," Proc. Natl. Acad. Sci. U.S.A. 98:2967-2972, 2001.
Newton et al., Synthesis and evaluation of vinyl sulfones as caspase-3 inhibitors: A structure-activity study, European Journal of Medicinal Chemistry, 45: 3858-3863 (2010).
Ng et al., "Click" synthesis of small-molecule inhibitors targeting caspases, Organic & Biomolecular Chemistry, 6: 844-847 (2008).
Rawlings et al., "Evolutionary Families of Peptidases," Biochem. J. 290:205-218, 1993.
Rodriguez et al., Systemic Injector of a Tripeptide Inhibits the Intracellular Activation of CPP32-like Proteases in Vivo and Fully Protects Mica against Fas-mediated Fulminant Liver Destruction and Death, J. Exp. Med., 184: 2067-2072 (1996).
Santos et al., Michael Acceptors as Cysteine Protease Inhibitors, Mini-Reviews in Medicinal Chemistry, 7: 1040-1050 (2007).
Singh et al., Recent trends in targeted anticancer prodrug and conjugate design, Curr Med Chem., 15(18):1802-26 (2008).
Testa, Prodrug research: futile or ferrile, Biochem Pharma., 68:2097-2106 (2004).
Thompson et al., "Carboxyl-Modified Amino Acids and Peptides as Protease Inhibitors," J. Med. Chem. 29:104-111, 1986.
Tong, Liang, Viral Proteases, Chem. Rev., 102: 4609-4626 (2002).
Uttamchandani et al., Activity-based fingerprinting and inhibitor discovery of cysteine proteases in a microarray, Chem. Commun., 1518-1520 (2007).
Wagh et al., Allylic amination of internal alkynes with aromatic and aliphatic amines using polymer-supported triphenylphosphane-palladium complex as a heterogeneous and recyclable catalyst, European Journal of Organic Chemistry, 26: 5071-5076 (2010).

(56) References Cited

OTHER PUBLICATIONS

Wissinger et al., Profilingg protein function with small molecule microarrays, Proc. Natl. Acad. Sci. 99(17), 11139-11144, 2002.
Yaoita et al., Attenuation of Ischemia/Reperfusion Injury in Rats by a Caspase Inhibitor, Circulation, 97: 276-281 (1998).
International Search Report from International Application No. PCT/CA2009.000696 dated Jul. 9, 2009 (date of completion of search) and Sep. 1, 2009 (date of mailing of report).
Written Opinion from International Application No. PCT/CA2009.000696 dated Jul. 24, 2009 (date of completion of opinion) and Sep. 1, 2009 (date of mailing of opinion).
Chinese Office Action for Chinese Application No. 200980128709.7, State Intellectual Office of the P.R. of China, mailed Sep. 11, 2012.

SELECTIVE CASPASE INHIBITORS AND USES THEREOF

CROSS REFERENCE TO RELATED APPLICATIONS

The present application is a continuation of U.S. patent application Ser. No. 12/993,565, filed Nov. 19, 2010, now U.S. Pat. No. 8,791,235, which is the U.S. national stage filing of international application PCT/CA2009/000696, filed May 21, 2009, which in turn claims the priority benefit of U.S. Patent Application No. 61/128,253, filed May 21, 2008. These applications and any other applications for which a foreign or domestic priority claim is identified in the Application Data Sheet filed with the present application are hereby incorporated by reference in their entireties herein.

FIELD OF INVENTION

The present invention relates to chemical compounds and their pharmaceutical uses. More particularly, the invention relates to selective inhibitors of caspases and their uses for the prevention and/or treatment of various diseases and conditions in subjects.

BACKGROUND OF INVENTION

Caspases comprise a family of cysteine protease enzymes with a well-known role as key mediators in apoptosis signaling pathways and cell disassembly. Interleukin converting enzyme (ICE), also known as Caspase-1, was the first identified caspase. In humans, 11 other known caspases have been further identified. Caspases have been classified in two general groups according to their effects: proapoptotic (caspase-2, 3, 6, 7, 8, 9, 10) and proinflammatory (caspase-1, 4, 5, 11, 12) caspases. The proapoptotic caspases have been divided in initiators (caspase-2, 8, 9, 10) also known as group II, and executioners (caspase-3, 6, 7) of the apoptotic process or group III. The Interleukin converting enzyme (ICE) also known as Caspase-1 has a proinflammatory role only.

There is growing evidence demonstrating the role of caspases in very diverse pathologies. For instance it is known that proapoptotic caspases are involved in the pathogenesis of many cardiovascular disorders. Some proapoptotic caspases such as caspase-8 also possess non-apoptotic function that may contribute to tumor progression. Caspase-1 plays an important role in response to pathogenic infection as well as in inflammatory and autoimmune disorders. In addition, caspase-1 activity is increased in retinas of diabetic patients and it constitutes a critical regulator of cardiomyocyte programmed cell death in the mammalian heart. Caspases also plays a role in neurodegenerative diseases and trauma. For instance, it has been shown that the caspase-3 cascade is highly activated due to the traumatic spinal cord injury. Finally, the activation of caspase-1 and caspase-3 in Amyotrophic Lateral Sclerosis (ALS) patients and the activation of caspase-7, -8, and -9 in a mouse model at end stage of ALS have been reported. Increased levels of apoptosis and caspase activity (especially caspase-3) are reported to be frequently observed at sites of cellular damage in both acute (e.g. Sepsis, myocardial infarction (MI), Ischemic Stroke, Spinal cord injury (SCI), traumatic Brain Injury (TBI)) and neurodegenerative disease (e.g. Alzheimer's, Parkinson's and Huntington's diseases, and multiple sclerosis (MS)).

Since caspases are involved in a number of diseases, several compounds and methods have been developed to inactivate them. For example, the broad irreversible caspase inhibitor benzyloxycarbonyl-Val-Ala-Asp-fluoromethylketone (z-VAD-fmk) was protective and efficiently blocked death receptor-mediated liver injury in animal models (Rodriguez et al. (1996), J Exp Med. 1996 Nov. 1; 184(5):2067-72). Myocardial infarction and the resulting death of myocytes was ameliorated by z-VAD-fmk and related peptide inhibitors in animal models (Yaoita et al., 91998) Circulation 97: 276-281). There have been also a lot of efforts for identifying inhibitors of peptidase. For instance, Hanzlik and Thompson (J. Med. Chem. (1984), 27(6), 711-712) describe vinylogous amino acid esters for inactivating thiol proteases. Thompson et al. (J. Med. Chem. (1986), 29(1), 104-111) describe carboxyl-modified amino acids and peptides as protease inhibitors. Liu and Hanzlik have prepared a series of peptidyl Michael acceptors with different electron withdrawing groups with different recognition and binding groups as inactivators against papain, a member of the cysteine proteinase family. Similarly, U.S. Pat. Nos. 5,976,858 and 6,287,840 to Palmer wt et al. describes irreversible cysteine protease inhibitors containing vinyl groups conjugated to electron withdrawing groups. However, these and other compounds are not effective against caspases, because caspases are among the most specific endopeptidases.

Given their role in several diseases and conditions, there is a need for compounds capable of selectively targeting either a specific caspase or a group of caspases. There is also a need for effective pharmaceutical compositions and method of treatment for caspase-related diseases.

The present invention addresses these needs for novel therapies, new treatment methods, compounds, and pharmaceutical compositions.

Additional features of the invention will be apparent from review of the disclosure, figures and description of the invention below.

BRIEF SUMMARY OF THE INVENTION

The present invention relates to compounds according to any of Formula I, IA, II, IIA, III, or IIIA as defined herein, compositions thereof and methods for the prevention and/or treatment of caspase-related diseases in subjects. Particular aspects of the invention relates to use of compounds according to any of Formula I, IA, II, IIA, III, or IIIA as defined herein.

One aspect of the invention concerns a method for preventing and/or treating a caspase-related disease in a subject in need thereof, comprising administering to said subject an effective amount of a compound represented by any of Formula I, IA, II, IIA, III, or IIIA as defined herein.

One aspect of the invention concerns the use of a compound a compound represented by any of Formula I, IA, II, IIA, III, or IIIA as defined herein for preventing and/or treating of caspase-related diseases in a subject in need thereof.

Another related aspect of the invention concerns the use of a compound represented by any of Formula I, IA, II, IIA, III, or IIIA as defined herein for the manufacture of a medication for preventing and/or treating of caspase-related diseases in a subject in need thereof.

One aspect of the invention concerns a method of treating excessive apoptosis affected by caspase activity in a cell or a tissue, the method comprising: contacting the cell or tissue with an effective amount of one or more compounds represented by any of Formula I, IA, II, IIA, III, or IIIA as defined herein, so as to treat the excessive apoptosis.

One particular aspect of the invention concerns the use of a compound represented by any of Formula I, IA, II, IIA, III, or IIIA as defined herein for use in apoptosis mediated diseases.

Caspase-related disease as defined herein are selected from the group consisting of apoptosis mediated diseases, IL-1 mediated diseases, inflammatory diseases, autoimmune diseases, autoinflammatory diseases, proliferative diseases, infectious diseases, degenerative diseases, retinal disorders, inflammatory peritonitis, osteoarthritis, pancreatitis, asthma, respiratory distress syndrome, rheumatoid arthritis, systemic lupus erythematous, scleroderma, Grave's disease, autoimmune gastritis, diabetes, autoimmune hemolytic anemia, autoimmune neutropenia, thrombocytopenia, hepatitis, inflammatory bowel disease, crohn's disease, psoriasis, dermatitis, Graft vs host disease, organ transplant rejection, osteoporosis, leukemias and related disorders, multiple myeloma-related diseases, metastatic melanomas, Kaposi's sarcoma, sepsis, septic shock, Alzheimer's disease, Parkinson's disease, Huntington's disease, cerebral ischemia, epilepsy, myocardial ischemia, acute and chronic heart disease, myocardial infarction, congestive heart failure, atherosclerosis, spinal muscular atrophy, amyotrophic lateral sclerosis, multiple sclerosis, HIV-related encephalitis, aging, neurological damage due to stroke, ulcerative colitis, traumatic brain injury, spinal cord injury, hepatitis-B, hepatitis-C, hepatitis-G, liver-related diseases, renal disease, and HIV infection.

Specific examples of compounds according to the invention are represented in Table 1.

The invention also provides methods and strategies of targeting caspases. In one embodiment the approach consists of designing a suicide substrate leading to a permanent inhibition of the caspase. Preferably, the approach consists of designing a substrate that is recognizable enough for caspases, especially one or more specific caspase(s), to fit into it, to be potentially cleaved at a specific position in a way that makes the caspase enzyme irreversibly linked to the substrate thereby leading to a permanent inhibition of the caspase. In some embodiments, the suicide substrates of this invention are vinyl electron withdrawing group (EWG). compounds may be effective for use in caspase-mediated diseases such as sepsis, myocardial infarction, ischemic stroke, spinal cord injury (SCI), traumatic brain injury (TBI) and neurodegenerative disease (e.g. multiple sclerosis (MS) and Alzheimer's, Parkinson's, and Huntington's diseases).

B) Compounds of the Invention

Broadly speaking, the invention concerns a compound represented by Formula I

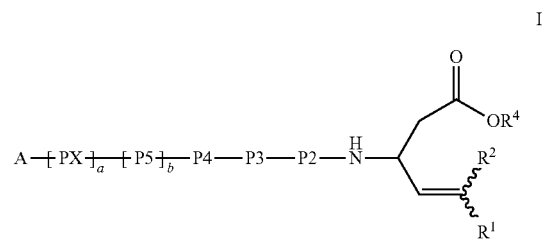

wherein A, PX, P5, P4, P3, P2, $R^1$, $R^2$, a and b are as defined hereinabove and hereinbelow;

or a prodrug, or a pharmaceutically acceptable salt to allow the drug to penetrate the cell membrane or the compound is labeled with a detectable label or an affinity tag thereof.

The line "–" when located between P2, P3, P4, P5 and PX represents a peptide bond or a peptidomimetic bond; The PX, P5, P4, P3, P2 amino acid residues are normally linked via a peptide bond, that is, a peptidic carbamoyl group, i.e. —CONH—. However, peptidomimetic bonds are also contemplated, such as $CH_2$—NH, CO—$CH_2$, azapeptide and retro-inverso bonds.

The $R^1$ and $R^2$ that are bonded to the vinyl group can be either in the cis configuration or the trans configuration, as represented by the wavy lines. In one example, $R^1$ is configured to be trans such that the electron withdrawing capability of the $R^1$ group is stabilized.

Further included within the scope of the invention are compounds of Formula IA:

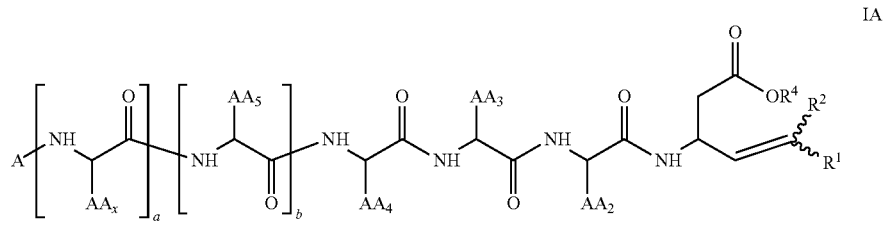

Further aspects of the invention will be apparent to a person skilled in the art from the following description, and claims and generalizations therein.

DETAILED DESCRIPTION OF THE INVENTION

A) General Overview of the Invention

The present inventors have discovered compounds that have beneficial pharmaceutical properties and that these wherein A, $AA_X$, $AA_5$, $AA_4$, $AA_3$, $AA_2$, $R^1$, $R^2$, a and b are as defined hereinabove and hereinbelow;

or a prodrug, or a pharmaceutically acceptable salt to allow the drug to penetrate the cell membrane, or the compound is labeled with a detectable label or an affinity tag thereof.

Thus, when a and b are both 0, the present invention includes compounds of Formula II:

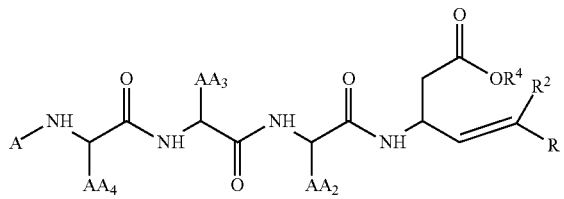

II wherein A, AA$_4$, AA$_3$, AA$_2$, R$^1$, and R$^2$ are as defined hereinabove and hereinbelow. Furthermore, when a is 0 and b is 1, the present invention includes compounds of Formula III

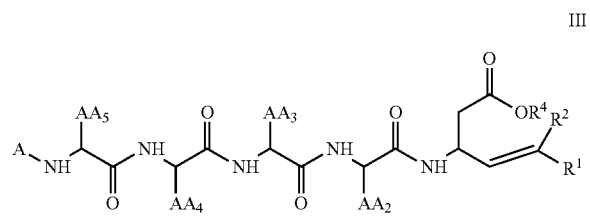

III wherein A, AA$_5$, AA$_4$, AA$_3$, AA$_2$, R$^1$, and R$^2$ are as defined hereinabove and hereinbelow. One subset of compounds of Formula II includes compounds of Formula IIA:

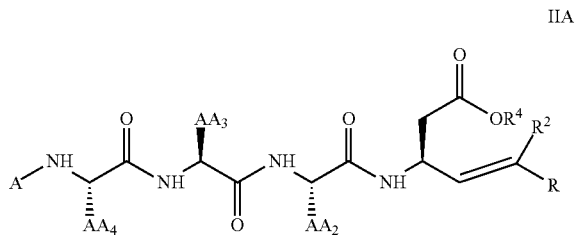

IIA wherein A, AA$_4$, AA$_3$, AA$_2$, R$^1$, and R$^2$ are as defined hereinabove and hereinbelow.

One subset of compounds of Formula III includes compounds of Formula IIIA:

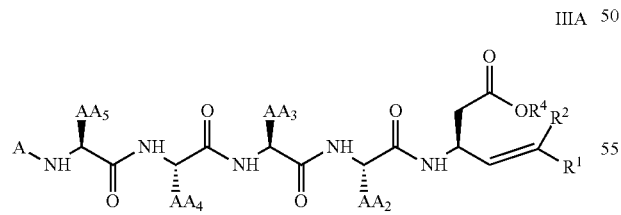

IIIA wherein A, AA$_5$, AA$_4$, AA$_3$, AA$_2$, R$^1$, and R$^2$ are as defined hereinabove and hereinbelow.

a and b:

In one subset of compounds of the invention, a is 0 or 1; and b is 0 or 1 provided that when b is 0, a is 0.

In one example, a and b are both 0.

In another example, a is 0 and b is 1.

A:
In one subset, A is
1) H,
2) C$_1$-C$_6$ alkyl,
3) aryl,
4) heteroaryl,
5) heterocyclyl,
6) R$^3$—OC(O)—;
7) R$^3$—C(O)O—, or
8) R$^3$—S(O)$_2$—;
wherein R$^3$ is
1) C$_1$-C$_6$ alkyl,
2) aryl,
3) heteroaryl, or
4) heterocyclyl.
In one example, A is H.
In one example, A is R$^3$—OC(O)—.
In one example, A is PhCH$_2$OC(O)—.

R$^1$:
In one subset, R$^1$ is an electron withdrawing group (EWG) selected from
1) aryl,
2) heteroaryl,
3) heterocyclyl,
4) C$_2$-C$_6$ alkene-R$^{20}$,
5) SO$_2$R$^5$,
6) SO$_3$R$^5$,
7) SOR$^5$,
8) SONHR$^5$,
9) SO$_2$NHR$^5$,
10) CN,
11) CO$_2$R$^5$,
12) COR$^5$,
13) PO$_3$R$^5$,
14) PO(OR$^5$)$_2$, or
15) PO(OR$^5$),
wherein the aryl, the heteroaryl, or the heterocyclyl are optionally substituted with one or more R$^{30}$.

R$^2$:
In one subset, R$^2$ is
1) R$^1$; or
2) H,
3) halogen,
4) haloalkyl,
5) C$_1$-C$_6$ alkyl,
6) C$_2$-C$_6$ alkene,
7) C$_3$-C$_7$ cycloalkyl,
8) OR$^9$;
9) OCOR$^6$,
10) OCO$_2$R$^6$,
11) NR$^7$R$^8$,
12) NHSO$_2$R$^6$,
13) NHCOR$^6$,
14) aryl,
15) heteroaryl, or
16) heterocyclyl;
wherein R$^1$, R$^6$, R$^7$, R$^8$ and R$^9$ are as defined hereinabove and hereinbelow.
In one example, R$^2$ is H.
In another example, R$^2$ is halogen.
In yet another example, R$^2$ is Cl.

R$^4$:
In one subset, R$^4$ is
1) H, or
2) methyl, ethyl, propyl, or tert-butyl.
In one example, R$^4$ is H.

$R^5$:

In one subset, $R^5$ is
1) H,
2) $C_1$-$C_6$ alkyl,
3) $C_2$-$C_6$ alkene,
4) $C_3$-$C_7$ cycloalkyl,
5) aryl,
6) heteroaryl,
7) heterocyclyl, or
8) any optionally protected (D) or (L) amino acid residue.

$R^6$:

In one subset, $R^6$ is
1) any (D) or (L) amino acid residue,
2) $C_1$-$C_6$ alkyl,
3) $C_3$-$C_7$ cycloalkyl,
4) aryl,
5) heteroaryl, or
6) heterocyclyl,
in which the alkyl or the cycloalkyl are optionally substituted with one or more $R^{10}$ substituents; and in which the aryl, heteroaryl or heterocyclyl are optionally substituted with one or more $R^{20}$ substituents.

$R^7$ and $R^8$:

In one subset, $R^7$ and $R^8$ are independently selected from:
1) H,
2) $C_1$-$C_6$ alkyl,
3) $C_3$-$C_7$ cycloalkyl,
4) haloalkyl,
5) aryl,
6) heteroaryl, or
7) heterocyclyl,
wherein the alkyl and the cycloalkyl are optionally substituted with one or more $R^{10}$ substituents, and the aryl, the heteroaryl and the heterocyclyl are optionally substituted with one or more $R^{20}$ substituents.

$R^9$:

In one subset, $R^9$ is
1) H,
2) $C_1$-$C_6$ alkyl,
3) $C_3$-$C_7$ cycloalkyl,
4) aryl,
5) heteroaryl, or
6) heterocyclyl,
in which the alkyl or the cycloalkyl are optionally substituted with one or more $R^{10}$ substituents; and in which the aryl, heteroaryl or heterocyclyl are optionally substituted with one or more $R^{20}$ substituents.

$R^{10}$:

In one subset, $R^{10}$ is independently selected from:
1) halogen,
2) $C_1$-$C_6$ alkyl,
3) $C_3$-$C_7$ cycloalkyl,
4) haloalkyl,
5) aryl,
6) heteroaryl,
7) heterocyclyl,
8) $OR^9$,
9) $S(O)_mR^9$,
10) $NR^7R^8$,
11) $COR^9$,
12) $C(O)OR^9$,
13) $OC(O)R^9$,
14) $SC(O)R^9$,
15) $CONR^7R^8$, or
16) $S(O)_2NR^7R^8$;

wherein $R^7$, $R^8$, $R^9$ are as defined hereinabove and hereinbelow;
m is an integer of 0, 1, or 2.

$R^{20}$:

In one subset, $R^{20}$ is independently selected from:
1) halogen,
2) $NO_2$,
3) CN,
4) $C_1$-$C_6$ alkyl,
5) haloalkyl,
6) $C_3$-$C_7$ cycloalkyl,
7) $OR^7$,
8) $NR^7R^8$,
9) $SR^7$,
10) aryl,
11) heteroaryl,
12) heterocyclyl,
13) $SO_2R^5$,
14) $SO_3R^5$,
15) $SOR^5$,
16) $SONHR^5$,
17) $SO_2NHR^5$,
18) $PO_3R^5$,
19) $PO(OR^5)_2$,
20) $PO(OR^5)$,
21) $COR^7$,
22) $CO_2R^7$,
23) $S(O)_mR^7$,
24) $CONR^7R^8$, or
25) $S(O)_2NR^7R^8$,
wherein the alkyl and the cycloalkyl are optionally substituted with one or more $R^6$ substituents; and wherein the aryl, the heteroaryl, or the heterocyclyl are optionally substituted with one or more $R^{30}$.
wherein $R^7$, $R^8$ and m are as defined hereinabove and hereinbelow.

$R^{30}$:

In one subset, $R^{30}$ is
1) $NO_2$,
2) $C_2$-$C_6$ alkene-$R^{20}$,
3) $SO_2R^5$,
4) $SOR^5$,
5) $SONHR^5$,
6) $SO_2NHR^5$,
7) CN,
8) $CO_2R^5$,
9) $COR^5$,
10) $PO_3R^5$,
11) $PO(OR^5)_2$, or
12) $PO(OR^5)$;
wherein $R^5$ and $R^{20}$ are as defined hereinabove and hereinbelow.

Caspase 3 Inhibitors

The present invention includes compounds of Formula IIA:

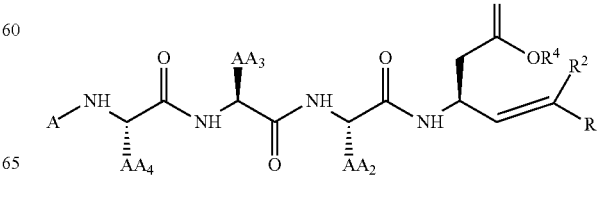

IIA wherein

AA$_2$ is the amino acid side chain of Val, Leu, Pro, Met, Ala, Thr, His.

AA$_3$ is the amino acid side chain of Trp, Tyr, Ala, Asp, Glu, Gln, Phe, Ser, Thr, Val, Tyr, Gly, Leu; or AA$_3$ is phenylglycine, indanylglycine, or Ala-(2'-quinolyl);

AA$_4$ is the amino acid side chain of Asp;

and wherein A, R$^1$, R$^2$ and R$^4$ are as defined hereinabove and hereinbelow.

Caspase 8/Caspase 9 Inhibitors

The present invention includes compounds of Formula IIA:

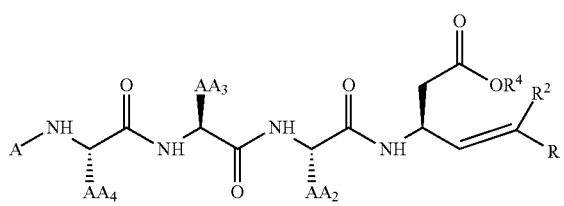

wherein

AA$_2$ is the amino acid side chain of Thr, His, Val, Trp, Ile, or Ala

AA$_3$ is the amino acid side chain of Glu or AA$_3$ is Ala-(2'-quinolyl);

AA$_4$ is the amino acid side chain of Ile, Leu, Glu, Asp, Ala, Pro or Val;

and wherein A, R$^1$, R$^2$ and R$^4$ are as defined hereinabove and hereinbelow.

Caspase 2 Inhibitors

The present invention includes compounds of Formula IIIA

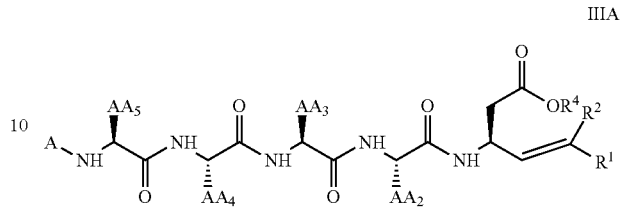

wherein

AA$_2$ is the amino acid side chain of Ala, Ser, Lys or Val;

AA$_3$ is the amino acid side chain of Val, Glu, Thr, or Gln;

AA$_4$ is the amino acid side chain of Asp, or Leu;

AA$_5$ is the amino acid side chain of Val or Leu;

and wherein A, R$^1$, R$^2$ and R$^4$ are as defined hereinabove and hereinbelow.

Caspase 1 Inhibitors

The present invention includes compounds of Formula IIA (caspase 1 inhibitors)

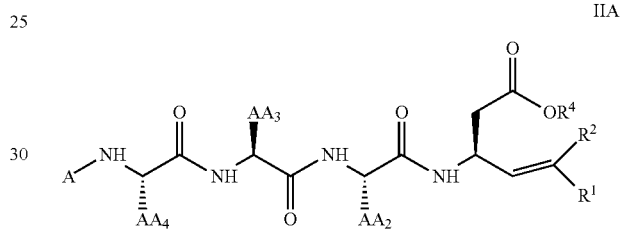

wherein

AA$_2$ is the amino acid side chain of Val, Ala, Thr, or His;

AA$_3$ is the amino acid side chain of Glu, Gln, Asp, Ala, Gly, Thr, Val, Trp; or AA$_3$ is phenylglycine or indanylglycine;

AA$_4$ is the amino acid side chain of Tyr, Trp, Phe, or Asp;

and wherein A, R$^1$, R$^2$ and R$^4$ are as defined hereinabove and hereinbelow.

Compounds and intermediate compounds synthesized according to the present invention include those in Table 1:

TABLE 1

| CPD N° | CPD NAME | STRUCTURE |
|---|---|---|
| 1 | Fmoc-Ala(2'-quinolyl)-Val-OAllyl | 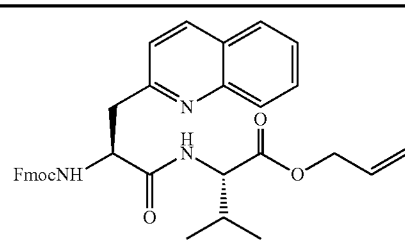 |
| 2 | Ala(2'quinolyl)-Val-OAllyl | 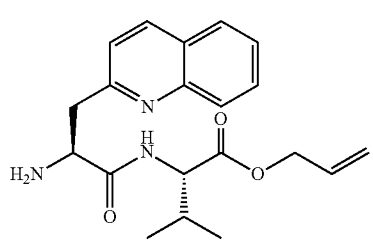 [SMILES: C=CCOC(=O)[C@@H](NC(=O)[C@@H](N)Cc1ccc2ccccc2n1)C(C)C] |

TABLE 1-continued
| CPD N° | CPD NAME | STRUCTURE |
|---|---|---|
| 3 | Cbz-Asp(O—tBu)-Ala(2'-quinolyl)-Val-OAllyl | 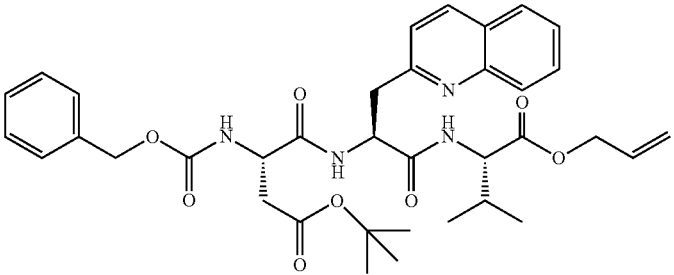 [SMILES: C=CCOC(=O)[C@@H](NC(=O)[C@H](Cc1ccc2ccccc2n1)NC(=O)[C@H](CC(=O)OC(C)(C)C)NC(=O)OCc1ccccc1)C(C)C] |
| 4 | Cbz-Asp(O—tBu)-Ala(2'-quinolyl)-ValOH | 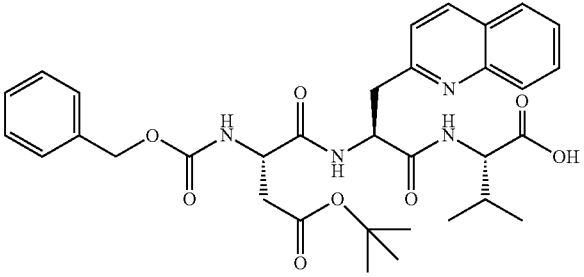 [SMILES: CC(C)[C@H](NC(=O)[C@H](Cc1ccc2ccccc2n1)NC(=O)[C@H](CC(=O)OC(C)(C)C)NC(=O)OCc1ccccc1)C(=O)O] |
| 5 | Ts-Ala(2'-quinolyl)-Val-OH | 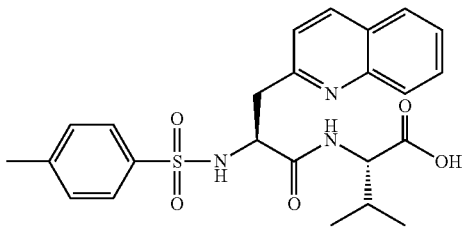 [SMILES: Cc1ccc(S(=O)(=O)N[C@@H](Cc2ccc3ccccc3n2)C(=O)N[C@H](C(=O)O)C(C)C)cc1] |
| 6 | Ts-Ala(2'-quinolyl)-OH | 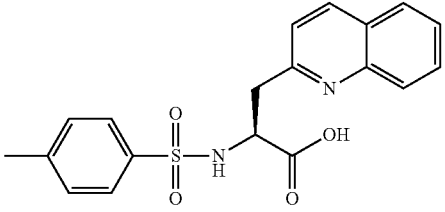 [SMILES: Cc1ccc(S(=O)(=O)N[C@@H](Cc2ccc3ccccc3n2)C(=O)O)cc1] |
| 7 | Ts-Ala(2'-quinolyl)-Val-OAllyl | 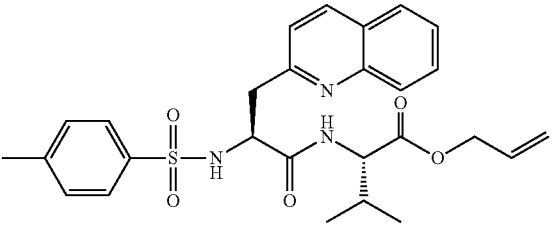 [SMILES: C=CCOC(=O)[C@@H](NC(=O)[C@H](Cc1ccc2ccccc2n1)NS(=O)(=O)c1ccc(C)cc1)C(C)C] |
| 8 | Z-Asp(OtBu)-Tyr(OtBu)-Val-Asp(OtBu)methyl vinyl sulfone | 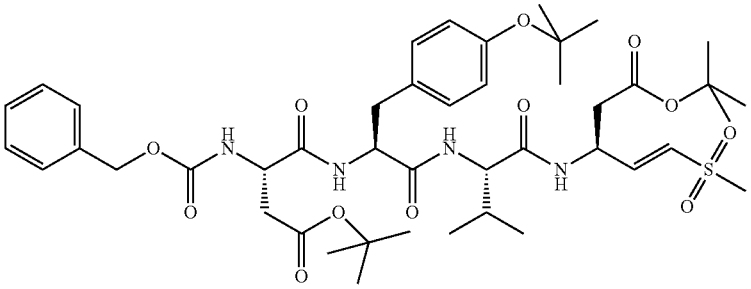 [SMILES: CC(C)[C@H](NC(=O)[C@H](Cc1ccc(OC(C)(C)C)cc1)NC(=O)[C@H](CC(=O)OC(C)(C)C)NC(=O)OCc1ccccc1)C(=O)N[C@H](/C=C/S(C)(=O)=O)CC(=O)OC(C)(C)C] |

TABLE 1-continued

| CPD N° | CPD NAME | STRUCTURE |
|---|---|---|
| 9 | Fmoc-Indanylglycine-Val-OAllyl | 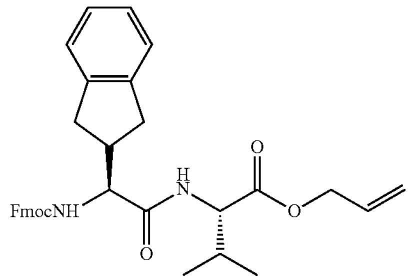 |
| 10 | Indanylglycine-Val-OAllyl | 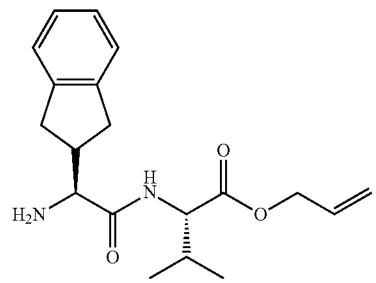 [SMILES: C=CCOC(=O)[C@@H](NC(=O)[C@@H](N)C1Cc2ccccc2C1)C(C)C] |
| 11 | Cbz-Asp(O—tBu)-Indanylglycine-Val-OAllyl | 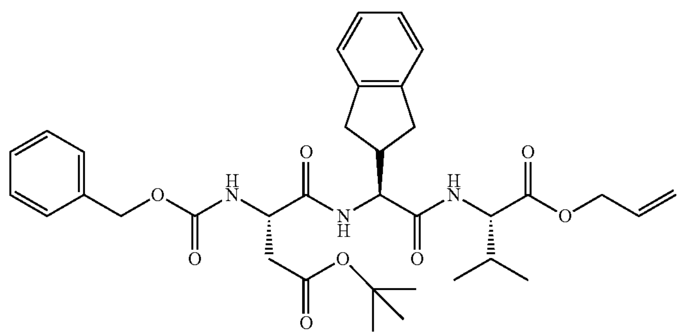 [SMILES: C=CCOC(=O)[C@@H](NC(=O)[C@@H](NC(=O)[C@H](CC(=O)OC(C)(C)C)NC(=O)OCc1ccccc1)C1Cc2ccccc2C1)C(C)C] |
| 12 | Cbz-Asp(O—tBu)Indanylglycine-Val-OH | 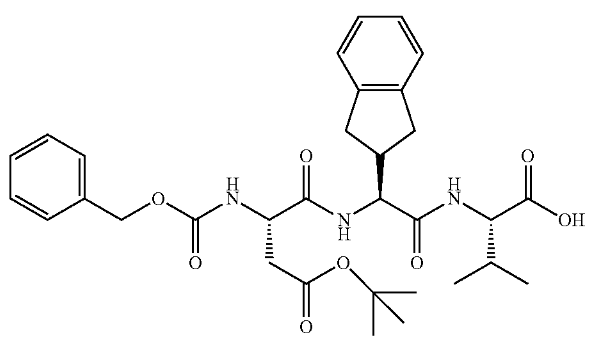 [SMILES: CC(C)[C@H](NC(=O)[C@@H](NC(=O)[C@H](CC(=O)OC(C)(C)C)NC(=O)OCc1ccccc1)C1Cc2ccccc2C1)C(=O)O] |
| 13 | Fmoc-Phg-Val-OAllyl | 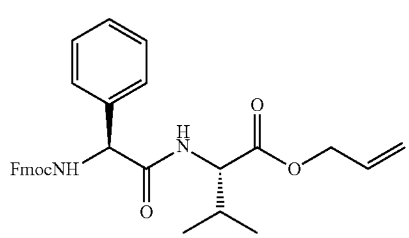 |

TABLE 1-continued

| CPD N° | CPD NAME | STRUCTURE |
|---|---|---|
| 14 | Phg-Val-OAllyl | 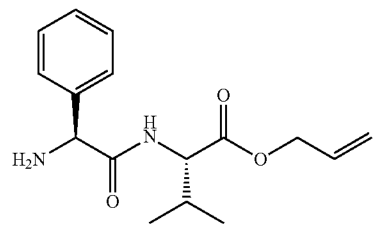 [SMILES: C=CCOC(=O)[C@@H](NC(=O)[C@@H](N)c1ccccc1)C(C)C] |
| 15 | Z-Asp(β-tert-Butyl)-Phg-Val-OAllyl. | 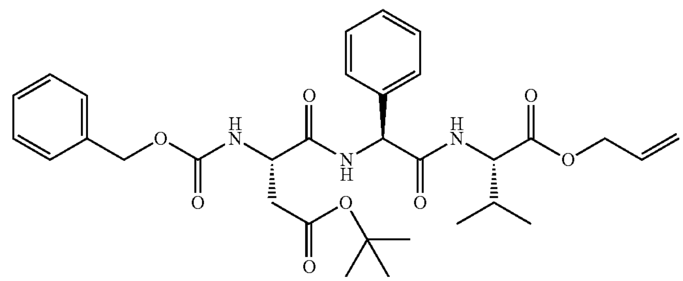 [SMILES: C=CCOC(=O)[C@@H](NC(=O)[C@@H](NC(=O)[C@H](CC(=O)OC(C)(C)C)NC(=O)OCc1ccccc1)c1ccccc1)C(C)C] |
| 16 | Z-Asp(β-tert-Butyl)-Phg-Val-OH. | 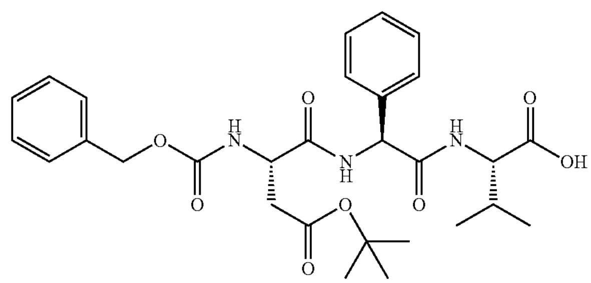 [SMILES: CC(C)[C@H](NC(=O)[C@@H](NC(=O)[C@H](CC(=O)OC(C)(C)C)NC(=O)OCc1ccccc1)c1ccccc1)C(=O)O] |
| 17 | Fmoc-Glu(O—tBu)-Val-OAllyl | 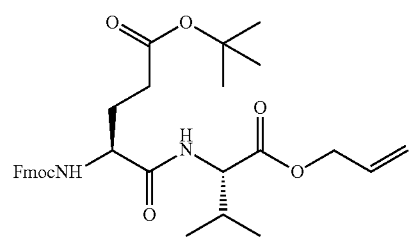 |
| 18 | Glu(O—tBu)-Val-OAllyl | 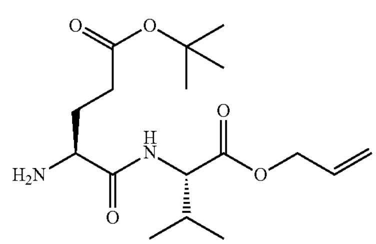 [SMILES: C=CCOC(=O)[C@@H](NC(=O)[C@@H](N)CCC(=O)OC(C)(C)C)C(C)C] |
| 19 | Cbz-Asp(O—tBu)-Glu(O—tBu)-Val-OAllyl | 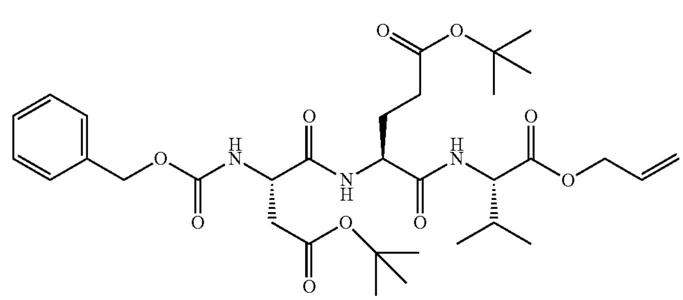 [SMILES: C=CCOC(=O)[C@@H](NC(=O)[C@H](CCC(=O)OC(C)(C)C)NC(=O)[C@H](CC(=O)OC(C)(C)C)NC(=O)OCc1ccccc1)C(C)C] |

TABLE 1-continued

| CPD N° | CPD NAME | STRUCTURE |
|---|---|---|
| 20 | Cbz-Asp(O—tBu)-Glu(O—tBu)-Val-OH | 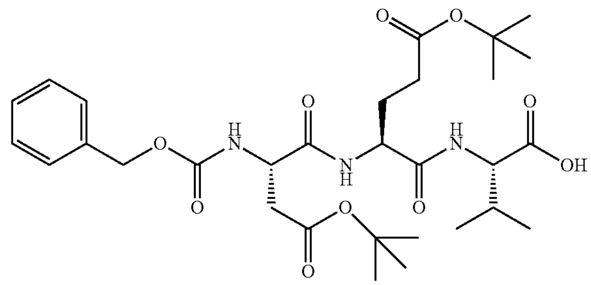 [SMILES: CC(C)[C@H](NC(=O)[C@H](CCC(=O)OC(C)(C)C)NC(=O)[C@H](CC(=O)OC(C)(C)C)NC(=O)OCc1ccccc1)C(=O)O] |
| 21 | Diethyl chloro(methylsulfone)methylphosphonate | 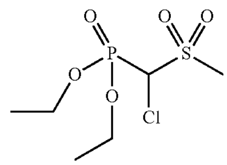 |
| 22 | Boc-Asp (β-tert-butyl) αchlorovinyl methylsulfone | 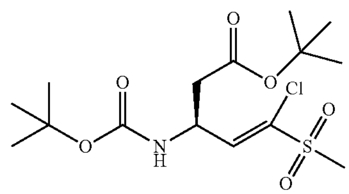 [SMILES: CC(C)(C)OC(=O)C[C@@H](/C=C(\Cl)S(C)(=O)=O)NC(=O)OC(C)(C)C] |
| 23 | Asp(β-tert-butyl)αchlorovinyl methylsulfone tosyl salt | 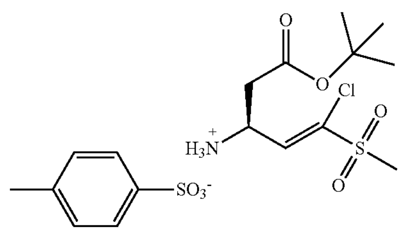 |
| 24 | Diethyl chloro(phenylsulfone)methylphosphonate | 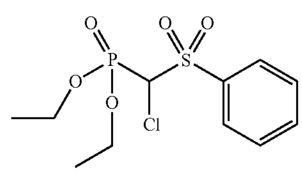 [SMILES: CCOP(=O)(OCC)C(Cl)S(=O)(=O)c1ccccc1] |
| 25 | Asp(β-tert-butyl)αchlorovinyl phenylsulfone | 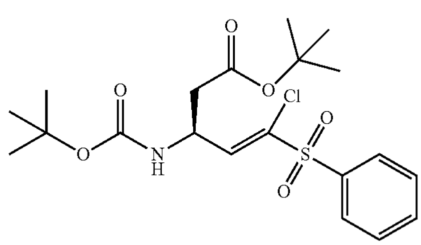 [SMILES: CC(C)(C)OC(=O)C[C@@H](/C=C(\Cl)S(=O)(=O)c1ccccc1)NC(=O)OC(C)(C)C] |
| 26 | Asp(β-tert-butyl)αchlorovinyl phenylsulfone tosyl salt | 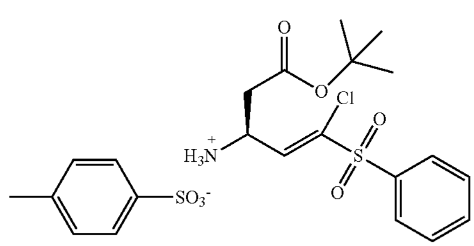 |

TABLE 1-continued

| CPD N° | CPD NAME | STRUCTURE |
|---|---|---|
| 27 | Boc-Aspartimol(β-Methyl) | 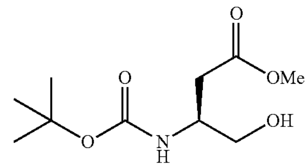 [SMILES: COC(=O)C[C@@H](CO)NC(=O)OC(C)(C)C] |
| 28 | Boc-Asp(β-Methyl)-H | 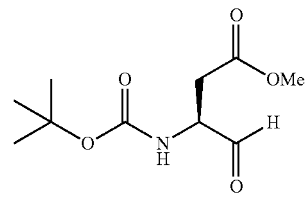 [SMILES: COC(=O)C[C@@H](C=O)NC(=O)OC(C)(C)C] |
| 29 | Boc-Asp(β-Methyl)methyl vinyl sulfone | 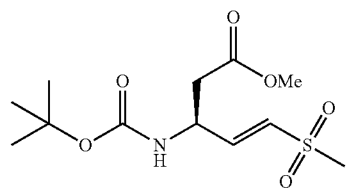 [SMILES: COC(=O)C[C@@H](/C=C/S(C)(=O)=O)NC(=O)OC(C)(C)C] |
| 30 | Boc-Asp(β-Methyl)methyl vinyl sulfone tosyl salt | 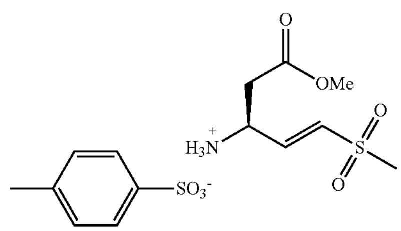 |
| 31 | Diethyl (methylsulfone) methylphosphonate | 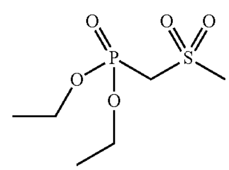 |
| 32 | Boc-Asp(β-tert-butyl)methyl vinyl sulfone | 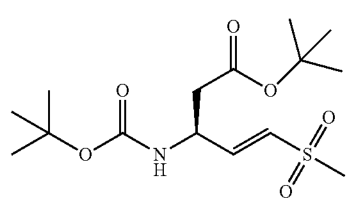 [SMILES: CC(C)(C)OC(=O)C[C@@H](/C=C/S(C)(=O)=O)NC(=O)OC(C)(C)C] |
| 33 | Asp(β-tert-butyl)methyl vinyl sulfone tosyl salt | 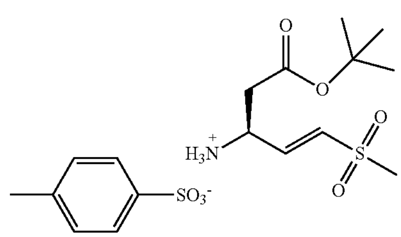 |
| 34 | Diethyl phenylsulfonyl-methylphosphonate | 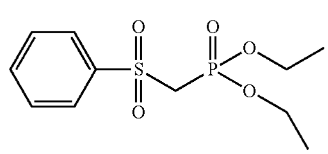 [SMILES: CCOP(=O)(CS(=O)(=O)c1ccccc1)OCC] |

TABLE 1-continued

| CPD N° | CPD NAME | STRUCTURE |
|---|---|---|
| 35 | Boc-Asp(β-tert-Butyl)-H | 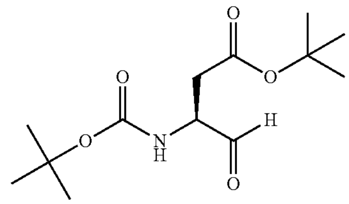 [SMILES: CC(C)(C)OC(=O)C[C@@H](C=O)NC(=O)OC(C)(C)C] |
| 36 | Boc-Asp-vinyl phenyl sulfone | 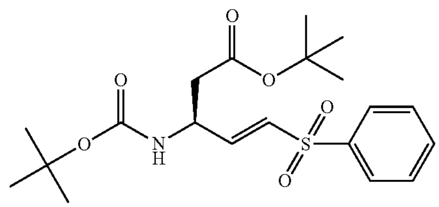 [SMILES: CC(C)(C)OC(=O)C[C@@H](/C=C/S(=O)(=O)c1ccccc1)NC(=O)OC(C)(C)C] |
| 37 | Asp Vinyl phenyl sulfone tosyl salt | 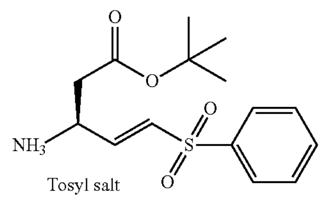 [SMILES: CC(C)(C)OC(=O)C[C@H](N)/C=C/S(=O)(=O)c1ccccc1] |
| 38 | Diethyl (phenoxysulfone) methylphosphonate | 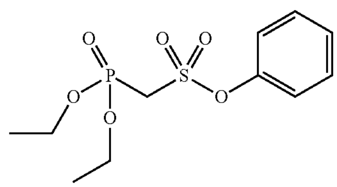 [SMILES: CCOP(=O)(CS(=O)(=O)Oc1ccccc1)OCC] |
| 39 | Asp(β-tert-butyl) phenoxy vinyl sulfone | 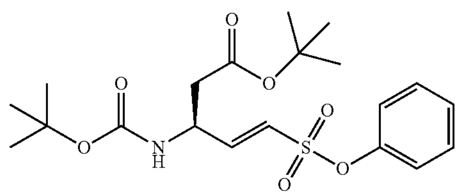 [SMILES: CC(C)(C)OC(=O)C[C@@H](/C=C/S(=O)(=O)Oc1ccccc1)NC(=O)OC(C)(C)C] |
| 40 | Asp(β-tert-butyl) phenoxy vinyl sulfone tosyl salt | 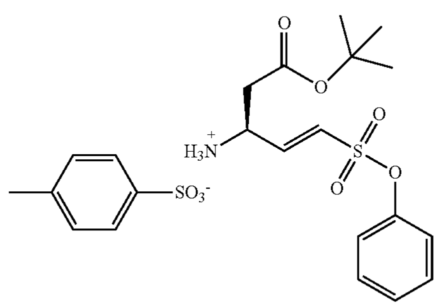 |
| 41 | Diethyl (isopropylsulfone) methylphosphonate | 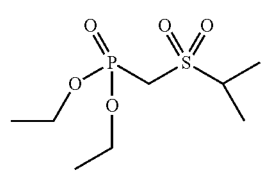 |

TABLE 1-continued

| CPD N° | CPD NAME | STRUCTURE |
|---|---|---|
| 42 | BocAsp(β-tert-butyl) isopropyl vinyl sulfone | 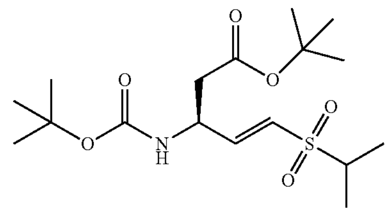 [SMILES: CC(C)S(=O)(=O)/C=C/[C@H](CC(=O)OC(C)(C)C)NC(=O)OC(C)(C)C] |
| 43 | Asp(β-tert-butyl)isopropyl vinyl sulfone tosyl salt | 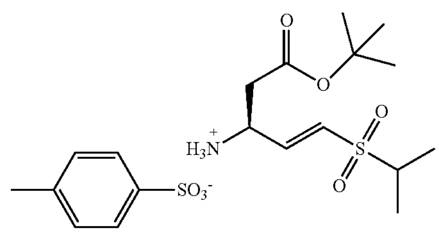 |
| 44 | Diethyl (morpholinesulfone) methylphosphonate | 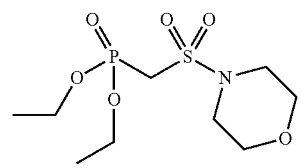 [SMILES: CCOP(=O)(CS(=O)(=O)N1CCOCC1)OCC] |
| 45 | Boc-Asp(β-tert-butyl)morpholine vinyl sulfone | 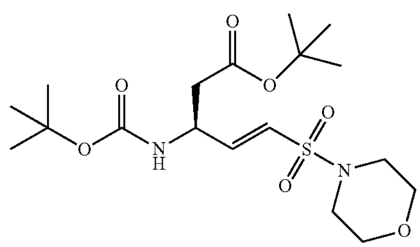 [SMILES: CC(C)(C)OC(=O)C[C@@H](/C=C/S(=O)(=O)N1CCOCC1)NC(=O)OC(C)(C)C] |
| 46 | Asp(β-tert-butyl)morpholine vinyl sulfone tosyl salt | 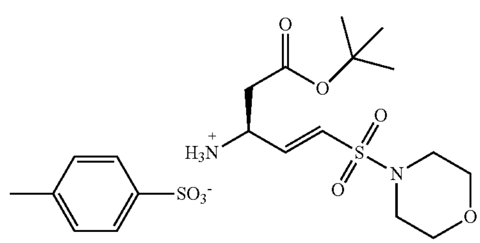 |
| 47 | Z-Asp(β-tert-Butyl)-Ala(2'-quinolyl)-Val-Asp(β-tert-Butyl)αchlorovinyl methylsulfone | 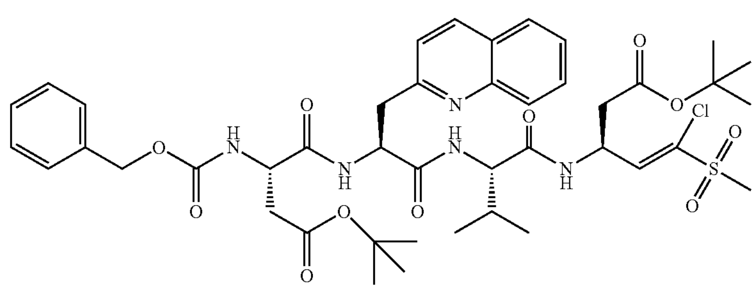 [SMILES: CC(C)[C@H](NC(=O)[C@H](Cc1ccc2ccccc2n1)NC(=O)[C@H](CC(=O)OC(C)(C)C)NC(=O)OCc1ccccc1)C(=O)N[C@H](/C=C(\Cl)S(C)(=O)=O)CC(=O)OC(C)(C)C] |

TABLE 1-continued
| CPD N° | CPD NAME | STRUCTURE |
|---|---|---|
| 48 | Z-Asp-Ala(2'-quinolyl)-Val-Asp-αchlorovinyl methylsulfone | 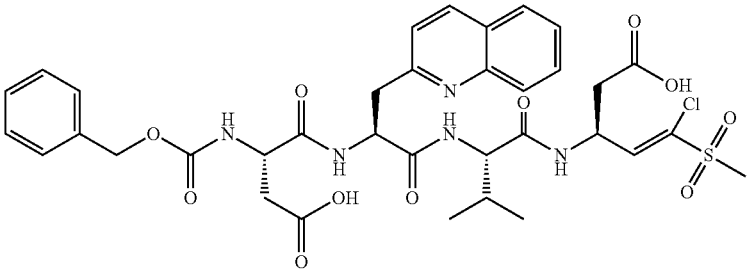 [SMILES: CC(C)[C@H](NC(=O)[C@H](Cc1ccc2ccccc2n1)NC(=O)[C@H](CC(=O)O)NC(=O)OCc1ccccc1)C(=O)N[C@H](/C=C(\Cl)S(C)(=O)=O)CC(=O)O] |
| 49 | Ts-Ala(2'quinolyl)-Val-Asp(β-tert-Butyl)-αchlorovinyl methylsulfone | 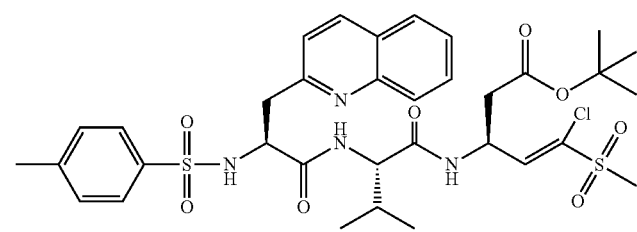 [SMILES: Cc1ccc(S(=O)(=O)N[C@@H](Cc2ccc3ccccc3n2)C(=O)N[C@H](C(=O)N[C@H](/C=C(\Cl)S(C)(=O)=O)CC(=O)OC(C)(C)C)C(C)C)cc1] |
| 50 | Ts-Ala(2'quinolyl)-Val-Asp-αchlorovinyl methylsulfone | 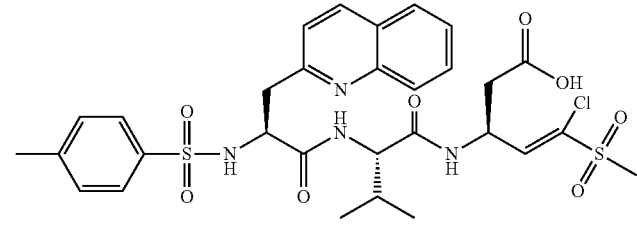 |
| 51 | Z-Asp(β-methyl)-Indanylglycine-Val-Asp(β-methyl)methyl vinyl sulfone | 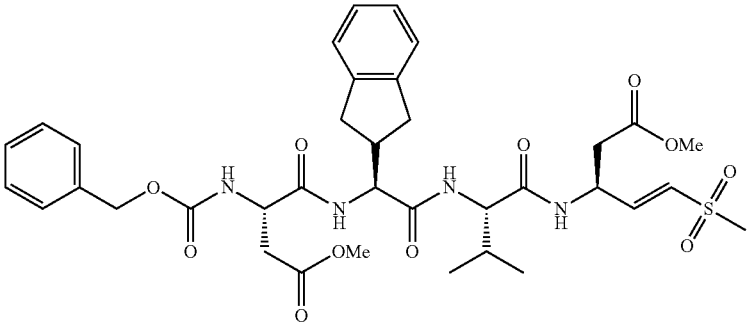 [SMILES: COC(=O)C[C@@H](/C=C/S(C)(=O)=O)NC(=O)[C@@H](NC(=O)[C@@H](NC(=O)[C@H](CC(=O)OC)NC(=O)OCc1ccccc1)C1Cc2ccccc2C1)C(C)C] |
| 52 | Z-Asp(β-tert-Butyl)-Phg-Val-Asp(β-tert-Butyl)methyl vinyl sulfone | 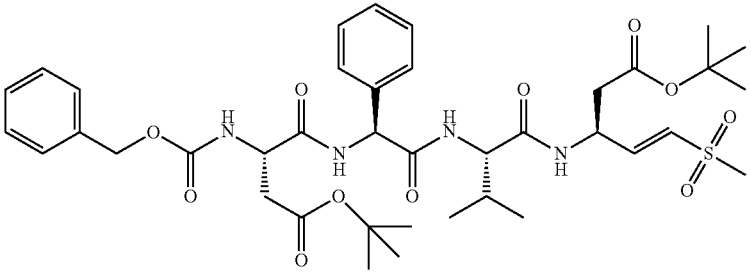 [SMILES: CC(C)[C@H](NC(=O)[C@@H](NC(=O)[C@H](CC(=O)OC(C)(C)C)NC(=O)OCc1ccccc1)c1ccccc1)C(=O)N[C@H](/C=C/S(C)(=O)=O)CC(=O)OC(C)(C)C] |

TABLE 1-continued

| CPD N° | CPD NAME | STRUCTURE |
|---|---|---|
| 53 | Z-Asp-Phg-Val-Aspmethyl vinyl sulfone | 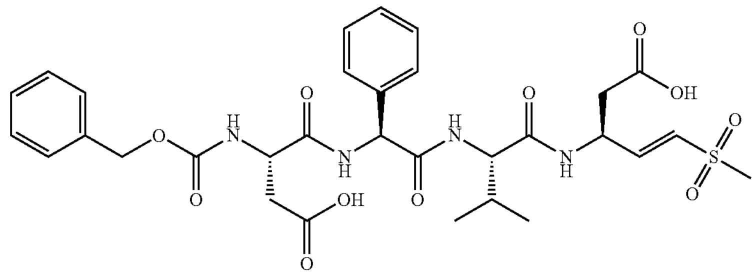 [SMILES: CC(C)[C@H](NC(=O)[C@@H](NC(=O)[C@H](CC(=O)O)NC(=O)OCc1ccccc1)c1ccccc1)C(=O)N[C@H](/C=C/S(C)(=O)=O)CC(=O)O] |
| 54 | Z-Asp(β-tert-Butyl)-Al(2'-quinolyl)-Val-Asp(β-tert-Butyl)methyl vinyl sulfone | 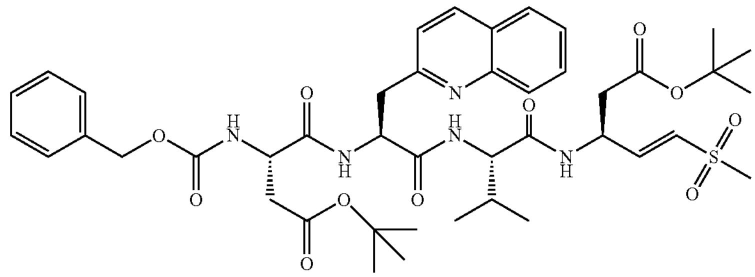 [SMILES: CC(C)[C@H](NC(=O)[C@H](Cc1ccc2ccccc2n1)NC(=O)[C@H](CC(=O)OC(C)(C)C)NC(=O)OCc1ccccc1)C(=O)N[C@H](/C=C/S(C)(=O)=O)CC(=O)OC(C)(C)C] |
| 55 | Z-Asp-Ala(2'-quinolyl)-Val-Aspmethyl vinyl sulfone | 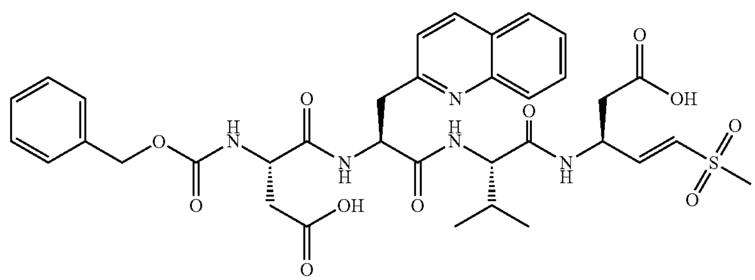 [SMILES: CC(C)[C@H](NC(=O)[C@H](Cc1ccc2ccccc2n1)NC(=O)[C@H](CC(=O)O)NC(=O)OCc1ccccc1)C(=O)N[C@H](/C=C/S(C)(=O)=O)CC(=O)O] |
| 56 | Z-Asp(β-tert-Butyl)-Indanyl-glycine-Val-Asp(β-tert-Butyl) methyl vinyl sulfone | 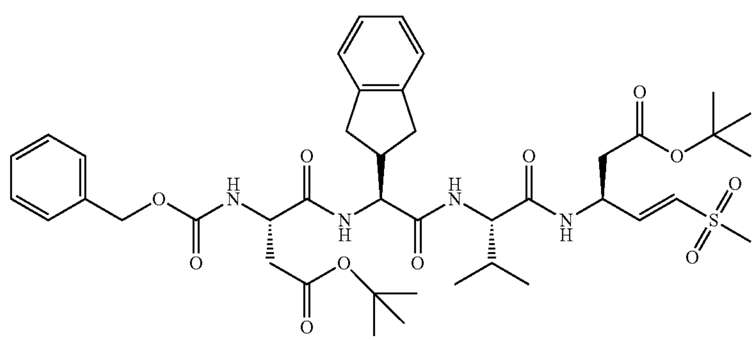 [SMILES: CC(C)[C@H](NC(=O)[C@@H](NC(=O)[C@H](CC(=O)OC(C)(C)C)NC(=O)OCc1ccccc1)C1Cc2ccccc2C1)C(=O)N[C@H](/C=C/S(C)(=O)=O)CC(=O)OC(C)(C)C] |
| 57 | Z-Asp-Indanylglycine-Val-Aspmethyl vinyl sulfone | 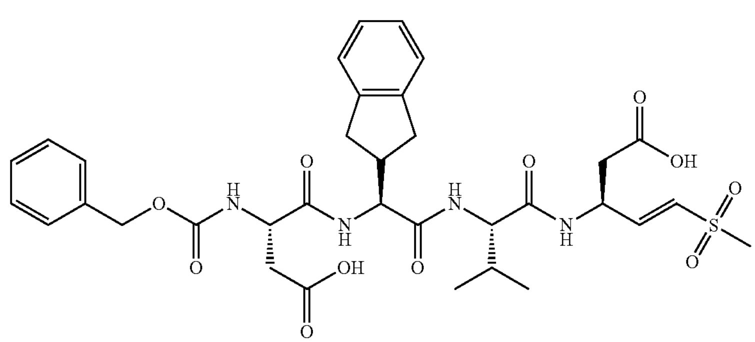 [SMILES: CC(C)[C@H](NC(=O)[C@@H](NC(=O)[C@H](CC(=O)O)NC(=O)OCc1ccccc1)C1Cc2ccccc2C1)C(=O)N[C@H](/C=C/S(C)(=O)=O)CC(=O)O] |

TABLE 1-continued

| CPD N° | CPD NAME | STRUCTURE |
|---|---|---|
| 58 | Z-Asp(β-tert-Butyl)-Glu(β-tert-Butyl)-Val-Asp(β-tert-Butyl)methyl vinyl sulfone | 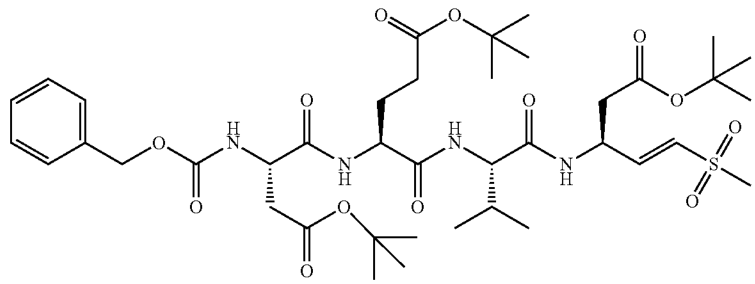 [SMILES: CC(C)[C@H](NC(=O)[C@H](CCC(=O)OC(C)(C)C)NC(=O)[C@H](CC(=O)OC(C)(C)C)NC(=O)OCc1ccccc1)C(=O)N[C@H](/C=C/S(C)(=O)=O)CC(=O)OC(C)(C)C] |
| 59 | Z-Asp-Glu-Val-Aspmethyl vinyl sulfone | 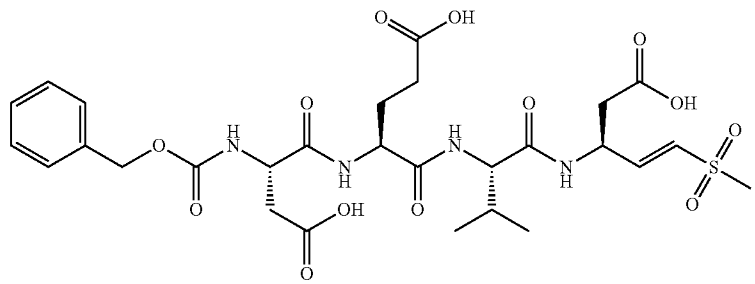 [SMILES: CC(C)[C@H](NC(=O)[C@H](CCC(=O)O)NC(=O)[C@H](CC(=O)O)NC(=O)OCc1ccccc1)C(=O)N[C@H](/C=C/S(C)(=O)=O)CC(=O)O] |
| 60 | Z-Val-Asp(β-tert-Butyl)methyl vinyl sulfone | 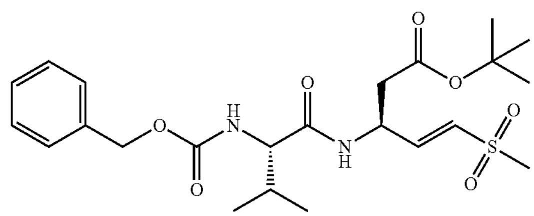 [SMILES: CC(C)[C@H](NC(=O)OCc1ccccc1)C(=O)N[C@H](/C=C/S(C)(=O)=O)CC(=O)OC(C)(C)C] |
| 61 | Z-Val-Aspmethyl vinyl sulfone | 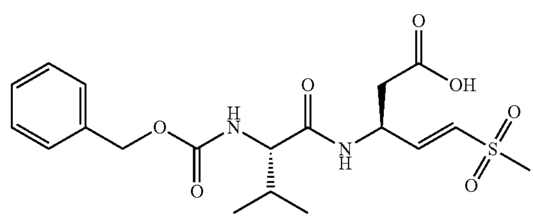 [SMILES: CC(C)[C@H](NC(=O)OCc1ccccc1)C(=O)N[C@H](/C=C/S(C)(=O)=O)CC(=O)O] |
| 62 | Z-Asp(β-tert-Butyl)-Ala(2'-quinolyl)-Val-Asp(β-tert-Butyl)phenyl vinyl sulfone | 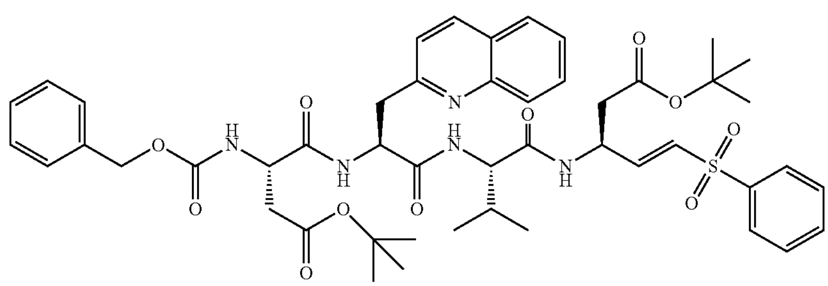 [SMILES: CC(C)[C@H](NC(=O)[C@H](Cc1ccc2ccccc2n1)NC(=O)[C@H](CC(=O)OC(C)(C)C)NC(=O)OCc1ccccc1)C(=O)N[C@H](/C=C/S(=O)(=O)c1ccccc1)CC(=O)OC(C)(C)C] |
| 63 | Z-Asp-Ala(2'-quinolyl)-Val-Aspphenyl vinyl sulfone | 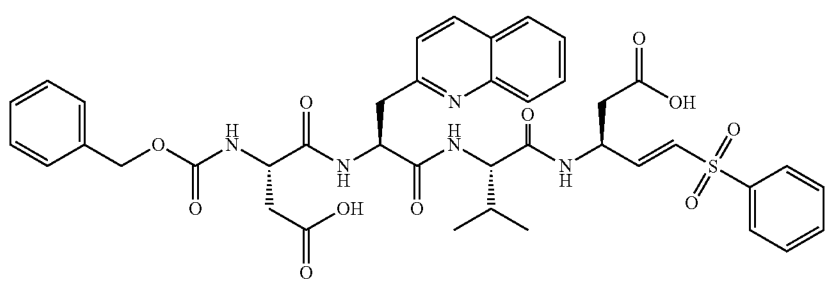 [SMILES: CC(C)[C@H](NC(=O)[C@H](Cc1ccc2ccccc2n1)NC(=O)[C@H](CC(=O)O)NC(=O)OCc1ccccc1)C(=O)N[C@H](/C=C/S(=O)(=O)c1ccccc1)CC(=O)O] |

TABLE 1-continued

| CPD N° | CPD NAME | STRUCTURE |
|---|---|---|
| 64 | Z-Asp(β-tert-Butyl)-Ala(2'-quinolyl)-Val-Asp(β-tert-Butyl)phenoxy vinyl sulfone | 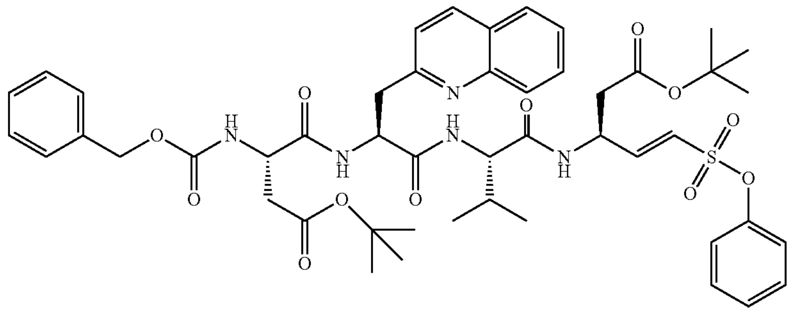 [SMILES: CC(C)[C@H](NC(=O)[C@H](Cc1ccc2ccccc2n1)NC(=O)[C@H](CC(=O)OC(C)(C)C)NC(=O)OCc1ccccc1)C(=O)N[C@H](/C=C/S(=O)(=O)Oc1ccccc1)CC(=O)OC(C)(C)C] |
| 65 | Z-Asp-Ala(2'-quinolyl)-Val-Aspphenoxy vinyl sulfone | 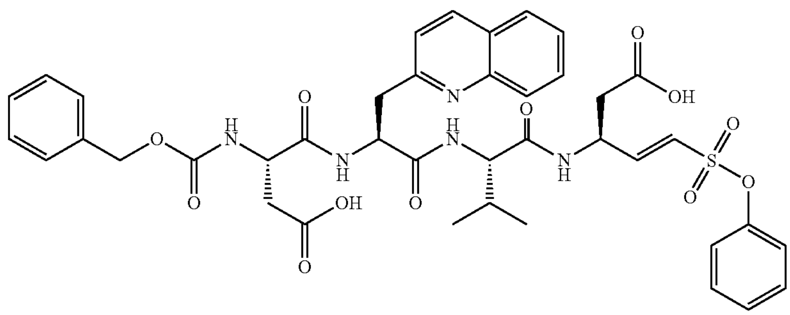 [SMILES: CC(C)[C@H](NC(=O)[C@H](Cc1ccc2ccccc2n1)NC(=O)[C@H](CC(=O)O)NC(=O)OCc1ccccc1)C(=O)N[C@H](/C=C/S(=O)(=O)Oc1ccccc1)CC(=O)O] |
| 66 | Z-Asp(β-tert-Butyl)-Ala(2'-quinolyl)-Val-Asp(β-tert-Butyl)morpholine vinyl sulfone | 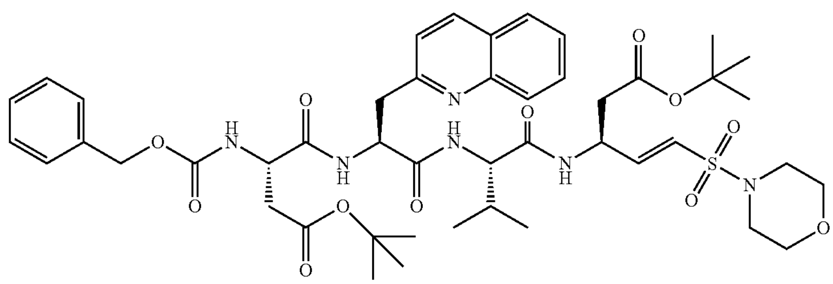 [SMILES: CC(C)[C@H](NC(=O)[C@H](Cc1ccc2ccccc2n1)NC(=O)[C@H](CC(=O)OC(C)(C)C)NC(=O)OCc1ccccc1)C(=O)N[C@H](/C=C/S(=O)(=O)N1CCOCC1)CC(=O)OC(C)(C)C] |
| 67 | Z-Asp-Ala(2'-quinolyl)-Val-Aspmorpholine vinyl sulfone | 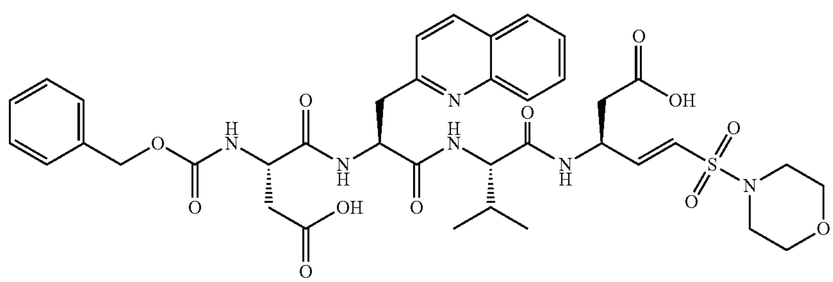 [SMILES: CC(C)[C@H](NC(=O)[C@H](Cc1ccc2ccccc2n1)NC(=O)[C@H](CC(=O)O)NC(=O)OCc1ccccc1)C(=O)N[C@H](/C=C/S(=O)(=O)N1CCOCC1)CC(=O)O] |
| 68 | Z-Asp-Indanylglycine-Val-Aspisopropyl vinyl sulfone | 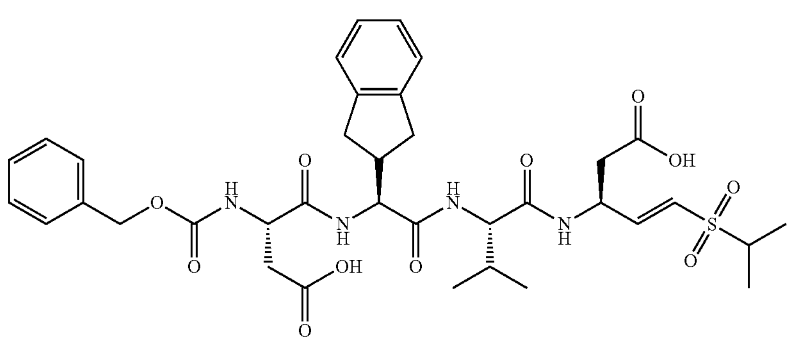 [SMILES: CC(C)[C@H](NC(=O)[C@@H](NC(=O)[C@H](CC(=O)O)NC(=O)OCc1ccccc1)C1Cc2ccccc2C1)C(=O)N[C@H](/C=C/S(=O)(=O)C(C)C)CC(=O)O] |

TABLE 1-continued
| CPD N° | CPD NAME | STRUCTURE |
|---|---|---|
| 69 | Z-Asp-Phg-Val-Asp-phenyl vinylsulfone | 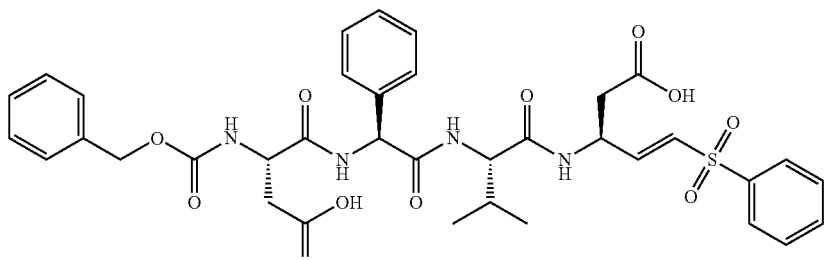 |
| 70 | Z-Asp-(D,L Ala(2'-quinolyl))-Val-Aspphenyl vinylsulfone | 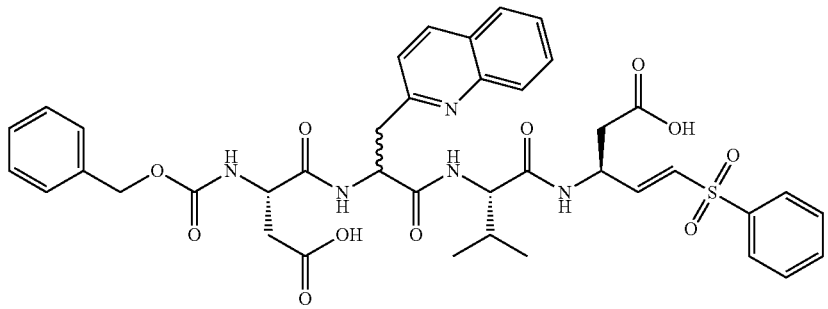 [SMILES: CC(C)[C@H](NC(=O)C(Cc1ccc2ccccc2n1)NC(=O)[C@H](CC(=O)O)NC(=O)OCc1ccccc1)C(=O)N[C@H](/C=C/S(=O)(=O)c1ccccc1)CC(=O)O] |
| 71 | Z-Asp-(D,L Ala(2'-quinolyl))-Val-Aspmethyl vinylsulfone | 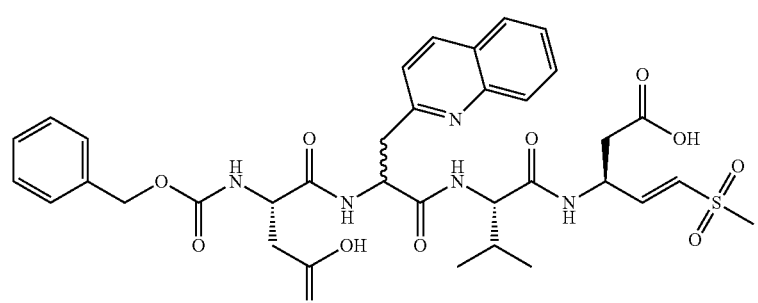 |
| 72 | Fmoc-Tyr(O—tBu)-Val-Oallyl | 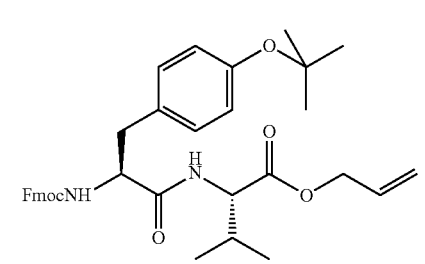 |
| 73 | Tyr(O—tBu)-Val-Oallyl | 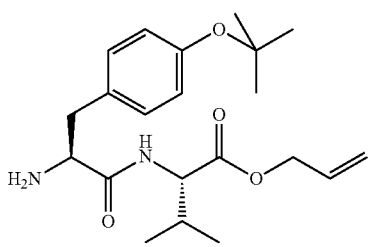 [SMILES: C=CCOC(=O)[C@@H](NC(=O)[C@@H](N)Cc1ccc(OC(C)(C)C)cc1)C(C)C] |

TABLE 1-continued
| CPD N° | CPD NAME | STRUCTURE |
|---|---|---|
| 74 | Z-Asp(O—tBu)-Tyr(O—tBu)-Val-Oallyl | 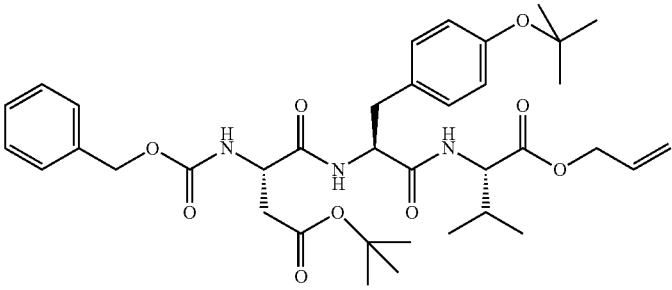 [SMILES: C=CCOC(=O)[C@@H](NC(=O)[C@H](Cc1ccc(OC(C)(C)C)cc1)NC(=O)[C@H](CC(=O)OC(C)(C)C)NC(=O)OCc1ccccc1)C(C)C] |
| 75 | Z-Asp-Tyr(O—tBu)-Val-OH | 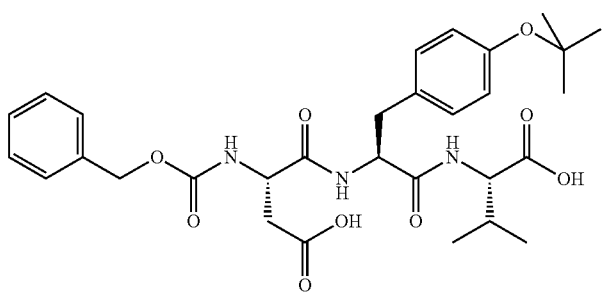 [SMILES: CC(C)[C@H](NC(=O)[C@H](Cc1ccc(OC(C)(C)C)cc1)NC(=O)[C@H](CC(=O)O)NC(=O)OCc1ccccc1)C(=O)O] |
| 76 | Z-Asp-Tyr-Val-Aspmethyl vinyl sulfone | 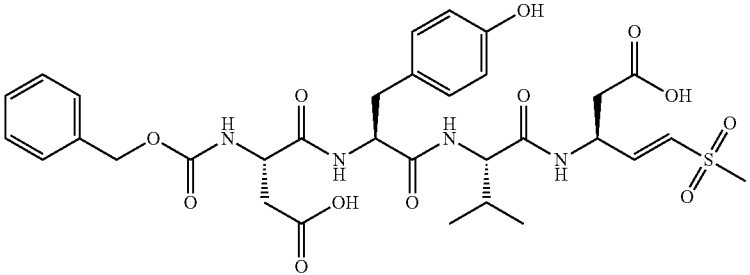 [SMILES: CC(C)[C@H](NC(=O)[C@H](Cc1ccc(O)cc1)NC(=O)[C@H](CC(=O)O)NC(=O)OCc1ccccc1)C(=O)N[C@H](/C=C/S(C)(=O)=O)CC(=O)O] |
| 77 | Fmoc-Glu(O—tBu)-Val-Oallyl | 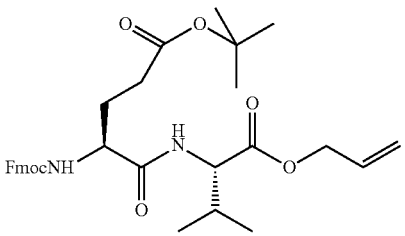 |
| 78 | Glu(O—tBu)-Val-Oallyl | 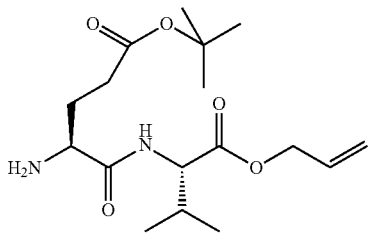 [SMILES: C=CCOC(=O)[C@@H](NC(=O)[C@@H](N)CCC(=O)OC(C)(C)C)C(C)C] |

TABLE 1-continued

| CPD N° | CPD NAME | STRUCTURE |
|---|---|---|
| 79 | Z-Tyr(O—tBu)-Glu(O—tBu)-Val-Oallyl | 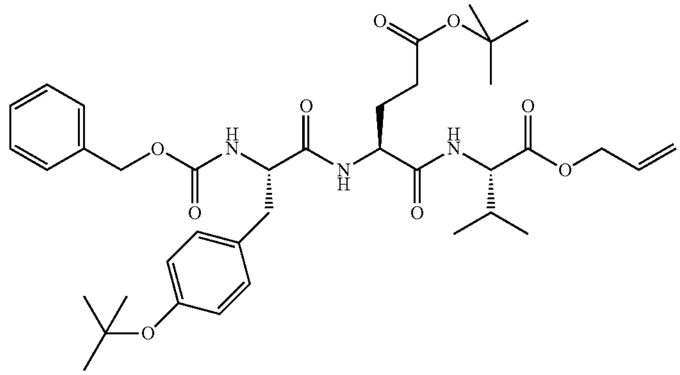 [SMILES: C=CCOC(=O)[C@@H](NC(=O)[C@H](CCC(=O)OC(C)(C)C)NC(=O)[C@H](Cc1ccc(OC(C)(C)C)cc1)NC(=O)OCc1ccccc1)C(C)C] |
| 80 | Z-Tyr(O—tBu)-Glu(O—tBu)-Val-OH | 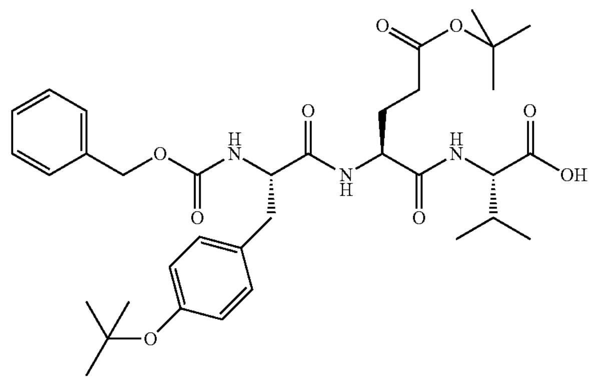 [SMILES: CC(C)[C@H](NC(=O)[C@H](CCC(=O)OC(C)(C)C)NC(=O)[C@H](Cc1ccc(OC(C)(C)C)cc1)NC(=O)OCc1ccccc1)C(=O)O] |
| 81 | Z-Tyr(O—tBu)-Glu(O—tBu)-Val-Asp(OtBu)methyl vinyl sulfone | 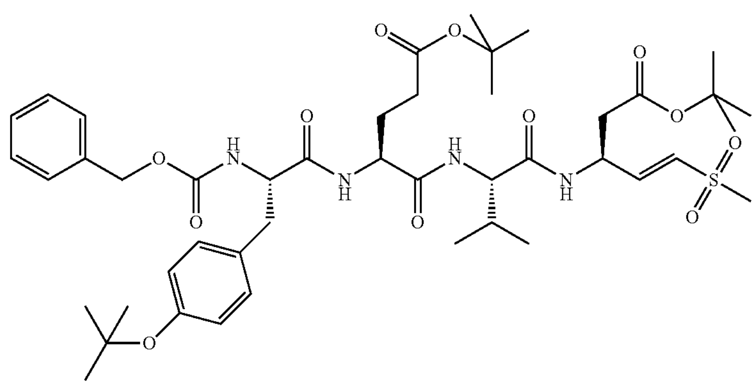 [SMILES: CC(C)[C@H](NC(=O)[C@H](CCC(=O)OC(C)(C)C)NC(=O)[C@H](Cc1ccc(OC(C)(C)C)cc1)NC(=O)OCc1ccccc1)C(=O)N[C@H](/C=C/S(C)(=O)=O)CC(=O)OC(C)(C)C] |
| 82 | Z-Tyr-Glu-Val-Aspmethyl vinyl sulfone | 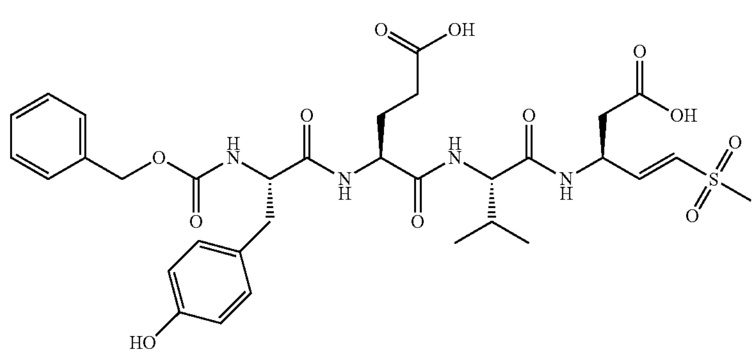 [SMILES: CC(C)[C@H](NC(=O)[C@H](CCC(=O)O)NC(=O)[C@H](Cc1ccc(O)cc1)NC(=O)OCc1ccccc1)C(=O)N[C@H](/C=C/S(C)(=O)=O)CC(=O)O] |

TABLE 1-continued
| CPD N° | CPD NAME | STRUCTURE |
|---|---|---|
| 83 | Z-Asp(O—tBu)-Ala-(2'pyridine)-Val-OH | 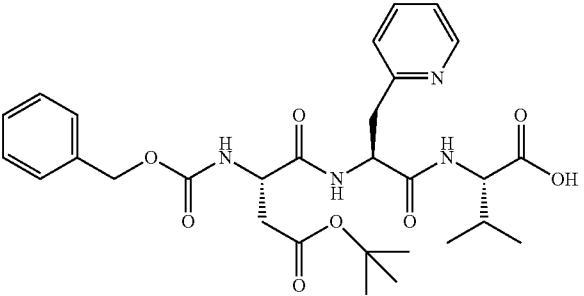 [SMILES: CC(C)[C@H](NC(=O)[C@H](Cc1ccccn1)NC(=O)[C@H](CC(=O)OC(C)(C)C)NC(=O)OCc1ccccc1)C(=O)O] |
| 84 | Z-Asp(O—tBu)-Ala-(2'pyridine)-Val-Asp(O—tBu)phenyl vinyl sulfone | 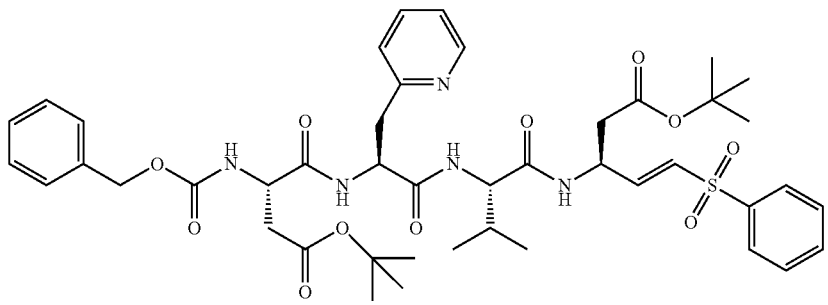 [SMILES: CC(C)[C@H](NC(=O)[C@H](Cc1ccccn1)NC(=O)[C@H](CC(=O)OC(C)(C)C)NC(=O)OCc1ccccc1)C(=O)N[C@H](/C=C/S(=O)(=O)c1ccccc1)CC(=O)OC(C)(C)C] |
| 85 | Z-Asp-Ala(2'-pyridyl)-Val-Aspphenyl vinylsulfone | 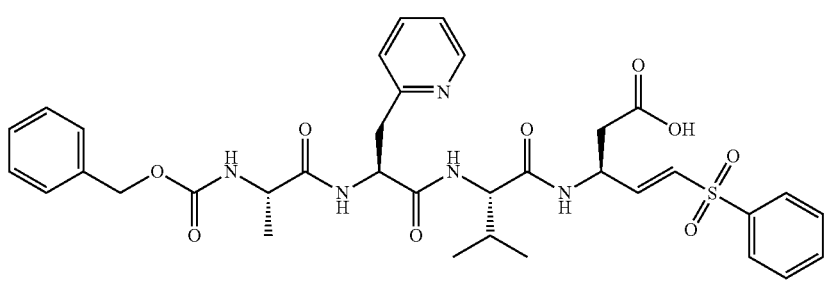 [SMILES: CC(C)[C@H](NC(=O)[C@H](Cc1ccccn1)NC(=O)[C@H](C)NC(=O)OCc1ccccc1)C(=O)N[C@H](/C=C/S(=O)(=O)c1ccccc1)CC(=O)O] |
| 86 | Z-Asp(O—tBu)-Trp-Val-OH | 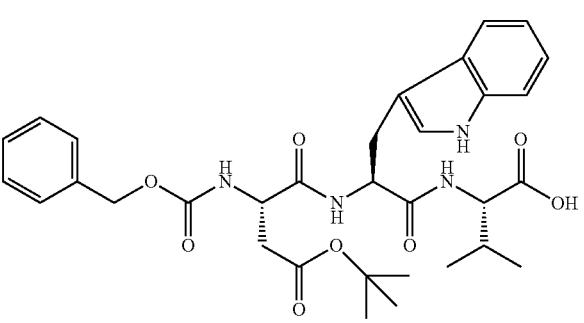 [SMILES: CC(C)[C@H](NC(=O)[C@H](Cc1c[nH]c2ccccc12)NC(=O)[C@H](CC(=O)OC(C)(C)C)NC(=O)OCc1ccccc1)C(=O)O] |
| 87 | Z-Asp(O—tBu)-Trp-Val-Asp(OtBu)methyl vinyl sulfone | 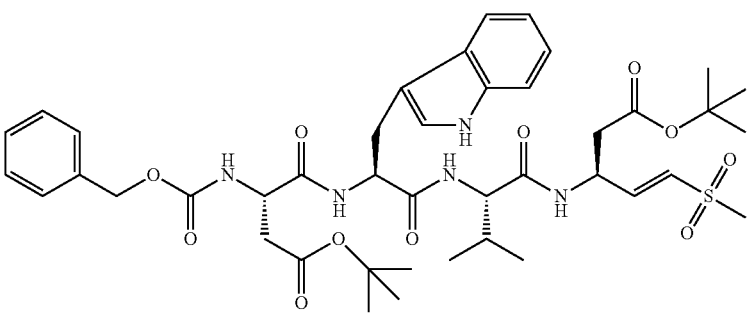 [SMILES: CC(C)[C@H](NC(=O)[C@H](Cc1c[nH]c2ccccc12)NC(=O)[C@H](CC(=O)OC(C)(C)C)NC(=O)OCc1ccccc1)C(=O)N[C@H](/C=C/S(C)(=O)=O)CC(=O)OC(C)(C)C] |

TABLE 1-continued

| CPD N° | CPD NAME |
|---|---|
| 88 | Z-Asp-Trp-Val-Aspmethyl vinyl sulfone |
| 89 | Boc-Asp(β-methyll) αchlorovinyl methylsulfone |
| 90 | Asp(β-methyll)αchlorovinyl methylsulfone tosyl salt |
| 91 | Boc-Asp(β-methyll) αmethoxyvinyl methylsulfone |
| 92 | Asp(β-methyll)αmethoxyvinyl methylsulfone tosyl salt |
| 93 | Aspmethyl vinyl sulfone tosyl salt |

TABLE 1-continued

| CPD N° | CPD NAME | STRUCTURE |
|---|---|---|
| 94 | Z-Tyr(OtBu)-Val-Ala-OH | 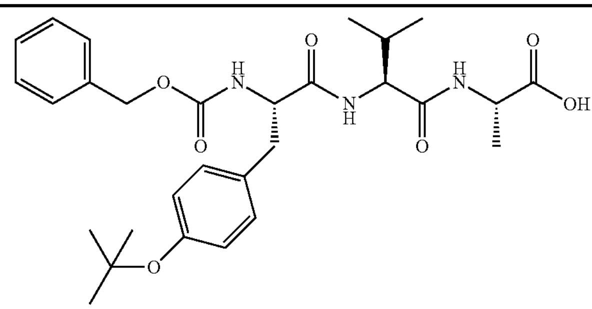 |
| 95 | Z-Tyr(OtBu)-Val-Ala-Asp(OtBu)phenyl vinyl sulfone | 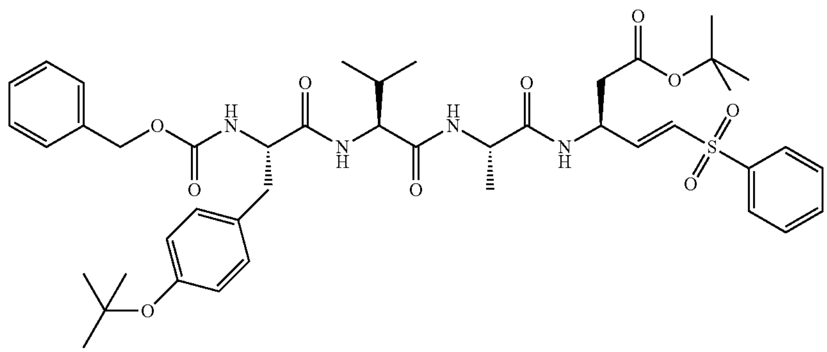 [SMILES: CC(C)[C@H](NC(=O)[C@H](Cc1ccc(OC(C)(C)C)cc1)NC(=O)OCc1ccccc1)C(=O)N[C@@H](C)C(=O)N[C@H](/C=C/S(=O)(=O)c1ccccc1)CC(=O)OC(C)(C)C] |
| 96 | Z-Tyr-Val-Ala-Asp phenyl vinyl sulfone | 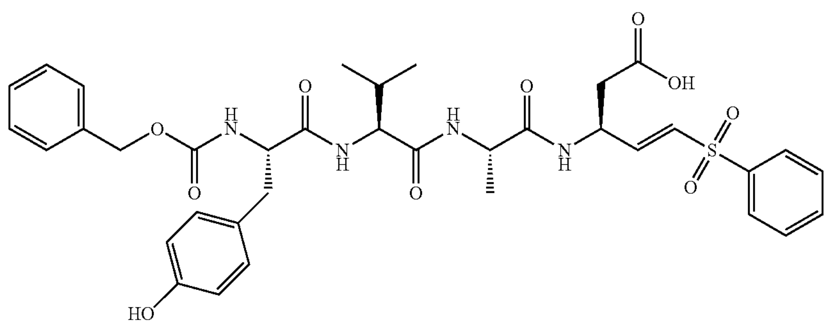 [SMILES: CC(C)[C@H](NC(=O)[C@H](Cc1ccc(O)cc1)NC(=O)OCc1ccccc1)C(=O)N[C@@H](C)C(=O)N[C@H](/C=C/S(=O)(=O)c1ccccc1)CC(=O)O] |

DEFINITIONS

Unless otherwise specified, the following definitions apply:

The singular forms "a", "an" and "the" include corresponding plural references unless the context clearly dictates otherwise.

As used herein, the term "comprising" is intended to mean that the list of elements following the word "comprising" are required or mandatory but that other elements are optional and may or may not be present.

As used herein, the term "consisting of" is intended to mean including and limited to whatever follows the phrase "consisting of". Thus the phrase "consisting of" indicates that the listed elements are required or mandatory and that no other elements may be present.

As used herein, the term "alkyl" is intended to include both branched and straight chain saturated aliphatic hydrocarbon groups having the specified number of carbon atoms, for example, $C_1$-$C_6$ as in $C_1$-$C_6$— alkyl is defined as including groups having 1, 2, 3, 4, 5 or 6 carbons in a linear or branched arrangement. Examples of $C_1$-$C_6$-alkyl and $C_1$-$C_4$ alkyl as defined above include, but are not limited to, methyl, ethyl, n-propyl, i-propyl, n-butyl, t-butyl, i-butyl, pentyl and hexyl.

As used herein, the term, "alkenyl" is intended to mean unsaturated straight or branched chain hydrocarbon groups having the specified number of carbon atoms therein, and in which at least two of the carbon atoms are bonded to each other by a double bond, and having either E or Z regiochemistry and combinations thereof. For example, $C_2$-$C_6$ as in $C_2$-$C_6$ alkenyl is defined as including groups having 1, 2, 3, 4, 5, or 6 carbons in a linear or branched arrangement, at least two of the carbon atoms being bonded together by a double bond. Examples of $C_2$-$C_6$ alkenyl include ethenyl (vinyl), 1-propenyl, 2-propenyl, 1-butenyl and the like.

As used herein, the term "cycloalkyl" is intended to mean a monocyclic saturated aliphatic hydrocarbon group having the specified number of carbon atoms therein, for example, $C_3$-$C_7$ as in $C_3$-$C_7$ cycloalkyl is defined as including groups having 3, 4, 5, 6, or 7 carbons in a monocyclic arrangement. Examples of $C_3$-$C_7$ cycloalkyl as defined above include, but are not limited to, cyclopropyl, cyclobutyl, cyclopentyl, cyclohexyl and cycloheptyl.

As used herein, the term "halo" or "halogen" is intended to mean fluorine, chlorine, bromine and iodine.

As used herein, the term "haloalkyl" is intended to mean an alkyl as defined above, in which each hydrogen atom may be successively replaced by a halogen atom. Examples of haloalkyls include, but are not limited to, $CH_2F$, $CHF_2$ and $CF_3$.

As used herein, the term "aryl", either alone or in combination with another radical, means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, 1-naphthyl, 2-naphthyl and tetrahydronaphthyl. The aryls may be connected to another group either at a suitable position on the cycloalkyl ring or the aromatic ring.

As used herein, the term "heteroaryl" is intended to mean a monocyclic or bicyclic ring system of up to ten atoms, wherein at least one ring is aromatic, and contains from 1 to 4 hetero atoms selected from the group consisting of O, N, and S. The heteroaryl substituent may be attached either via a ring carbon atom or one of the heteroatoms. Examples of heteroaryl groups include, but are not limited to thienyl, benzimidazolyl, benzo[b]thienyl, furyl, benzofuranyl, pyranyl, isobenzofuranyl, chromenyl, xanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, napthyridinyl, quinoxalinyl, quinazolinyl, cinnolinyl, pteridinyl, isothiazolyl, isochromanyl, chromanyl, isoxazolyl, furazanyl, indolinyl, isoindolinyl, thiazolo[4,5-b]-pyridine, and fluoroscein derivatives.

As used herein, the term "heterocycle", "heterocyclic" or "heterocyclyl" is intended to mean a 5, 6, or 7 membered non-aromatic ring system containing from 1 to 4 heteroatoms selected from the group consisting of O, N and S. Examples of heterocycles include, but are not limited to pyrrolidinyl, tetrahydrofuranyl, piperidyl, pyrrolinyl, piperazinyl, imidazolidinyl, morpholinyl, imidazolinyl, pyrazolidinyl, and pyrazolinyl.

As used herein, the term "electron withdrawing group (EWG)" is intended to mean a functional group that allows nucleophilic attack by the thiol-group of a caspase at the alkene bond of the inhibitor as a result of the electron withdrawing properties of the EWG. The EWG is conjugated with the alkene bond, such that the electron withdrawing properties of the EWG allow nucleophilic attack by a caspase at the alkene bond, i.e. the alkene bond and the EWG are electronically conjugated. Thus, the covalent bond between the alkene bond and the EWG is a direct one, without intervening moieties that would prevent the electron withdrawing properties of the EWG from being exerted on the alkene bond.

As used herein, the term "detectable label" is intended to mean a group that may be linked to a compound of the present invention to produce a probe or to a caspase, such that when the probe is associated with the caspase, the label allows either direct or indirect recognition of the probe so that it may be detected, measured and quantified.

As used herein, the term "affinity tag" is intended to mean a ligand or group, which is linked to either a compound of the present invention or to a caspase to allow another compound to be extracted from a solution to which the ligand or group is attached.

As used herein, the term "probe" is intended to mean a compound of Formula I, IA, II, IIA, III, or IIIA, which is labeled with either a detectable label or an affinity tag, and which is capable of binding, either covalently or non-covalently, to a caspase. When, for example, the probe is non-covalently bound, it may be displaced by a test compound. When, for example, the probe is bound covalently, it may be used to form cross-linked adducts, which may be quantified and inhibited by a test compound.

As used herein, the term "optionally substituted with one or more substituents" or its equivalent term "optionally substituted with at least one substituent" is intended to mean that the subsequently described event of circumstances may or may not occur, and that the description includes instances where the event or circumstance occurs and instances in which it does not. The definition is intended to mean from zero to five substituents.

If the substituents themselves are incompatible with the synthetic methods of the present invention, the substituent may be protected with a suitable protecting group (PG) that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, Protecting Groups in Chemical Synthesis (3$^{rd}$ ed.), John Wiley & Sons, NY (1999), which is incorporated herein by reference in its entirety. Examples of protecting groups used throughout include, but are not limited to Fmoc, Bn, Boc, CBz and COCF$_3$. In some instances, a substituent may be specifically selected to be reactive under the reaction conditions used in the methods of this invention. Under these circumstances, the reaction conditions convert the selected substituent into another substituent that is either useful in an intermediate compound in the methods of this invention or is a desired substituent in a target compound.

Three and single letter abbreviations for □-amino acids used throughout are as follows:

| Amino acid | Abbreviation | Abbreviation |
| --- | --- | --- |
| □-Amino butyric acid | Abu | — |
| Alanine | Ala | A |
| Arginine | Arg | R |
| Aspartic acid | Asp | D |
| Asparagine | Asn | N |
| Cysteine | Cys | C |
| Glutamic acid | Glu | E |
| Glutamine | Gln | Q |
| Glycine | Gly | G |
| Isoleucine | Ile | I |
| Histidine | His | H |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A series of non natural amino acids which may be used in place of natural amino acids is but not limited to 3-amino 2-hydroxy pyridine; (2furyl)alanine; 1 amino 1 cyclohexane carboxylic acid; (2-thienyl)alanine; 2-Aminobenzoic acid (2-Abz); 2PyridylAlanine; 1Amino 1Cyclopentanecarboxilic acid; 2-Aminobutyric acid (2Abu); 3-Amino-3-phenyl-propionic acid; Aminocyclopentane carboxylic acid (ACPC); 4-Aminomethylbenzoic acid (Amb); Aminoisobutiric acid (Aib); p-Benzoyl-1-phenylalanine (Bpa); Allyl- Glycine; 4-Aminomethyl cyclohexane carboxylic acid (Amc); Cyclohexyl-alanine (Cha); deltaValine; deltaLeucine; Cyanobbutylalanine (Cba); Indanylglycine (IgI); 3-(2-naphthyl)alanine (1-NaI); Biphenylalanine (Bip); Hydroxyproline (Hyp); Isonipecotic acid (Inp); Norvaline (Nva); 4-Iodophenylalanine (Phe(pI)); 4-nitroPhenylalanine; 4-MethylPhenylalanine; 4-MethylPhealanine; Homophenylalanine (hPhe); 4-aminophenylalanine (Phe4NH(Boc); phenyl glycine; Pipecolic acid (Pip); propargylglycine; Thioproline (Thz); ButylGlycine (Tle); 3-NitroTyrosine.

As used herein, the term "residue" when referring to □-amino acids is intended to mean a radical derived from the corresponding □-amino acid by eliminating the hydroxyl of the carboxy group and one hydrogen of the □-amino group. For example, the terms Gln, Ala, Gly, Ile, Arg, Asp, Phe, Ser, Leu, Cys, Asn, and Tyr represent the residues of L-glutamine, L-alanine, glycine, L-isoleucine, L-arginine, L-aspartic acid, L-phenylalanine, L-serine, L-leucine, L-cysteine, L-asparagine, and L-tyrosine, respectively.

As used herein the term "amino acid side chain" is intended to mean the part of an amino acid's chemistry that differentiates it from other amino acids. Amino acid structure includes a carboxyl group, an amine group plus the individual side chain. Each amino acid has a unique side chain. This is applied to unnatural amino acids as well. This side chain may exist in protected form or not.

As used herein, the term "prodrug" is intended to mean a compound that may be converted under physiological conditions or by solvolysis to a biologically active compound of the present invention. Thus, the term "prodrug" refers to a precursor of a compound of the invention that is pharmaceutically acceptable. A prodrug may be inactive or display limited activity when administered to a subject in need thereof, but is converted in vivo to an active compound of the present invention. Typically, prodrugs are transformed in vivo to yield the compound of the invention, for example, by hydrolysis in blood or other organs by enzymatic processing. The prodrug compound often offers advantages of solubility, tissue compatibility or delayed release in the subject (see, Bundgard, H., Design of Prodrugs (1985), pp. 7-9, 21-24 (Elsevier, Amsterdam). The definition of prodrug includes any covalently bonded carriers which release the active compound of the invention in vivo when such prodrug is administered to a subject. Prodrugs of a compound of the present invention may be prepared by modifying functional groups present in the compound of the invention in such a way that the modifications are cleaved, either in routine manipulation or in vivo, to a parent compound of the invention.

As used herein, the term "pharmaceutically acceptable salt" is intended to mean both acid and base addition salts.

As used herein, the term "pharmaceutically acceptable acid addition salt" is intended to mean those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

As used herein, the term "pharmaceutically acceptable base addition salt" is intended to mean those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

The compounds of the present invention, or their pharmaceutically acceptable salts may contain one or more asymmetric centers, chiral axes and chiral planes and may thus give rise to enantiomers, diastereomers, and other stereoisomeric forms and may be defined in terms of absolute stereochemistry, such as (R)- or (S)- or, as (D)- or (L)- for amino acids. The present invention is intended to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. The racemic mixtures may be prepared and thereafter separated into individual optical isomers or these optical isomers may be prepared by chiral synthesis. The enantiomers may be resolved by methods known to those skilled in the art, for example by formation of diastereoisomeric salts which may then be separated by crystallization, gas-liquid or liquid chromatography, selective reaction of one enantiomer with an enantiomer specific reagent. It will also be appreciated by those skilled in the art that where the desired enantiomer is converted into another chemical entity by a separation technique, an additional step is then required to form the desired enantiomeric form. Alternatively specific enantiomers may be synthesized by asymmetric synthesis using optically active reagents, substrates, catalysts, or solvents or by converting one enantiomer to another by asymmetric transformation.

Certain compounds of the present invention may exist as a mix of epimers. Epimers means diastereoisomers that have the opposite configuration at only one of two or more stereogenic centres present in the respective compound.

Certain compounds of the present invention may exist in Zwitterionic form and the present invention includes Zwitterionic forms of these compounds and mixtures thereof.

In addition, the compounds of the invention also may exist in hydrated and anhydrous forms. Hydrates of the compound of any of the formulas described herein are included as compounds of the invention. In a further embodiment, the compound according to any of the formulas described herein is a monohydrate. In one embodiment, the compound of the invention comprises about 10% or less, about 9% or less, about 8% or less, about 7% or less, about 6% or less, about 5% or less, about 4% or less, about 3% or less, about 2% or less, about 1% or less, about 0.5% or less, about 0.1% or less by weight of water. In another embodiment, the compounds of the invention comprise, about 0.1% or more, about 0.5% or more, about 1% or more, about 2% or more, about 3% or more, about 4% or more, about 5% or more, or about 6% or more by weight of water.

C) Methods of Preparation

General methods for the synthesis of the compounds of the present invention are shown below and are disclosed merely for the purpose of illustration and are not meant to be interpreted as limiting the processes to make the compounds by any other methods.

Those skilled in the art will readily appreciate that a number of methods are available for the preparation of the compounds of the present invention.

The starting materials and reagents used in preparing these compounds are either available from commercial suppliers such as Sigma-Aldrich Chemicals, Anaspec or chemipex.

The starting materials and the intermediates of the reaction may be isolated and purified if desired using conventional techniques such chromatography (Biotage flash chromatography), filtration, distillation, etc. Such materials can be characterized using conventional analytical methods such as NMR and LCMS.

The coupling step is carried out in the presence of a suitable coupling agent such as, but not limited to, diisopropyl carbodiimide (DPC), anhydride mixture (isobutyl-chloroformate), O-benzotriazole-1-yloxytrispyrrolidino-phosphonium hexafluorophosphate(PyBOP), O-benzotriazol-1-yl-N,N,N,N tetramethyluronium-hexafluoro-phosphate (HBTU), O-(7-azabenzotriazol-1-yl)-1,1,3,3-tetramethyluronium hexafluoro-phosphate (HATU), 1-hydroxybenzotriazole (HOBT) in the presence of 1-(3-dimethylaminopropyl)-3-ethylcarbodiimide hydrochloride (EDC). A base such as N,N-diisopropylethylamine, triethyl amine, or N-methylmorpholine. The reaction is carried out at 20° C. except for anhydride mix formation (isobutyl chloroformate, −5/−13° C.) to avoid any racemisation of amino acids.

Removal of the amino protecting group is carried out but by piperidine in dichloromethane (Fmoc protecting group). The removal of β-tert-butyl carboxylic acid is carried out by TFA. Selective removal of N-Boc from B-tert butyl aspartic acid is carried out by PTSA or TFA at 0° C.

Vinyl sulfone function is elucidated as an example only in the following examples, but is not limited to it. It will be recognized by a skilled person in the art, that other vinyl electron-withdrawing group (EWG) may be used in this invention. Benzyloxycarbonyl (Z) is elucidated as an example of linkers that may facilitate the penetration of the drug into cells. It is recognized that other X—R3 may be used as well. The allyl group was introduced directly by the use of commercially available $AA_2$-OAllyl protected form or synthesized from the corresponding amino acid $AA_2$-OH.

This is a convergent synthesis, which consists of synthesizing two different fragments (suicide inhibitor linker and the peptide or peptidomimetic fragment) prior to the 'coupling step'.

A Compound of Formula 1a can be Prepared by the Procedure Described Below

Formula 1a

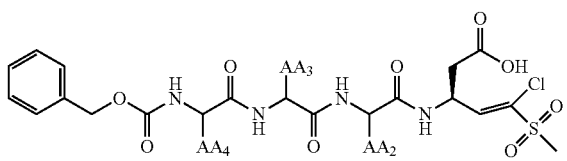

Left Arm Synthesis:

The allyl group was introduced directly by the use of commercially available $AA_2$-OAllyl protected form or synthesized from the protected amino acid fmoc-$AA_2$-OH and allyl alcohol (EDC, DMAPcat, NMM, $CH_2Cl_2$/DMF (5/1)) followed with fmoc deprotection (piperidine, $CH_2Cl_2$).

The $AA_2$-OAllyl is coupled to Fmoc-$AA_3$-OH with the coupling reagent 1-(3-dimethylaminopropyl)-3-ethylcarbodiimide hydrochloride (EDC) and subsequent fmoc deprotection with piperidine gives $AA_3$-$AA_2$-Oallyl (intermediate A) ready for coupling with (Z) $AA_4$-OH gave (Z) $AA_4$-$AA_3$-$AA_2$-Oallyl (intermediate B) which upon removal of allyl group (tetrakis) liberate the C-terminal carboxylic acid (tripeptide A) as described in the following scheme.

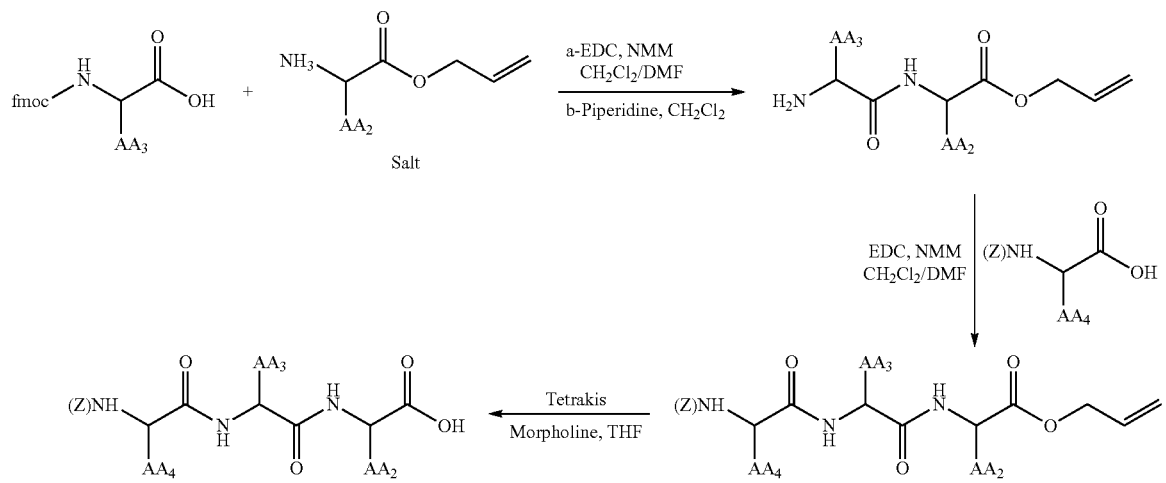

Right Arm Synthesis

The suicide substrate proposed in the following scheme is Asp α-chlorovinyl methylsulfone.

The common intermediate Boc-Asp(B-tert-butyl)-His synthesized from Boc-Asp (B-tert-butyl)-N-hydroxysuccinimide ester as reported by (Mancuso A et al., 1981, William R. Ewing et al., 1999 and Won Bum Jang. 2004).

Treatment of the aldehyde with sodium anion of Diethyl chloro(methylsulfone)methylphosphonate results in the corresponding Boc-Asp (β-tert-butyl) α-chlorovinyl-methylsulfone in the manner of Wadsworth and Emmons.

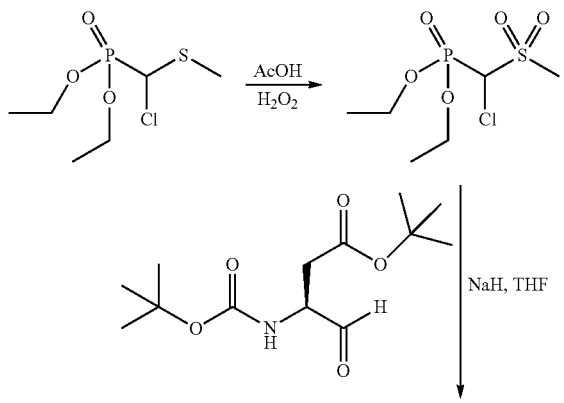
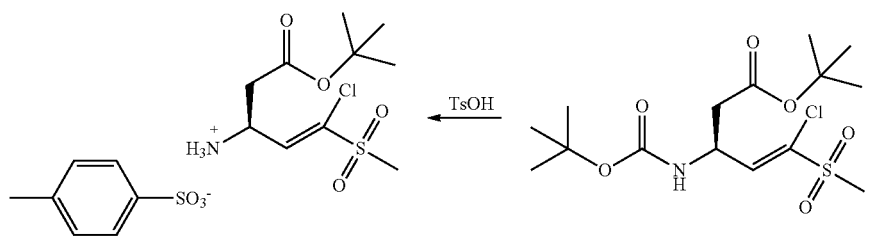
Coupling Step Synthesis
The coupling step between Asp α chlorovinyl methylsulfone salt and the peptide in the presence of coupling reagents such (isobutyl chloroformate, NMM) or (HOBT, NMM, EDC; Dragovich P., S., 1999) results in Asp α-chlorovinyl methylsulfone peptide derivative.
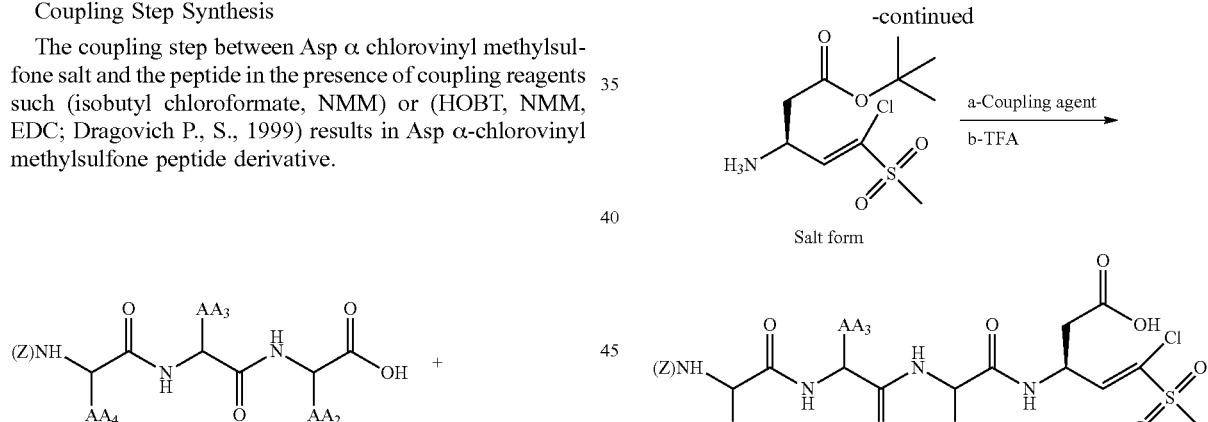
A Compound of Formula 1b can be Prepared by the Procedure Described Below
Formula 1b
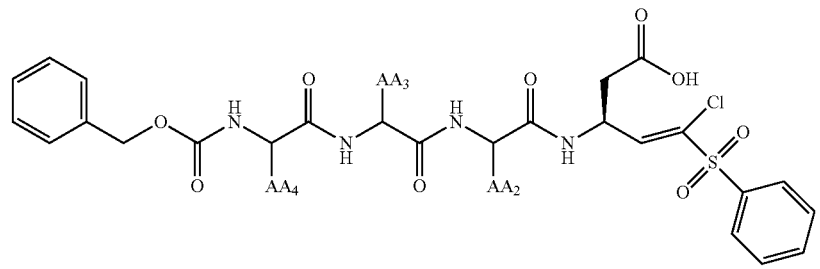

Right Arm Synthesis

The suicide substrate proposed in the following scheme is Asp α-chlorovinyl phenylsulfone.

Treatment of the aldehyde with sodium anion of Diethyl chloro(methylsulfone)phenyl phosphonate results in the corresponding Boc-Asp (β-tert-butyl) α-chlorovinyl phenylsulfone in the manner of Wadsworth and Emmons.

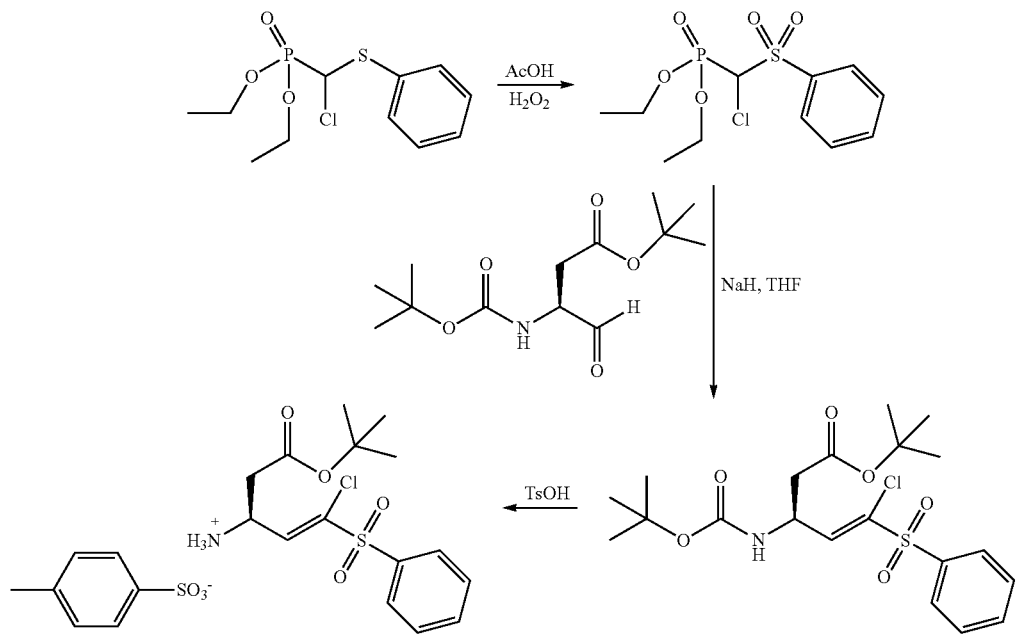

Coupling Step Synthesis

The coupling step between Asp α-chlorovinyl phenylsulfone salt and the peptide in the presence of coupling reagents such (isobutyl chloroformate, NMM) or (HOBT, NMM, EDC) results in Asp α-chlorovinyl phenylsulfone peptide derivative.

A Compound of Formula 1c can be Prepared by the Procedure Described Below

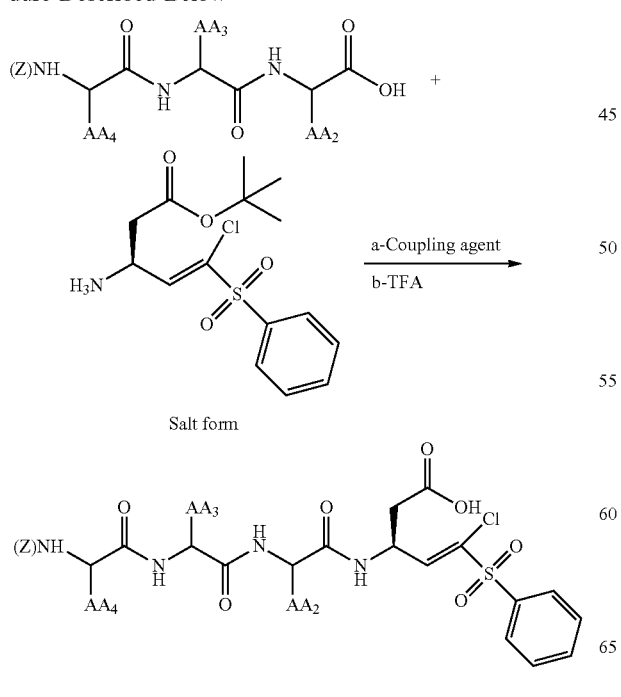

-continued

Formula 1c

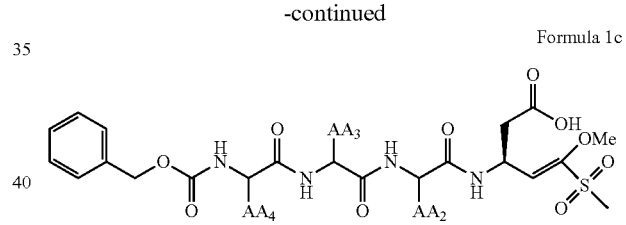

Right Arm Synthesis

The suicide substrate proposed in the following scheme is Asp β-methoxyvinyl methylsulfone.

Oxydation of diethyl methylthiomethylphosphonate include anodic oxidation in NaOMe/MeOH (saturated with $CO_2$) to give the O, S-acetal of diethoxyphosphinylformaldehyde, which upon oxidation may give the corresponding sulfone as Diethyl methoxy(methylsulfone)phenyl phosphonate (Shankaran, K et al. 2001).

Treatment of the aldehyde with sodium anion of Diethyl methoxy (methylsulfone)phenyl phosphonate should result in the corresponding Boc-Asp (β-tert-butyl) α-methoxyvinyl methylsulfone in the manner of Wadsworth and Emmons.

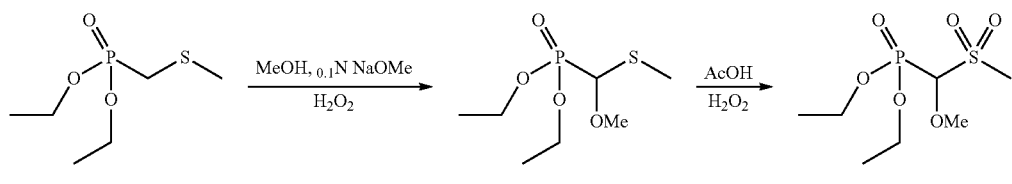

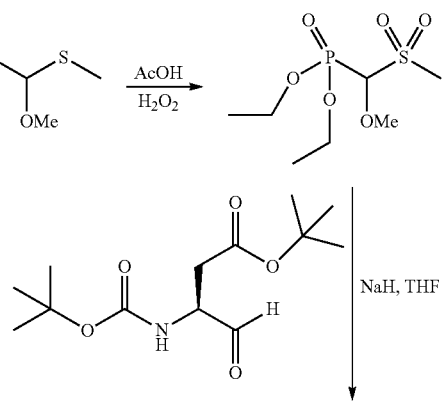

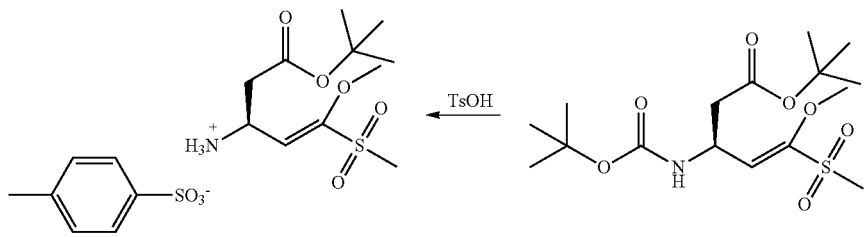

Coupling Step Synthesis

The coupling step between Asp α-methoxyvinyl methylsulfone salt and the peptide in the presence of coupling reagents such (isobutyl chloroformate, NMM) or (HOBT, NMM, EDC) results in Asp α-methoxyvinyl methylsulfone peptide derivative.

A Compound of Formula 1d can be Prepared by the Procedure Described Below

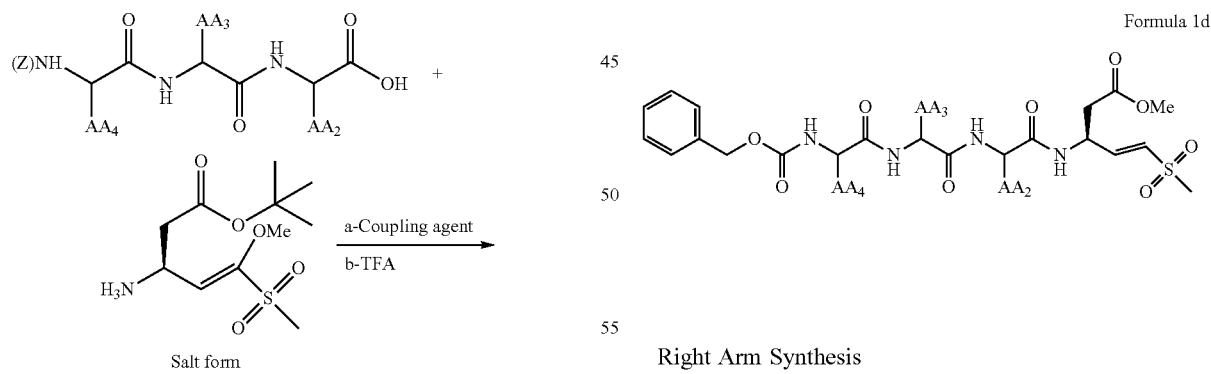

Formula 1d

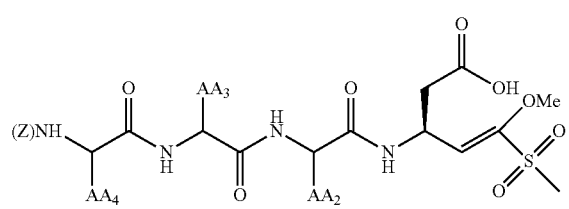

Right Arm Synthesis

The suicide substrate proposed in the following scheme is Asp(B-Methyl)methyl vinylsulfone.

Boc-Asp(B-Methyl)-N-hydroxysuccinimide ester was reduced to the corresponding alcohol (NaBH$_4$, THF), a subsequent oxidation (oxalyl chloride, DMSO) gave the aldehyde: Boc-Asp(B-Methyl)-H.

Treatment of Boc-Asp(B-Methyl)-H with sodium anion of Diethyl (methylsulfone) methyl phosphonate results in the corresponding Boc-Asp (β-Methyl)methyl vinylsulfone in the manner of Wadsworth and Emmons.

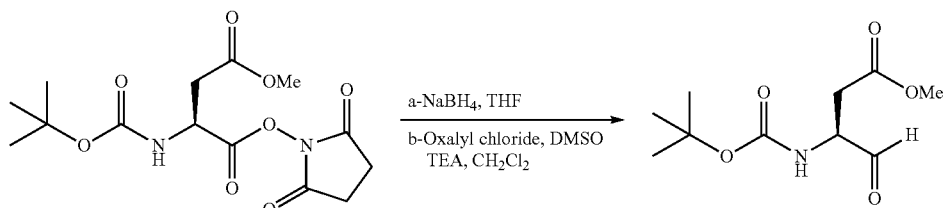

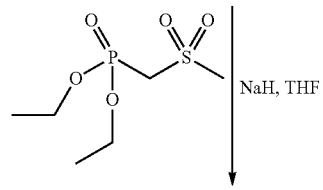

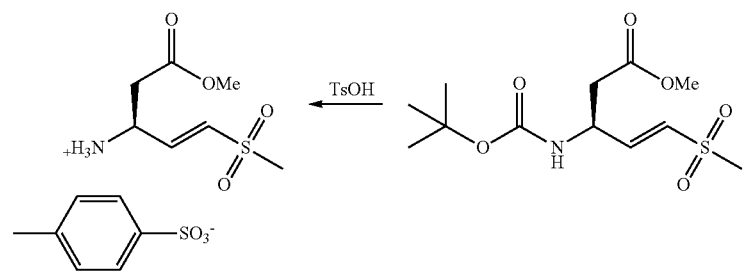

Coupling Step Synthesis

The coupling step between Asp (β-Methyl)methyl vinylsulfone salt and the peptide in the presence of coupling reagents such (isobutyl chloroformate, NMM) or (HOBT, NMM, EDC) results in Asp (β-Methyl)methyl vinylsulfone peptide derivative.

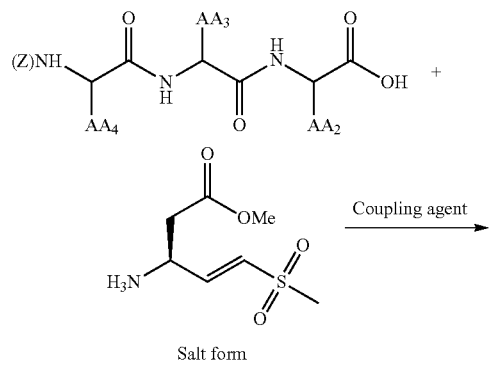

A Compound of Formula 1e can be Prepared by the Procedure Described Below

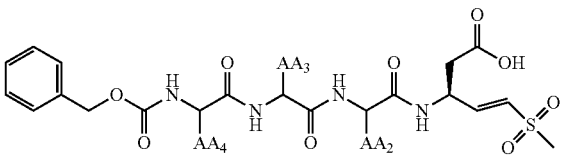

Formula 1e

Right Arm Synthesis

The suicide substrate proposed in the following scheme is Asp methyl vinyllsulfone.

The common intermediate Boc-Asp(B-tert-butyl)-His synthesized from Boc-Asp(B-tert-butyl)-N-hydroxysuccinimide ester as reported by (Mancuso A et al., 1981, William R. Ewing et al., 1999 and Won Bum Jang. 2004).

Treatment of the aldehyde with sodium anion of Diethyl (methylsulfone) methyl phosphonate results in the corresponding Boc-Asp (β-tert-butyl)methylvinylsulfone in the manner of Wadsworth and Emmons, 1961 and Palmer et al. 1995.

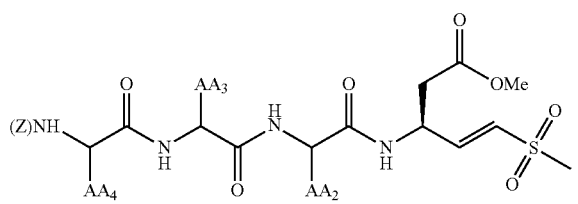

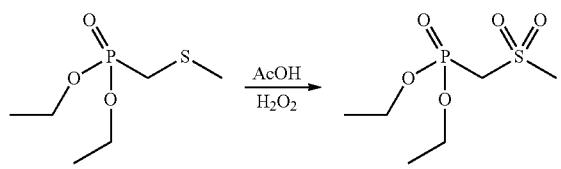

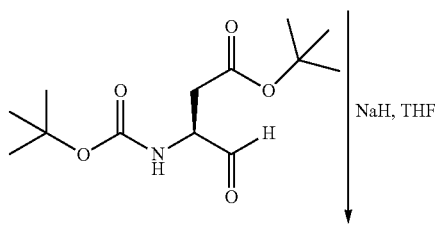

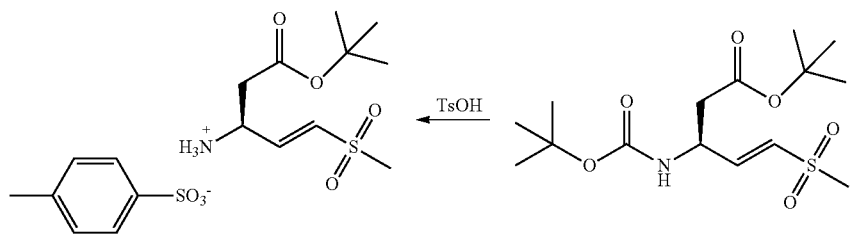

Coupling Step Synthesis

The coupling step between Asp methyl vinylsulfone salt and the peptide in the presence of coupling reagents such (isobutyl chloroformate, NMM) or (HOBT, NMM, EDC) results in Asp methyl vinylsulfone peptide derivative.

A Compound of Formula 1f can be Prepared by the Procedure Described Below

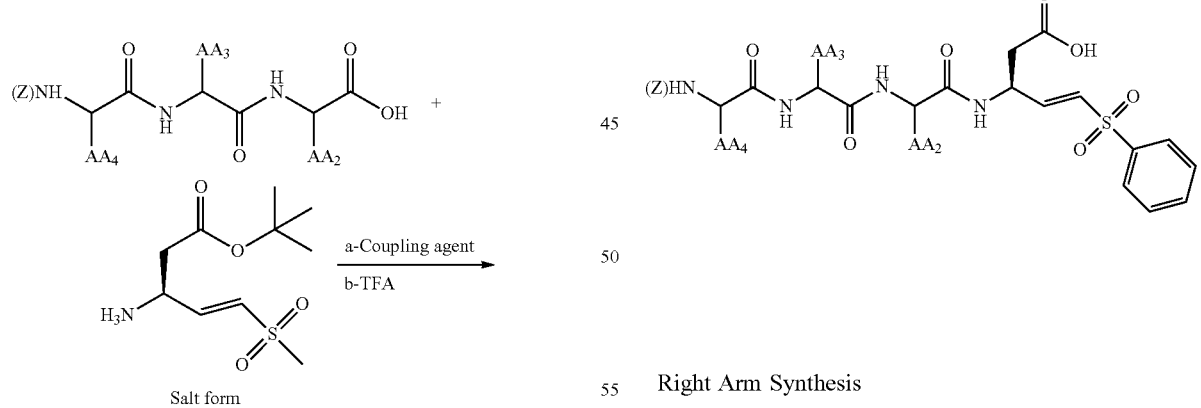

Formula 1f

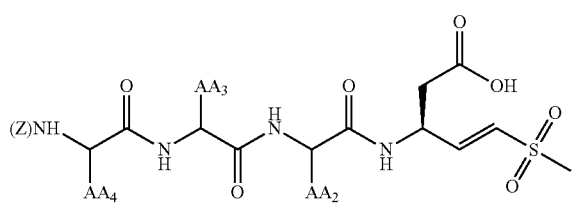

Right Arm Synthesis

The suicide substrate proposed in the following scheme is Asp phenyl vinyllsulfone.

Diethyl phenylsulfonylmethylphosphonate was obtained in one step from benzenesulfonyl fluoride and triethyl phosphorane in the presence of lithium hexamethyldisilazide (Won Bum Jang et al., 1998).

Treatment of the aldehyde with sodium anion of Diethyl (phenyl sulfone) methylphosphonate results in the corresponding Boc-Asp (β-tert-butyl)phenyl vinylsulfone in the manner of Wadsworth and Emmons, 1961 and Palmer et al. 1995.

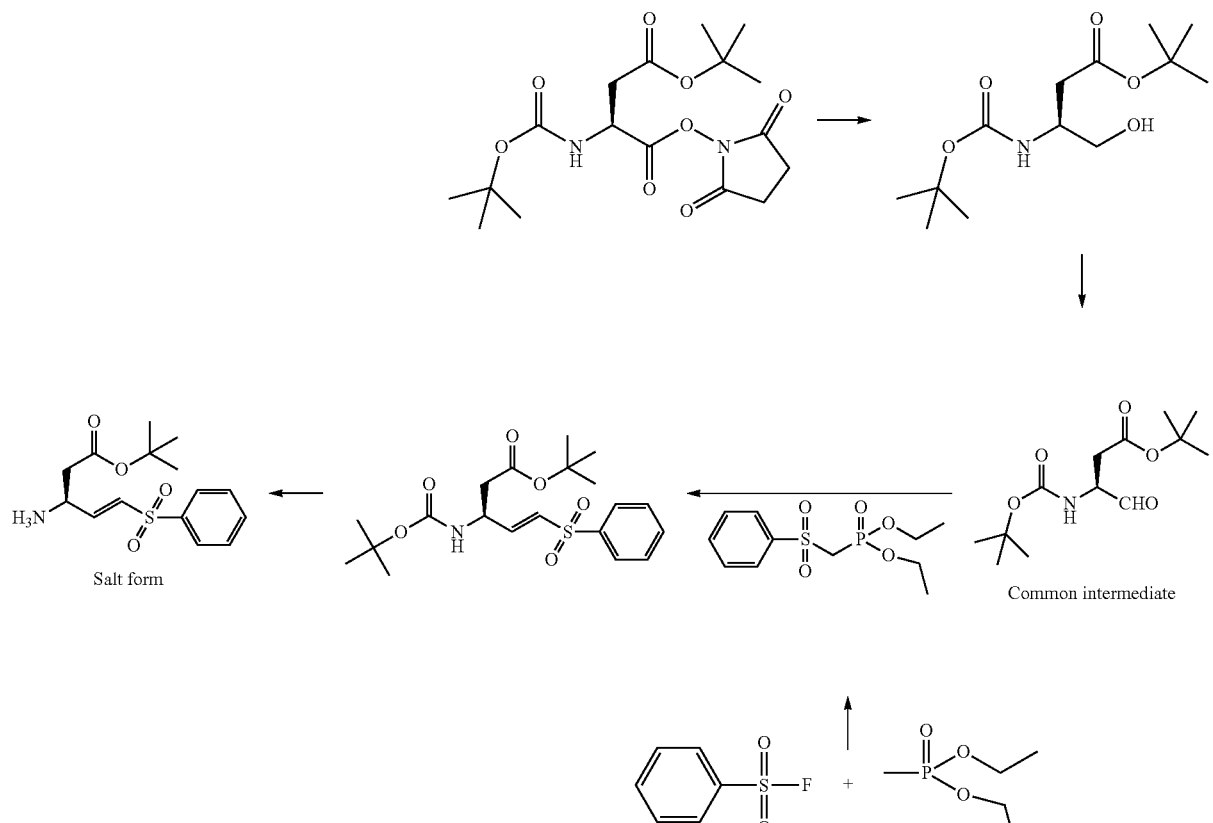
Common intermediate
Salt form
Coupling Step Synthesis
The coupling step between Asp phenyl vinylsulfone salt and the peptide in the presence of coupling reagents such (isobutyl chloroformate, NMM) or (HOBT, NMM, EDC) results in Asp phenyl vinylsulfone peptide derivative.
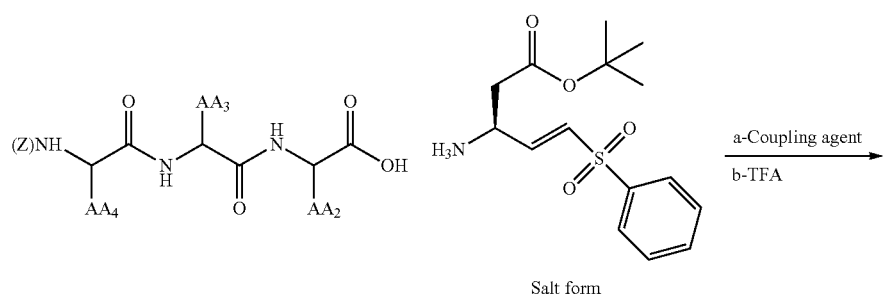
Salt form
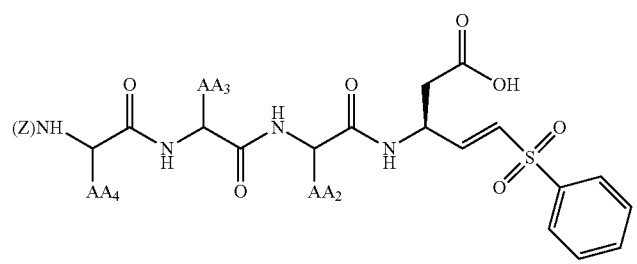

A Compound of Formula 1g can be Prepared by the Procedure Described Below

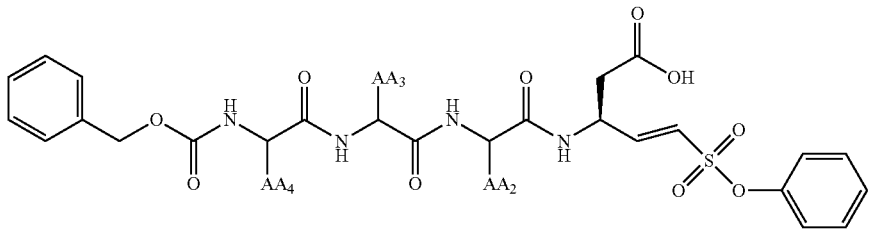

Formula 1g

Right Arm Synthesis

The suicide substrate proposed in the following scheme is Asp phenoxy vinyllsulfone.

Diethyl (phenoxysulfone) methylphosphonate was obtained from methanesulfonyl phenoxy and diethyl chlorophosphonate in the presence of potassium bis(trimethylsilyl)amide. A subsequent oxidation (AcOH, $H_2O_2$) gave the corresponding sulfone.

Treatment of the aldehyde with sodium anion of Diethyl (phenoxy sulfone) methylphosphonate results in the corresponding Boc-Asp (β-tert-butyl)phenoxy vinylsulfone in the manner of Wadsworth and Emmons.

Coupling Step Synthesis

The coupling step between Asp phenoxy vinylsulfone salt and the peptide in the presence of coupling reagents such (isobutyl chloroformate, NMM) or (HOBT, NMM, EDC) results in Asp phenoxy vinylsulfone peptide derivative.

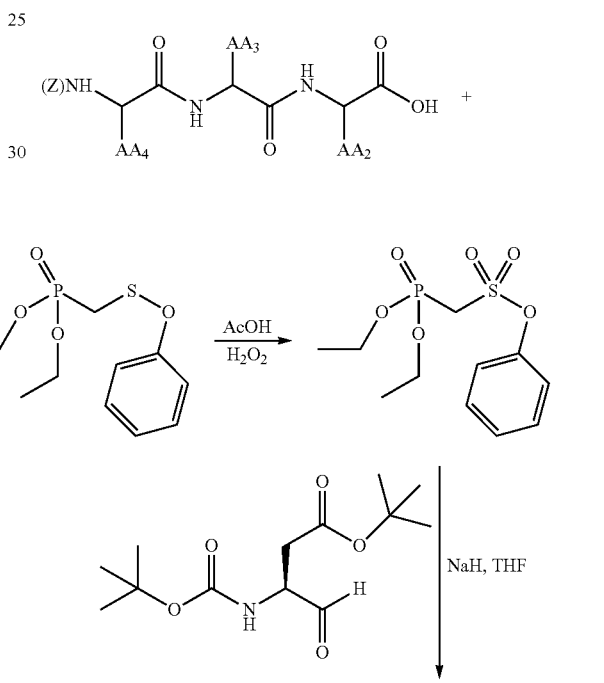

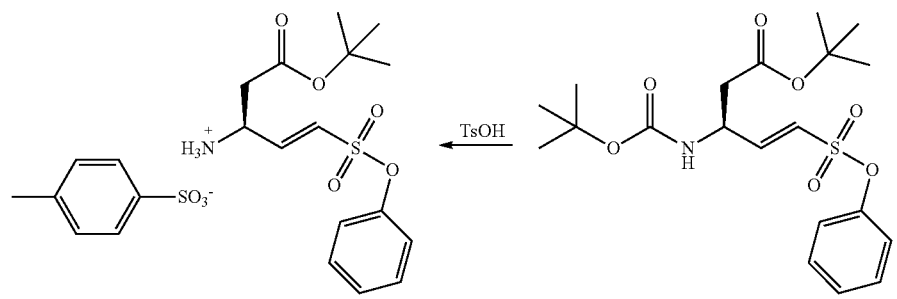

65
-continued

66
-continued

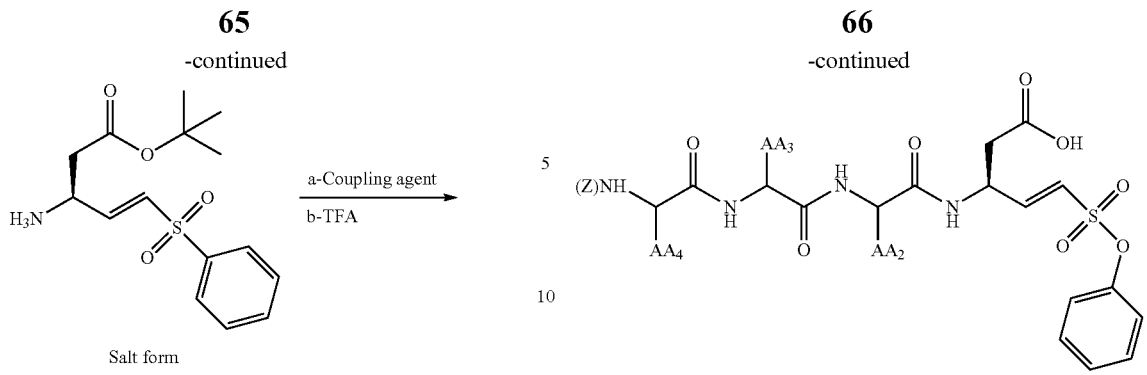

Salt form → a-Coupling agent, b-TFA →

A Compound of Formula 1h can be Prepared by the Procedure Described Below

Formula 1h

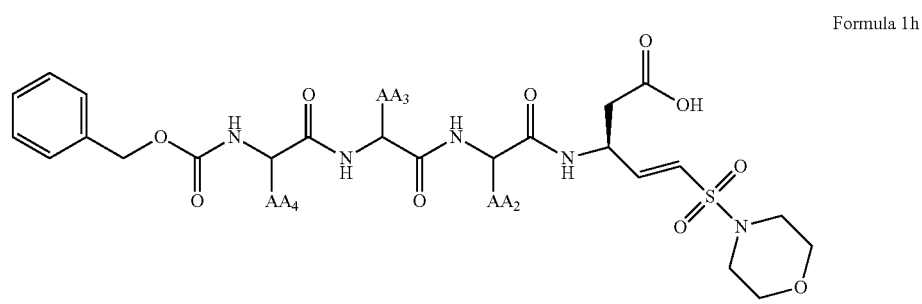

Right Arm Synthesis

The suicide substrate proposed in the following scheme is Asp morpholine vinyllsulfone.

Diethyl (morpholinesulfone) methylphosphonate was prepared from methane sulfonyl morpholine and chloromethylphosphonate in the presence of potassium bis(trimethylsilyl) amide.

Treatment of the aldehyde with sodium anion of Diethyl (morpholinesulfone) methylphosphonate results in the corresponding Boc-Asp (β-tert-butyl) morpholino vinylsulfone in the manner of Wadsworth and Emmons.

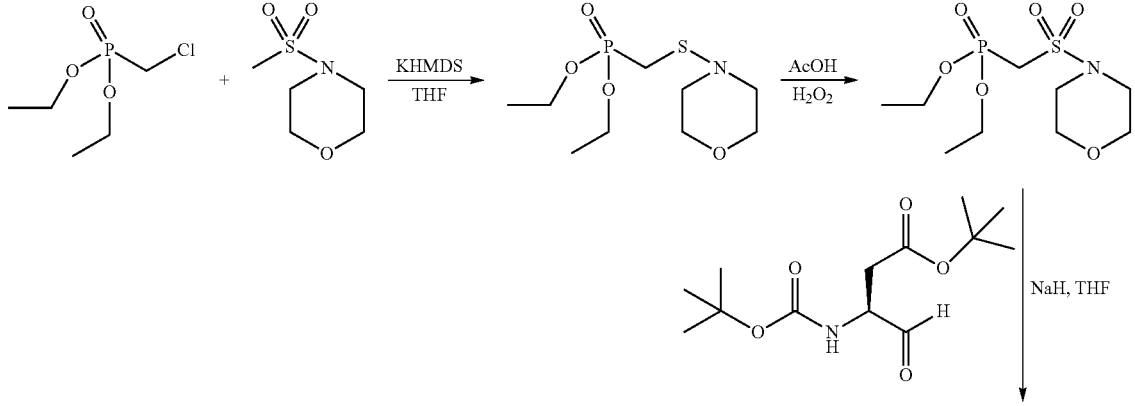

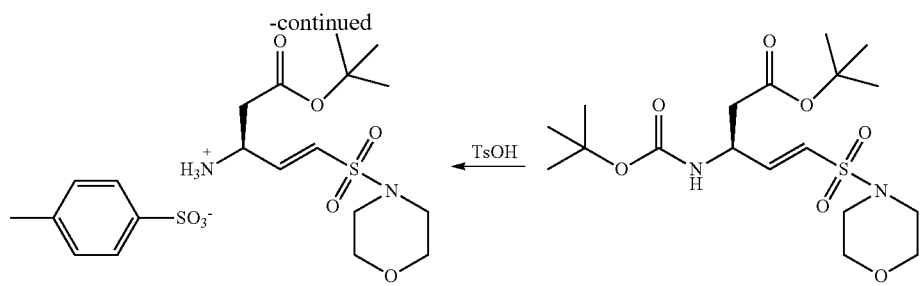
Coupling Step Synthesis
The coupling step between Asp morpholine vinylsulfone salt and the peptide in the presence of coupling reagents such (isobutyl chloroformate, NMM) or (HOBT, NMM, EDC) results in Asp morpholine vinylsulfone peptide derivative
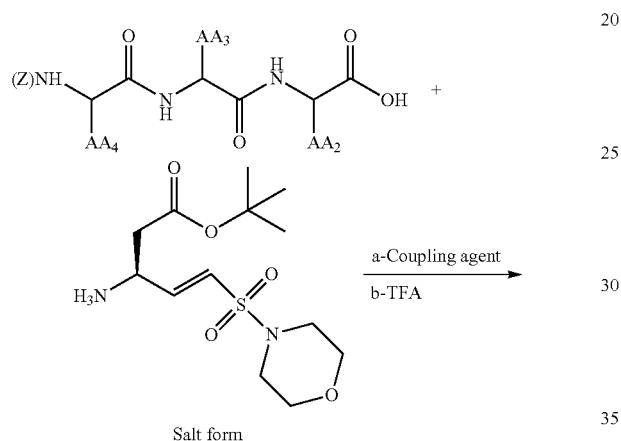
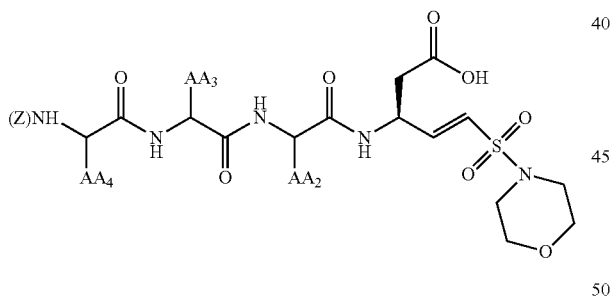
A Compound of Formula 1i can be Prepared by the Procedure Below
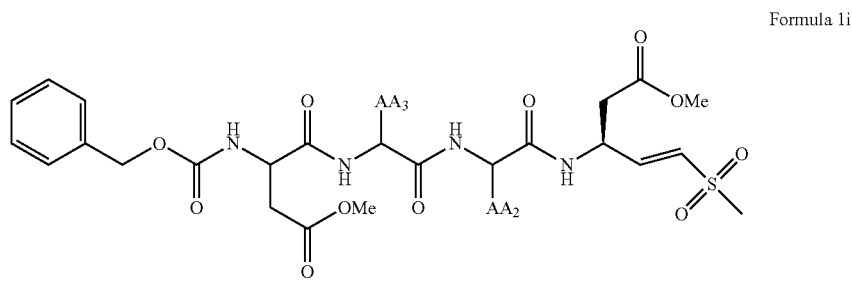
Formula 1i Right Arm Synthesis The suicide substrate proposed in the following scheme is Asp(B-Methyl)-vinylsulfone derivatives.

Boc-Asp(B-Methyl)-N-hydroxysuccinimide ester was reduced to the corresponding alcohol (NaBH₄, THF), a subsequent oxidation (oxalyl chloride, DMSO) gave the aldehyde Boc-Asp(B-Methyl)-H.

Treatment of Boc-Asp(B-Methyl)-H with sodium anion of Diethyl (methylsulfone) phosphonate derivatives results in the corresponding Boc-Asp (β-Methyl) vinylsulfone derivatives in the manner of Wadsworth and Emmons.

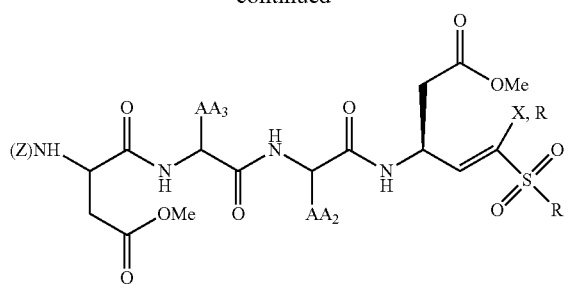

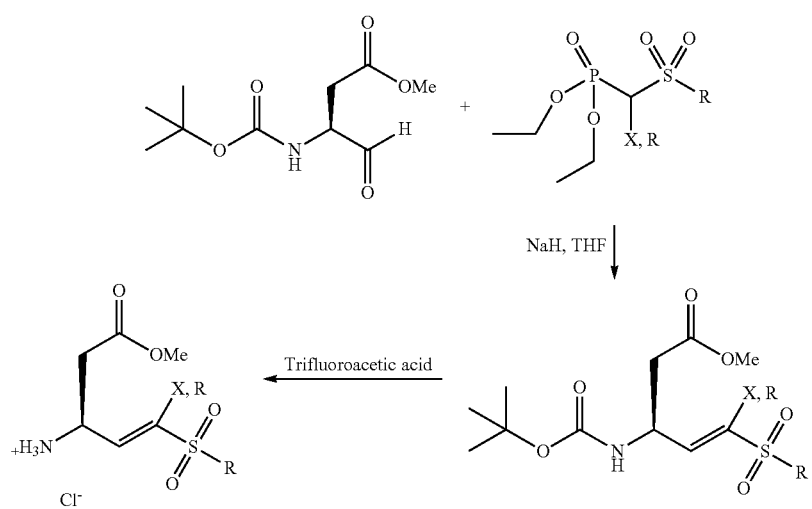

Coupling Step Synthesis

The coupling step between Asp (β-Methyl) vinylsulfone derivatives salt and the caspase-3 designed peptide in the presence of coupling reagents such (isobutyl chloroformate, NMM) or (HOBT, NMM, EDC) results in Z-Asp(β-Methyl)-AA₃-AA₂-Asp (β-Methyl) vinylsulfone peptide derivatives.

This approach will allow the synthesis of a variety of pro-drug vinylsulfone derivatives that could be easily obtained by choosing the appropriate combination (X, R) and applying the appropriate method mentioned above. Such combination may enhance cell permeability, selectivity and potency.

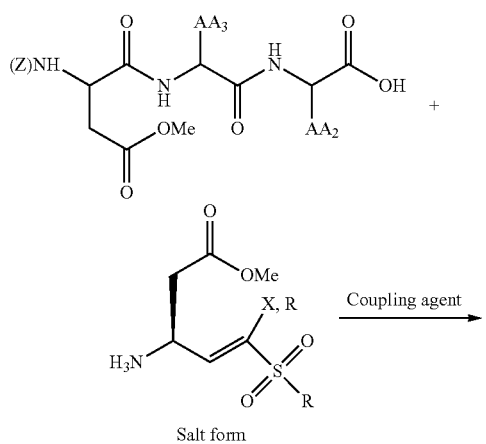

All acid, salt and other ionic and non-ionic forms of the compounds described are included as compounds of the invention. For example, if a compound is shown as an acid herein, the salt forms of the compound are also included. Likewise, if a compound is shown as a salt and the acid forms are also included.

In certain embodiments, the compounds of the present invention are represented by generalized Formula I, IA, II, IIA, III, or IIIA, or a pharmaceutically acceptable salt and/or prodrug thereof:

D) Development of specific Caspase Inhibitors

An additional aspect of the invention relates to a method for designing caspase inhibitors. Following the same approach as outlined hereinafter, those skilled in the art will appreciate that it is conceivable to further improve the potency of the compounds of Formula II, e.g. Z-Asp-Phg-Val-AspVSmethyl (53), against caspase-3 and inhibit selectively additional caspases such as caspase-2, caspase-8, caspase-9 and caspase-1.

As is known, all caspases cleave substrates to the right of the aspartic acid amino acid in position P1. However, caspase-3 requires an additional Asp at position P4, which confers caspase-3 its specificity:

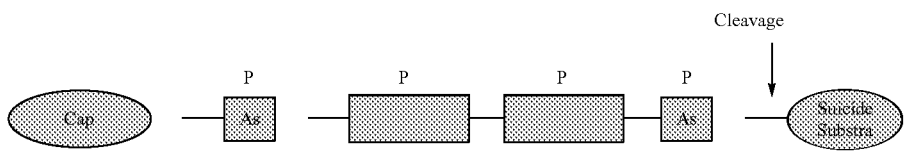

Cleavage

As shown in Table 2 hereinafter, suicide substrates such as AspVSmethyl (Compound 93) and Asp(Otbu)VSmethyl (Compound 33) are devoid of any activity against caspase-3. The substrate z-Asp(Otbu)-Phg-val-OH (Compound 16) is also devoid of any activity against caspase-3. However the fusion product of peptide and suicide substrate, z-Asp-Phg-Val-AspVSmethyl (Compound 53), proved to be a very potent inhibitor of caspase-3 with an IC50 30-90 nM. Inhibition is selective since even though caspase-7 belongs to the same group than caspase-3, the IC50 value for this caspase was about 12 fold higher. Replacement of Phg at position P3 with Ala (2'-quinolyl) enhanced the selectivity further (about 56 fold difference, see Compound 55).

As observed with z-Val-AspVSmethyl (Compound 61), the deletion of both Aspartic acid and Ala(2'-quinolyl) at P4 and P3 positions abolished completely the activity against caspase-3. The same result was observed after the deletion of Aspartic acid only in the example of z-Ala (2'-quinolyl)-Val-Asp alpha chlorovinyl methyl sulfone (Compound 50) compared with z-Asp-Ala(2'-quinolyl)-Val-Asp alpha chlorovinyl methyl sulfone (Compound 48).

Changes at Position P3 and P2

The amino acids at both position P3 and P2 can serve to selectively target caspase-3 as observed but also to selectively target other caspases. The following examples highlight this possibility: (1) The replacement of Ala(2'-quinolyl) (Compound 55) with indalylglycine at P3 position lead to z-Asp-indalylglycine-Val-AspVSmethyl (Compound 57). This substitution enhanced the inhibitory effect against the group III of caspases (caspase-3 (30-90 nM) and 7 (0.18-0.30 uM) and, with about 29 fold less efficiency, against group 1 (caspase-1 (0.6-1.2 uM)). (2) The presence of Trp at P3 position (z-Asp-Trp-Val-AspVSmethyl; Compound 88) retained the selectivity against caspase-3 (30-90 nM) and produced an additional activity against caspase-1 (0.6-1.2 uM). This molecule possesses therefore the capability to inhibit selectively two caspases belonging to two different groups, namely the proinflammatory and the proapoptotic group. (3) The presence of Glutamic acid at P-3 position (z-Asp-Glu-Val-AspVSmethyl; Compound 59) retained the selectivity against caspase-3 (IC50 20 nM) and produced an additional activity against caspase-7 (IC50 42 nM) and caspase-9 (509 nM). This molecule therefore possesses the capability to inhibit selectively two caspases belonging to two different groups, namely initiator and executioner caspases.

Changes in Position P4

Changes in position P4 can also affect the selectivity of a given inhibitor. The amino acid that has been showed to fit well into the corresponding caspase-1 pockets at position P4 is Tyrosine. Therefore, z-Tyr-Val-Ala-AspVS phenyl (Compound 96) was tested against different caspases, and it proved to be selective against caspase-1 (IC50 1.2-1.5 µM). The amino acid that has been showed to fit well into the corresponding caspase-1 pockets at position P3 is glutamic acid. Therefore, z-Tyr-Glu-Ala-AspVS methyl (Compound 82) was tested against different caspases and the inhibition of caspase-1 was enhanced to 0.5 µM.

These specific examples demonstrate that it is possible to make selective caspase-3 inhibitors based on sequences recognized by group III caspases. Following the same approach as outlined hereinafter, it is conceivable to inhibit selectively additional caspases and to further improve the potency against selected caspases.

Design for Selective Caspase-3 Inhibitors

In one embodiment, the method comprises synthesizing compounds having the following general Formula D1:

$$D_a\text{-(P3)-(P2)-}D_b\text{-suicide substrate} \tag{D1}$$

wherein
P2 is selected from the following amino acids: V, L, P, M, A, T, and H;
P3 is selected from the following amino acids: Phg, E, Indanylglycine, W, Y, A, D, Ala-(2'-quinolyl), Q, F, S, T, V, Y, G, L;
$D_a$ is (D) or (L) aspartic acid.
$D_b$ is the side chain of (D) or (L) aspartic acid.

The following compound (DEVD-vinyl phenyl sulfone) is an example a compounds having a sequence (i.e. $D_a$ is Cbz-aspartic acid; P3 is Glu; P2 is Val; $D_b$ is Asp; and the suicide substrate is vinyl phenyl sulfone) designed to selectively inhibit caspase-3:

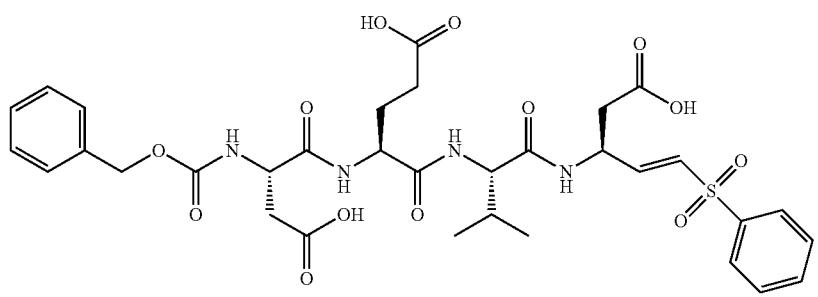 [SMILES: CC(C)[C@H](NC(=O)[C@H](CCC(=O)O)NC(=O)[C@H](CC(=O)O)NC(=O)OCc1ccccc1)C(=O)N[C@H](/C=C/S(=O)(=O)c1ccccc1)CC(=O)O]

Design for Selective Caspase-8/Caspase-9 Inhibitors

In one embodiment, the method comprises synthesizing compounds having the following general Formula D2:

(P4)-(P3)-(P2)-D-suicide substrate (D2)

where
P2 is selected from the following amino acids: T, H, V, W, I, and A;
P3 is selected from the following amino acids: E, Ala(2'-quinolyl;
P4 is selected from the following amino acids: I, L, E, D, A, P, and V;
D is the side chain of (D) or (L) aspartic acid and the suicide substrate is vinyl phenyl sulfone.

The following is an example of a compound having a sequence (i.e. P4 is Cbz-L; P3 is Glu; P2 is His; D is Asp and the suicide substrate is vinyl phenyl sulfone) designed to selectively inhibit caspase-8:

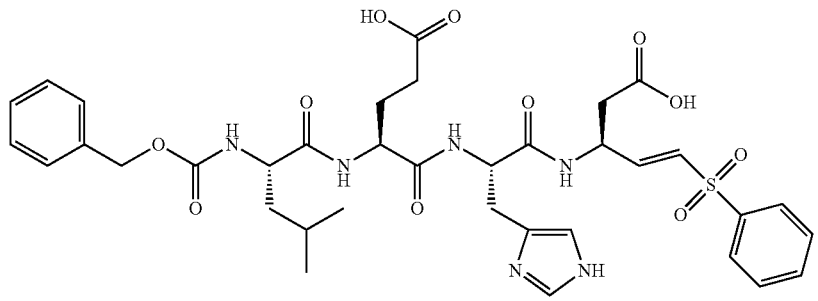 [SMILES: CC(C)C[C@H](NC(=O)OCc1ccccc1)C(=O)N[C@@H](CCC(=O)O)C(=O)N[C@@H](Cc1c[nH]cn1)C(=O)N[C@H](/C=C/S(=O)(=O)c1ccccc1)CC(=O)O]

Design for Selective Caspase-2 Inhibitors

In one embodiment, the method comprises synthesizing compounds having the following general Formula D3:

(P5)-(P4)-(P3)-(P2)-D-suicide substrate (D3)

where
P2 is selected from the following amino acids: A, S, K and V;
P3 is selected from the following amino acids: V, E, T and Q;
P4 is selected from the following amino acids: D and L;
P5 is selected from the following amino acids: V and L;
D is the side chain of (D) or (L) aspartic acid; and
the suicide substrate is selected from the group consisting of vinyl phenyl sulfone.

The following is an example of a compound (VDEHD-vinylphenyl sulfone) having a sequence (i.e. P5 is Cbz Val; P4 is Asp; P3 is Glu; P2 is His and D is Asp. The suicide substrate is vinyl phenyl sulfone), which is designed to selectively inhibit caspase-2:

Design for Selective Caspase-1 Inhibitors

In one embodiment, the method comprises synthesizing compounds having the following general Formula D4:

(P4)-(P3)-(P2)-D-suicide substrate (D4)

where
P2 is selected from the following amino acids: V, A, T, and H.
P3 is selected from the following amino acids: E, Q, D, A, G, T, V, Ala(2'-quinolyl), indanylglycine, and W;
P4 is selected from the following amino acids: Y, W, F, and D;
D is the side chain of (D) or (L) aspartic acid; and
the suicide substrate is selected from the group consisting of vinyl phenyl sulfone.

The following is an example of a compound (YEHD-vinylphenyl sulfone) having a sequence (i.e. P4 is Cbz Tyr; P3 is Glu; P2 is His; D is Asp and the suicide substrate is vinyl phenyl sulfone, which is designed to selectively inhibit caspase-1:

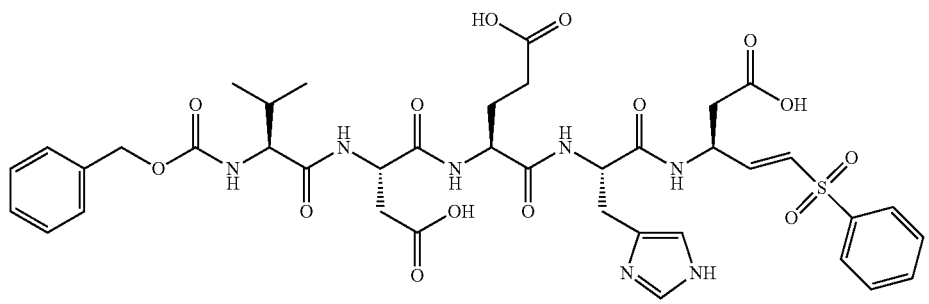 [SMILES: CC(C)[C@H](NC(=O)OCc1ccccc1)C(=O)N[C@@H](CC(=O)O)C(=O)N[C@@H](CCC(=O)O)C(=O)N[C@@H](Cc1c[nH]cn1)C(=O)N[C@H](/C=C/S(=O)(=O)c1ccccc1)CC(=O)O]

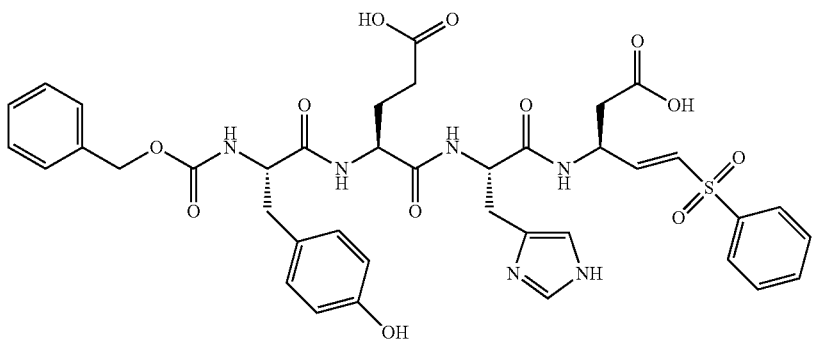 [SMILES: O=C(O)CC[C@H](NC(=O)[C@H](Cc1ccc(O)cc1)NC(=O)OCc1ccccc1)C(=O)N[C@@H](Cc1c[nH]cn1)C(=O)N[C@H](/C=C/S(=O)(=O)c1ccccc1)CC(=O)O]

D) Pharmaceutical Applications

As indicated hereinbefore and exemplified hereinafter, the compounds of the invention have beneficial pharmaceutical properties and these compounds may have pharmaceutical applications in the prevention and/or treatment of various diseases and conditions in a subject. Medical and pharmaceutical applications contemplated by the inventors include, but are not limited to, caspase-mediated diseases. In addition, the compounds of the present invention may have useful benefits on cells in vitro such as promoting cell survival or the health of the cells.

The term "subject" includes living organisms in which blood disorders, renal failure, inflammatory-related diseases associated with high blood pressure, and/or oxidative stress-related disorders, can occur, or which are susceptible to such conditions. The term "subject" includes animals (e.g., mammals (e.g., cats, dogs, horses, pigs, cows, goats, sheep, rodents (e.g., mice or rats), rabbits, squirrels, bears, primates (e.g., chimpanzees, monkeys, gorillas, and humans)), as well as avians (e.g. chickens, ducks, Peking ducks, geese), and transgenic species thereof. Preferably, the subject is a mammal. More preferably, the subject is a human. Even more preferably, the subject is a human patient in need of treatment.

The term "caspase-mediated disease" includes all diseases, disorder and/or conditions in which any one or more of caspase-1, -2, -3, -4, -5, -6, -7, -8, -9, -10, -11, -12, plays a significant role. In some embodiments, the caspase-mediated disease mainly involves executioner caspases (caspase-3, 6, 7). In another embodiment, the caspase-mediated disease mainly involves initiators (caspase-2, 8, 9, 10). In some embodiments, a compound of the invention shows a high specificity towards one particular caspase. In another embodiment, a compound of the invention is able to inhibit two groups of caspases. Yet, in another embodiment, a compound of the invention even is able to inhibit two specific caspases belonging to two different groups of caspases.

Examples of caspase-mediated disease according to the invention includes, but are not limited to, apoptosis mediated diseases, IL-1 mediated diseases, inflammatory diseases, autoimmune diseases, autoinflammatory diseases, proliferative diseases, infectious diseases, degenerative diseases, retinal disorders, inflammatory peritonitis, osteoarthritis, pancreatitis, asthma, respiratory distress syndrome, rheumatoid arthritis, systemic lupus erythematous, scleroderma, Grave's disease, autoimmune gastritis, diabetes, autoimmune hemolytic anemia, autoimmune neutropenia, thrombocytopenia, hepatitis, inflammatory bowel disease, crohn's disease, psoriasis, dermatitis, Graft vs host disease, organ transplant rejection, osteoporosis, leukemias and related disorders, multiple myeloma-related diseases, metastatic melanomas, Kaposi's sarcoma, sepsis, septic shock, Alzheimer's disease, Parkinson's disease, Huntington's disease, cerebral ischemia, epilepsy, myocardial ischemia, acute and chronic heart disease, myocardial infarction, congestive heart failure, atherosclerosis, spinal muscular atrophy, amyotrophic lateral sclerosis, multiple sclerosis, HIV-related encephalitis, aging, neurological damage due to stroke, ulcerative colitis, traumatic brain injury, spinal cord injury, hepatitis-B, hepatitis-C, hepatitis-G, liver-related diseases, renal disease, and HIV infection.

As used herein, "preventing" or "prevention" is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). Biological and physiological parameters for identifying such patients are provided herein and are also well known by physicians.

The terms "treatment" or "treating" of a subject includes the application or administration of a compound of the invention to a subject (or application or administration of a compound of the invention to a cell or tissue from a subject) with the purpose of stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indicia of success in the treatment or amelioration of an injury, pathology or condition, including any objective or subjective parameter such as abatement; remission; lessening of the rate of worsening; lessening severity of the disease; stabilization, diminishing of symptoms or making the injury, pathology or condition more tolerable to the subject; slowing in the rate of degeneration or decline; making the final point of degeneration less debilitating; or improving a subject's physical or mental well-being. In some embodiments, the term "treating" can include increasing a subject's life expectancy and/or delay before additional treatments are required.

Addressing caspase-mediated diseases is among the medical and pharmaceutical applications contemplated by present invention. Therefore, in one of its aspects the present invention relates to methods, compounds and compositions for prevention and/or treatment of a caspase-mediated disease in a subject, preferably a human patient in need thereof.

Another aspect of the invention relates to the use of the compounds described herein for inhibiting a caspase or a caspase-like protein in a cell, comprising contacting the caspase or caspase-like protein with an effective amount of a caspase inhibitor according to the invention.

In some embodiments, the subject may be suffering from a viral infection. Therefore, the invention also relates to a method for the prophylaxis or therapy of a viral infection, comprising administering to a subject in need thereof an effective dose of a caspase inhibitor according to the invention (or a pharmaceutical composition comprising the same). This may be helpful for inhibiting a cellular caspase thereby inhibiting virus multiplication.

Also of particular interest is a method for the treatment of excessive apoptosis affected by caspase activity in a cell or a tissue, comprising contacting the cell or the tissue with an effective amount of one or more caspase inhibitor according to the invention (or a pharmaceutical composition comprising the same).

Also of particular interest is a method for simulating stem cell proliferation by preventing some of the stem cells from entering a partial or complete apoptosis cycle. The method for culturing a large quantity of stem cells may involves an effective amount of one or more caspase inhibitor according to the invention (or a pharmaceutical composition comprising the same) and a medium for culturing stem cells.

Although focusing on caspases, the present is not so limited. For instance, it is conceivable that the compounds of the invention be also effective in inhibiting additional families of proteases, including but not limited to, serine peptidases, cysteine peptidases, aspartic peptidases, metallo-peptidases, and other peptidases of unknown catalytic type. For a more elaborate listing of proteases that may be inhibited by the compounds defined herein, see ZBIGNIEW GRZONKA. Cysteine protease. Industrial Enzymes, 181-195, Chapter 11, 2007 Springer.

In order to evaluate, assess, and/or confirm the efficacy of the method, compounds and/or compositions of the invention, serial measurements can be determined. Quantitative assessment of caspase functions and parameters of caspase dysfunction are well known in the art. Examples of assays for the determination of caspases activity are provided in the Exemplification section.

The compounds according to the invention can be further analyzed, tested or validated for their ability to cross the Blood Brain Barrier BBB is so desired. Many in-vitro, in-vivo and in-silico methods may be employed during drug development to mimic the BBB (Lohmann et al. (2002) Predicting blood-brain barrier permeability of drugs: evaluation of different in vitro assays. *J Drug Target* 10:263-276; Nicolazzo et al. (2006) Methods to assess drug permeability across the blood-brain barrier. *J Pharm Pharmacol* 58:281-293). In-vitro models include primary endothelial cell culture and immortalized cell lines such as Caco-2, BMEC, MDCK. These cells are useful as a screening method and can appropriately rank compounds in order of BBB permeability. In vivo models such as the internal carotid artery single injection or perfusion, intravenous bolus injection, brain efflux index and intracerebral microdialysis provide more accurate information regarding brain uptake, and these can be complemented with novel imaging techniques (such as magnetic resonance imaging and positron emission tomography), although such methods are not suited to high-throughput permeability assessment.

In certain embodiments, at least some of the prodrugs administered generates the corresponding pharmaceutical compound only after absorption by the gastrointestinal tract and/or only once it has reached the brain, i.e. after it has passed the blood brain barrier (BBB).

E) Pharmaceutical Compositions and Formulations

A related aspect of the invention concerns pharmaceutical compositions comprising one or more of the compounds of the invention described herein. As indicated hereinbefore, the compounds of the invention may be useful in preventing and/or treating caspase-mediated disease, and more particularly sepsis, myocardial infarction, ischemic stroke, spinal cord injury (SCI), traumatic brain injury (TBI) and neurodegenerative disease (e.g. multiple sclerosis (MS) and Alzheimer's, Parkinson's, and Huntington's diseases.

As used herein, the term "therapeutically effective amount" means the amount of compound that, when administered to a subject for treating or preventing a particular disorder, disease or condition, is sufficient to effect such treatment or prevention of that disorder, disease or condition. Dosages and therapeutically effective amounts may vary for example, depending upon a variety of factors including the activity of the specific agent employed, the age, body weight, general health, gender, and diet of the subject, the time of administration, the route of administration, the rate of excretion, and any drug combination, if applicable, the effect which the practitioner desires the compound to have upon the subject and the properties of the compounds (e.g. bioavailability, stability, potency, toxicity, etc), and the particular disorder(s) the subject is suffering from. In addition, the therapeutically effective amount may depend on the subject's blood parameters (e.g. lipid profile, insulin levels, glycemia), the severity of the disease state, organ function, or underlying disease or complications. Such appropriate doses may be determined using any available assays including the assays described herein. When one or more of the compounds of the invention is to be administered to humans, a physician may for example, prescribe a relatively low dose at first, subsequently increasing the dose until an appropriate response is obtained.

As used herein, the term "pharmaceutical composition" refers to the presence of at least one compound of the invention according to any one of Formula I, IA, II, IIA, III, or IIIA as defined herein and at least one pharmaceutically acceptable vehicle. Examples of representative compounds of the invention include the compounds in Table 1 and pharmaceutically acceptable salts thereof.

"Pharmaceutically acceptable vehicle" refers to a diluent, adjuvant, excipient, or carrier with which a compound is administered. The term "pharmaceutically acceptable" refers to drugs, medicaments, inert ingredients etc., which are suitable for use in contact with the tissues of humans and lower animals without undue toxicity, incompatibility, instability, irritation, allergic response, and the like, commensurate with a reasonable benefit/risk ratio. It preferably refers to a compound or composition that is approved or approvable by a regulatory agency of the Federal or state government or listed in the U.S. Pharmacopoeia or other generally recognized pharmacopoeia for use in animals and more particularly in humans. The pharmaceutically acceptable vehicle can be a solvent or dispersion medium containing, for example, water, ethanol, polyol (for example, glycerol, propylene glycol, and liquid polyethylene glycol, and the like), suitable mixtures thereof, and vegetable oils. Additional examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. Prevention of the action of microorganisms can be achieved by various antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of injectable compositions can be brought about by including in the composition an agent which delays absorption, for example, aluminum monostearate or gelatin. Nanoparticles, liposomes, and antibodies conjugated to nanoparticles or combinations thereof, are also contemplated as pharmaceutically acceptable vehicles.

In some embodiments, the compositions of the invention comprise an effective amount of a compound of the Formula I, IA, II, IIA, III, or IIIA as described hereinbefore, preferably compound Z-Asp-Indanylglycine-Val-Aspmethyl vinyl sulfone (57); Z-Asp-Glu-Val-Aspmethyl vinyl sulfone (59) Z-Asp-Ala(2'-quinolyl)-Val-Aspmethyl vinyl sulfone (55); Z-Asp-Phg-Val-Aspmethyl vinyl sulfone (53); Z-Asp-Ala (2'-quinolyl)-Val-Asp-αchlorovinyl methylsulfone (48); Z-Asp(β-methyl)-Indanylglycine-Val-Asp(β-methyl)methyl vinyl sulfone (51) Z-Asp-Tyr-Val-Aspmethyl vinyl sulfone (76) Z-Asp-Trp-Val-Aspmethyl vinyl sulfone (88) or a pharmaceutically acceptable salt thereof.

In some embodiments the invention pertains to pharmaceutical compositions for preventing and/or treating diseases or other medical conditions in which at least one caspase is significantly involved that include one or more compounds of Formula I, IA, II, IIA, III, or IIIA as defined herein.

In some embodiments the invention pertains to pharmaceutical compositions for preventing and/or treating diseases or other medical conditions in which at least one caspase is significantly involved, the composition comprising one or more compounds of Formula I, IA, II, IIA, III, or IIIA as defined herein.

The compounds of the invention may be formulated prior to administration into pharmaceutical compositions using available techniques and procedures. For instance, the pharmaceutical compositions may be formulated into suitable administration (orally, parenterally, (intravascular (IV), intraarterial (IA), intramuscular (IM), depo-IM, subcutaneous (SC), and depo SC), sublingually, intranasally (inhalation), intrathecally, topically, or rectally.

Preferably, the compound(s) of the invention can be orally administered. The formulations may conveniently be presented in unit dosage form and may be prepared by any methods well known in the art of pharmacy. Methods of preparing these formulations or compositions include the step of bringing into association a compound of the present invention with a pharmaceutically acceptable vehicle (e.g. an inert diluent or an assimilable edible carrier) and, optionally, one or more accessory ingredients. In general, the formulations are prepared by uniformly and intimately bringing into association a compound of the present invention with liquid carriers, or finely divided solid carriers, or both, and then, if necessary, shaping the product. The amount of the therapeutic agent in such therapeutically useful compositions is such that a suitable dosage will be obtained.

Formulations of the invention suitable for oral administration may be in the form of capsules (e.g. hard or soft shell gelatin capsule), cachets, pills, tablets, lozenges, powders, granules, pellets, dragees, e.g., coated (e.g., enteric coated) or uncoated, or as a solution or a suspension in an aqueous or non-aqueous liquid, or as an oil-in-water or water-in-oil liquid emulsion, or as an elixir or syrup, or as pastilles or as mouth washes and the like, each containing a predetermined amount of a compound of the present invention as an active ingredient. A compound of the present invention may also be administered as a bolus, electuary or paste, or incorporated directly into the subject's diet. Moreover, in certain embodiments these pellets can be formulated to (a) provide for instant or rapid drug release (i.e., have no coating on them); (b) be coated, e.g., to provide for sustained drug release over time; or (c) be coated with an enteric coating for better gastrointestinal tolerability. Coating may be achieved by conventional methods, typically with pH or time-dependent coatings, such that the compound(s) of the invention is released in the vicinity of the desired location, or at various times to extend the desired action. Such dosage forms typically include, but are not limited to, one or more of cellulose acetate phthalate, polyvinylacetate phthalate, hydroxypropyl methyl cellulose phthalate, ethyl cellulose, waxes, and shellac.

In solid dosage forms for oral administration a compound of the present invention may be mixed with one or more pharmaceutically acceptable carriers, such as sodium citrate or dicalcium phosphate, or any of the following: fillers or extenders, such as starches, lactose, sucrose, glucose, mannitol, or silicic acid; binders, such as, for example, carboxymethylcellulose, alginates, gelatin, polyvinyl pyrrolidone, sucrose or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Peroral compositions typically include liquid solutions, emulsions, suspensions, and the like. The pharmaceutically acceptable vehicles suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, tragacanth, and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Pharmaceutical compositions suitable for injectable use may include sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fungi. Sterile injectable solutions can be prepared by incorporating the therapeutic agent in the required amount in an appropriate solvent with one or a combination of ingredients enumerated above, as required, followed by filtered sterilization. Generally, dispersions are prepared by incorporating the therapeutic agent into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient (i.e., the therapeutic agent) plus any additional desired ingredient from a previously sterile-filtered solution thereof.

Pharmaceutical formulations are also provided which are suitable for administration as an aerosol, by inhalation. These formulations comprise a solution or suspension of the desired compound of any Formula herein or a plurality of solid particles of such compound(s). The desired formulation may be placed in a small chamber and nebulized Nebulization may be accomplished by compressed air or by ultrasonic energy to form a plurality of liquid droplets or solid particles comprising the agents or salts. The liquid droplets or solid particles should have a particle size in the range of about 0.5 to about 5 microns. The solid particles can be obtained by processing the solid agent of any Formula described herein, or a salt thereof, in any appropriate manner known in the art, such as by micronization. The size of the solid particles or droplets will be, for example, from about 1 to about 2 microns. In this respect, commercial nebulizers are available to achieve this purpose. A pharmaceutical formulation suitable for administration as an aerosol may be in the form of a liquid, the formulation will comprise a water-soluble agent of any Formula described herein, or a salt thereof, in a carrier which comprises water. A surfactant may be present which lowers the surface tension of the formulation sufficiently to result in the formation of droplets within the desired size range when subjected to nebulization.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions may comprise an effective amount, usually at least about 0.1%, or even from about 1% to about 5%, of a compound of the invention. Suitable carriers for topical administration typically remain in place on the skin as a continuous film, and resist being removed by perspiration or immersion in water. Generally, the carrier is organic in nature and capable of having dispersed or dissolved therein the therapeutic agent. The carrier may include pharmaceutically acceptable emollients, emulsifiers, thickening agents, solvents and the like.

Other compositions useful for attaining systemic delivery of the subject agents include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compound(s) of the invention may also be administered parenterally, intraperitoneally, intravenously, intraspinally, intrathecally or intracerebrally. For such compositions, the compound(s) of the invention can be prepared in glycerol, liquid polyethylene glycols, and mixtures thereof and in oils. Under ordinary conditions of storage and use, these preparations may contain a preservative to prevent the growth of microorganisms.

The method of treatment of the present invention may also include co-administration of the at least one compound according to the invention, or a pharmaceutically acceptable salt thereof together with the administration of another therapeutically effective agent. Therefore, an additional aspect of the invention relates to methods of concomitant therapeutic treatment of a subject, comprising administering to a subject in need thereof an effective amount of a first agent and a second agent, wherein the first agent is as defined in Formula I, IA, II, IIA, III, or IIIA and the second agent is for the prevention or treatment of any one of disorder or disease indicated hereinbefore. As used herein, the term "concomitant" or "concomitantly" as in the phrases "concomitant therapeutic treatment" or "concomitantly with" includes administering a first agent in the present of a second agent. A concomitant therapeutic treatment method includes methods in which the first, second, third or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and as a second actor may administer to the subject a second agent and the administering steps may be executed at the same time, or nearly the same time, or at distant times, so long as the first agent (and/or additional agents) are after administration in the presence of the second agent (and/or additional agents). The actor and the subject may be the same entity (e.g. a human).

Accordingly, the invention also relates to a method for preventing, reducing or eliminating a symptom or complication of any one of the above mentioned disease or condition. The method comprises administering, to a subject in need thereof, a first pharmaceutical composition comprising at least one compound of the invention and a second pharmaceutical composition comprising one or more additional active ingredients, wherein all active ingredients are administered in an amount sufficient to inhibit, reduce, or eliminate one or more symptoms or complications of the disease or condition to be treated. In one aspect, the administration of the first and second pharmaceutical composition is temporally spaced apart by at least about two minutes. Preferably the first agent is a compound of Formula I, IA, II, IIA, III, or IIIA as defined herein, or a pharmaceutically acceptable salt thereof. The second agent may be selected from the following list of compounds: Z-Asp-Phg-Val-Aspmethyl vinyl sulfone (53)

F) Screening Assays

The compounds of the present invention may also be used in screening methods. For instance, these compounds may be used in methods for tracking activity of caspases in vitro and/or in vivo. The compounds of the present invention may also be helpful for identifying other compounds that bind to a caspase active side. In some embodiments, the compounds of the invention are labeled or tagged (e.g. fluorescently or radioactively labeled, affinity tag). Fluorescent or radiolabeled compounds may also be useful in diagnostic assays.

There are a number of ways in which to determine the binding of a compound of the present invention to the caspase. In one embodiment the caspase is bound to a support, and a labeled compound of the invention is added to the assay. Alternatively, the compound of the invention may be bound to the support and the caspase is added.

The compounds of the invention may also be used as competitors to screen for additional drug candidates or test compounds. As used herein, the terms "drug candidate" or "test compounds" are used interchangeably and describe any molecule, for example, protein, oligopeptide, small organic molecule, polysaccharide, polynucleotide, and the like, to be tested for bioactivity.

Typically, the signals that are detected in the assay (e.g. in vitro, in vivo and/or diagnostic) may include fluorescence, resonance energy transfer, time resolved fluorescence, radioactivity, fluorescence polarization, plasma resonance, or chemiluminescence and the like, depending on the nature of the label. Detectable labels useful in performing screening assays in this invention include a fluorescent label such as Fluorescein, Oregon green, dansyl, rhodamine, tetramethyl rhodamine, texas red, $Eu^{3+}$; a chemiluminescent label such as luciferase; colorimetric labels; enzymatic markers; or radioisotopes such as tritium, $I^{125}$ and the like. Affinity tags, which may be useful in performing the screening assays of the present invention include be biotin, polyhistidine and the like.

F) Kits

The compound(s) of the invention may be packaged as part of a kit, optionally including a container (e.g. packaging, a box, a vial, etc). The kit may be commercially used according to the methods described herein and may include instructions for use in a method of the invention. Additional kit components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components optionally further comprise buffers.

The compound(s) of the invention may or may not be administered to a patient at the same time or by the same route of administration. Therefore, the methods of the invention encompass kits which, when used by the medical practitioner, can simplify the administration of appropriate amounts of two or more active ingredients to a patient.

A typical kit of the invention comprises a unit dosage form of a at least one compound according to the invention, e.g., a compound of Formula I, IA, II, IIA, III, or IIIA as defined herein or a pharmaceutically acceptable salt thereof, and a unit dosage form of at least one additional active ingredient. Examples of additional active ingredients that may be used in conjunction with the compounds according to the invention, include, but are not limited to any of the compounds that could be used in combination with the compound(s) of the invention as indicated herein before.

Kits of the invention can further comprise devices that are used to administer the active ingredients. Examples of such devices include, but are not limited to, syringes, drip bags, patches, inhalers, enemas, and dispensers for the administration of suppository formulations.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles are provided hereinbefore.

Headings are included herein for reference and to aid in locating certain sections These headings are not intended to limit the scope of the concepts described therein under, and these concepts may have applicability in other sections throughout the entire specification Thus, the present invention is not intended to be limited to the embodiments shown herein but is to be accorded the widest scope consistent with the principles and novel features disclosed herein.

Unless otherwise indicated, all numbers expressing quantities of ingredients, reaction conditions, concentrations, properties, and so forth used in the specification and claims are to be understood as being modified in all instances by the term "about." At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The invention is further illustrated by the following examples, which should not be construed as further limiting.

EXAMPLES

The Examples set forth herein below provide exemplary methods for the preparation of certain representative compounds encompassed by general Formula I, IA, II, IIA, III, or IIIA. Some Examples provide exemplary uses of certain representative compounds of the invention. Also provided are exemplary methods for assaying the compounds of the invention for in vitro and in vivo efficacy.

Example I

Synthesis of compound 4 (Cbz-Asp(O-tBu)-Ala (2'quinolyl)-ValOH)

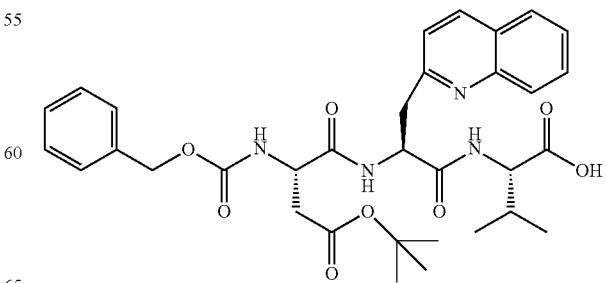

a) Fmoc-Ala(2'-quinolyl)-Val-OAllyl

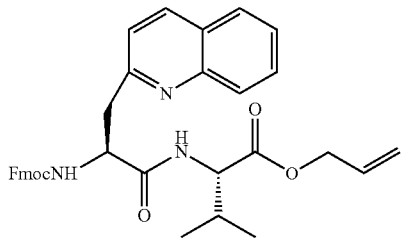

Fmoc-Ala (2'-quinolyl)-OH (0.152 g, 0.347 mmol) was solvated in DMF (1 mL) and CH$_2$Cl$_2$ (0.9 mL). L-Val allylester toluene-4-sulfonate (0.115 g, 1.01 eq) in 0.3 mL of CH$_2$Cl$_2$ was added, followed with 4-methylmorpholine (0.04 mL, 1.05 eq) and EDC (0.0681 g, 1.02 eq). The mixture was stirred for 3 hours, and then it was extracted using CH$_2$Cl$_2$/brine. The organic layer was dried over MgSO$_4$, filtered off and concentrated to dryness.

b) Ala(2'quinolyl)-Val-OAllyl

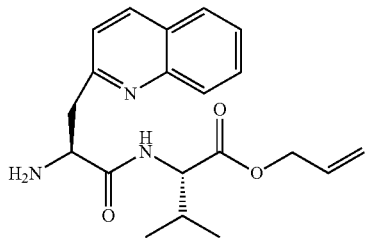 [SMILES: C=CCOC(=O)[C@@H](NC(=O)[C@@H](N)Cc1ccc2ccccc2n1)C(C)C]

The Fmoc-Ala(2'-quinolyl)-Val(O— Allyl) (0.425 g, 0.737 mmol) was solvated in CH$_2$Cl$_2$ (40 mL) followed by dropwise addition of piperidine (0.6 mL, 8.24 eq). After 40 min the mixture was evaporated to dryness under vacuum. The product was then purified on silica using a gradient of MeOH/CH$_2$Cl$_2$ (0 to 10%) to get 0.188 g of desired compound.

NMR $^1$H (CDCl$_3$, 400 MHz) δ: 8.18 (s, 1H, NH); 8.08 (d, 1H, J=8.4 Hz); 8.03 (d, 1H, J=8.47 Hz); 7.79 (d, 1H, J=7.91 Hz); 7.71-7.68 (m, 1H); 7.52-7.49 (m, 1H); 7.35 (d, 1H, J=8.42 Hz); 5.92-5.85 (m, 2H); 5.34-5.22 (m, 2H); 4.63-4.58 (m, 2H); 4.55-4.52 (m, 1H); 3.95-3.93 (m, 1H); 3.52 (dd, 1H, J=3.95 Hz); 3.25-3.20 (m, 1H); 2.20-2.13 (m, 1H); 2.01 (m, 2H, NH$_2$); 0.85 (m, 6H).

c) Cbz-Asp(O-tBu)-Ala(2'-quinolyl)-Val-OAllyl

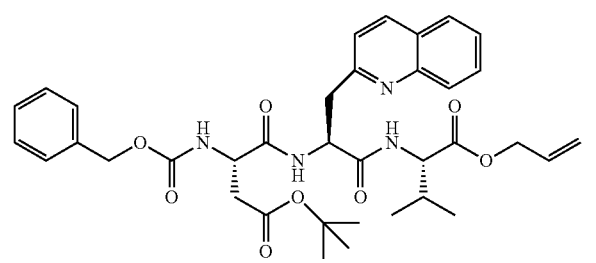 [SMILES: C=CCOC(=O)[C@@H](NC(=O)[C@H](Cc1ccc2ccccc2n1)NC(=O)[C@H](CC(=O)OC(C)(C)C)NC(=O)OCc1ccccc1)C(C)C]

Ala(2'-quinolyl)-Val(O-Allyl) (0.054 g, 0.1519 mmol) was solvated in CH$_2$Cl$_2$ (0.7 mL) followed by addition of L-Asp (O-tBu)-OH (0.053 g, 1.08 eq) and 4-methylmorpholine (0.018 mL, 1.08 eq) and finally DPC (0.025 mL, 1.06 eq). The mixture was stirred for 1 hour. It was then subjected to a liquid extraction dichloromethane/brine. The organic layer was dried over MgSO$_4$, concentrated to vacuum and purified on silica using a gradient of MeOH/CH$_2$Cl$_2$ (0 to 10%) to get 0.084 g of the desired compound.

d) Cbz-Asp(O-tBu)-Ala(2'-quinolyl)-ValOH

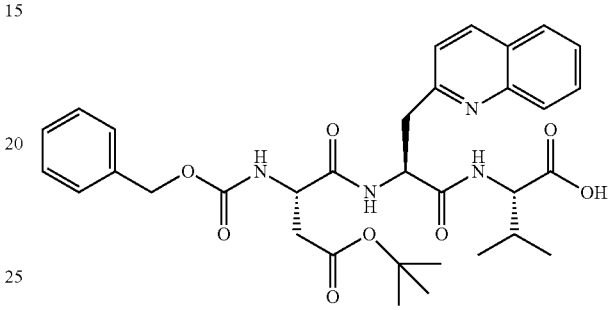

Cbz-Asp (OtBu)-Ala(2'-quinolyl)-Val (OAllyl) (0.082 g, 0.1241 mmol) was dissolved in THF (3.5 mL) and rotary evaporated to dryness, the sample was then redissolved in THF (3.5 mL) and vacuum aspirated (3*1 min of aspiration), followed by replacement of the atmosphere with Argon. Morpholine (0.04 mL, 3.7 eq) was added, followed by Pd(PPh$_3$)$_4$ (0.0171 g, 0.12 eq). The sample flask was then covered with a tin foil and kept under stirring for 3 days under Argon. The compound was evaporated to dryness and the obtained residue was subjected to purification on C$_{18}$ using a gradient MeOH/solution of H$_2$O at pH=3.5 (0 to 100%) to get 0.065 g of the desired compound.

NMR $^1$H (CD$_3$OD, 400 MHz) δ: 8.18 (d, 1H, J=8.4 Hz); 8.02 (d, 1H, J=8.49 Hz); 7.84 (d, 1H, J=8.08 Hz); 7.63 (t, 1H, J=7.51 Hz); 7.52 (t, 1H, J=7.39 Hz); 7.41 (d, 1H, J=8.3 Hz); 7.40-7.30 (m, 5H); 5.03-4.93 (m, 3H); 4.50-4.48 (m, 1H); 4.26 (d, 1H, J=4.9 Hz); 3.48-3.34 (m, 2H); 2.73-2.68 (m, 1H); 2.54-2.49 (m, 1H); 2.15-2.11 (m, 1H); 1.36 (m, 9H); 0.87-0.84 (m, 6H).

Example 2

Synthesis of compound 5
(Ts-Ala(2'-quinolyl)-Val-OH)

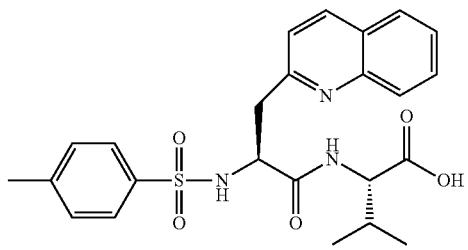 [SMILES: Cc1ccc(S(=O)(=O)N[C@@H](Cc2ccc3ccccc3n2)C(=O)N[C@H](C(=O)O)C(C)C)cc1]

a) Ts-Ala(2'-quinolyl)-OH

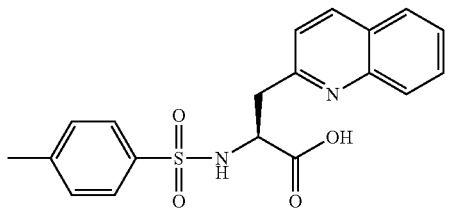 [SMILES: Cc1ccc(S(=O)(=O)N[C@@H](Cc2ccc3ccccc3n2)C(=O)O)cc1]

To L-Ala(2'-quinolyl)-OH (0.060 g, 0.277 mmol) was added H$_2$O (0.4 mL) and THF (0.15 mL). The mixture was stirred for 2 min before adding TEA (0.074 ml, 1.93 eq). The mixture was allowed to reach 0° C., before adding Tosyl chloride (0.052 g, 1 eq) in THF (0.4 mL) in a dropwise manner. The mixture was then allowed to warm to room temperature and stirred for 16 hours. The mixture was diluted with EtOAc (8 mL) and H$_2$O (2 mL), then it was acidified with HCl 1N (dropwise addition) to reach pH 3/4. The mixture was extracted with EtOAc, dried over MgSO$_4$ and evaporated to dryness, to get upon addition of MeOH (0.5 mL) 30 mg of precipitate; an other portion could be obtained from the solution.

NMR $^1$H (DMSO, 400 MHz) δ: 8.30-8.23 (m, 1H, NH); 8.14 (d, 1H, J=8.37 Hz); 7.89 (d, 1H, J=8.0 Hz); 7.78 (d, 1H, J=8.39 Hz); 7.70 (t, 1H, J=7.2 Hz); 7.55 (t, 1H, J=7.33 Hz); 7.32-7.27 (m, 3H); 6.88 (d, 2H, J=8.05 Hz); 4.28 (s, 1H); 3.4-3.03 (m, 2H); 2.13 (s, 3H).

b) Ts-Ala(2'-quinolyl)-Val-OAllyl

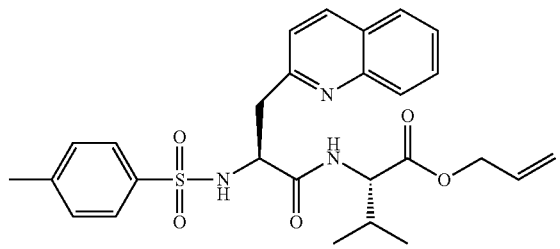 [SMILES: C=CCOC(=O)[C@@H](NC(=O)[C@H](Cc1ccc2ccccc2n1)NS(=O)(=O)c1ccc(C)cc1)C(C)C]

Ts-Ala(2'-quinolyl)-OH (0.027 g, 0.076 mmol) was solvated in CH$_2$Cl$_2$ followed by addition of L-Val-OAllyl ester toluene-4-sulfonate (0.025 g, 1.02 eq), 4-methylmorpholine (0.017 mL, 1.91 eq), DMAP (0.0012 g, 0.13 eq) and finally EDC (0.015 g, 1.04 eq). The progress of the reaction was followed by TLC. The mixture was extracted with CH$_2$Cl$_2$/brine. The organic layer was dried over MgSO$_4$, filtered off and concentrated to dryness. The obtained residue was purified on silica using a gradient EtOAc/Hexane (5 to 60%) to get 10 mg of the desired compound.

NMR $^1$H (CDCl$_3$, 400 MHz) δ: 7.99 (m, 2H); 7.89 (d, 1H, J=8.93 Hz); 7.76 (d, 1H, J=8.06 Hz); 7.72 (t, 1H, J=8.16 Hz); 7.64 (m, 2H); 7.53 (t, 1H, J=7.61 Hz); 7.45 (d, 1H, J=6.86 Hz); 7.16 (d, 1H, J=8.34 Hz); 7.08 (m, 2H); 5.86-5.79 (m, 1H); 5.27 (dd, 1H, J=17.25 Hz, J=1.36 Hz); 5.20 (dd, 1H, J=10.4 Hz, J=1.0 Hz); 4.58-4.5 (m, 2H); 4.38 (dd, 1H, J=8.78 Hz, J=5.02 Hz); 4.22 (q, 1H, J=5.58 Hz); 3.41 (dd, 1H, J=15.50 Hz, J=5.23 Hz); 3.14 (dd, 1H, J=15.53 Hz, J=5.64 Hz); 2.33 (s, 3H); 2.16-2.00 (m, 1H); 0.72 (d, 3H, J=6.8 Hz); 0.65 (d, 3H, J=6.85 Hz).

c) Ts-Ala(2'quinolyl)-Val-OH

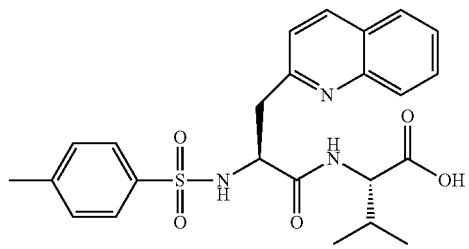 [SMILES: Cc1ccc(S(=O)(=O)N[C@@H](Cc2ccc3ccccc3n2)C(=O)N[C@H](C(=O)O)C(C)C)cc1]

The Ts-Ala(2'-quinolyl)-OAllyl (0.010 g, 0.02 mmol) was dissolved in THF (3.5 mL) and rotary evaporated to dryness, the sample was then redissolved in THF (3.5 mL) and vacuum aspirated (3*1 min of aspiration), followed by replacement of the atmosphere with Argon. Pd(PPh$_3$)$_4$ (0.0036 g, 0.16 eq) was added under Argon, followed by Morpholine (0.007 mL, 4.1 eq). The sample flask was then covered with a tin foil and kept under stirring for 3 days under Argon. The compound was evaporated to dryness and the obtained residue was subjected to purification on C$_{18}$ using a gradient: MeOH/H$_2$O (15 to 100%) to get 0.006 g of the desired compound.

NMR $^1$H (CD$_3$OD, 400 MHz) δ: 8.05 (d, 1H, J=8.44 Hz); 7.88-7.84 (m, 2H); 7.76-7.72 (m, 1H); 7.58-7.55 (m, 1H); 7.33-7.29 (m, 3H); 6.78-6.76 (m, 2H); 4.35 (dd, 1H, J=10.43 Hz, J=3.38 Hz); 4.19 (d, 1H, J=4.6 Hz); 3.44-3.03 (m, 2H); 2.20-2.12 (m, 1H); 2.12 (s, 3H); 0.93-0.89 (m, 6H).

Example 3

Synthesis of compound 12
(Cbz-Asp(O-tBu)-Indanylglycine-Val-OH)

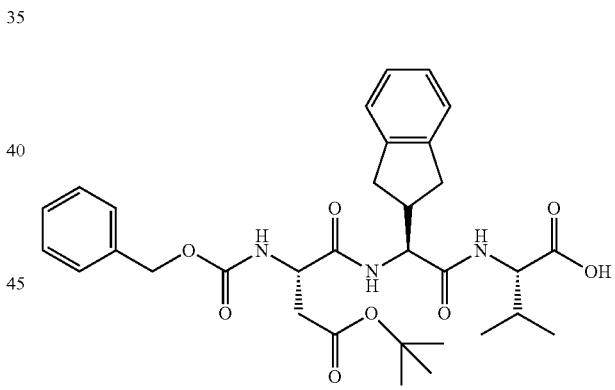

a) Fmoc-Indanylglycine-Val-OAllyl

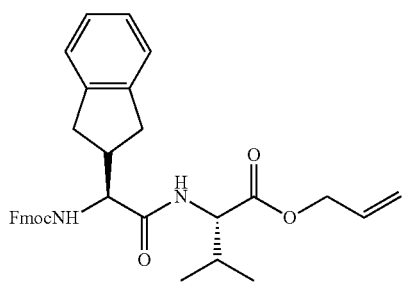

Fmoc Indanylglycine (0.54 g, 1.315 mmol) was solvated in CH₂Cl₂ (5 mL) and DMF (1.8 mL) followed with the addition of L-Val allylester (0.437 g, 1 eq), 4-methylmorpholine (0.15 ml, 1.04 eq) and 4 min latter DMAP (14.5 mg, 0.09 eq) then EDC (0.265 g, 1.05 eq). The mixture was stirred for 1 hour 45 min. Then it was extracted using EtOAc/brine. The organic layer was dried over MgSO₄, filtered off and concentrated to dryness.

b) Indanylglycine-Val-OAllyl

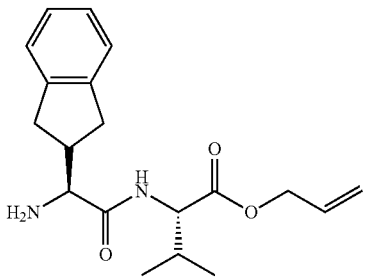 [SMILES: C=CCOC(=O)[C@@H](NC(=O)[C@@H](N)C1Cc2ccccc2C1)C(C)C]

Fmoc-Indanylglycine-Val-OAllyl (0.758 g, 1.31 mmol) was solvated in CH₂Cl₂ (5 mL) and DMF (1.8 mL) followed by dropwise addition of piperidine (1.05 mL, 8.1 eq) over 30 seconds. After 45 min, the mixture was subjected to extraction CH₂Cl₂/brine (30/15 mL) and saturated NH₄Cl (5 mL). The organic layer was dried over MgSO₄, concentrates and purified by silica using a gradient of MeOH/CH₂Cl₂ (0 to 5%) to get 0.45 g of the desired compound.

NMR ¹H (CDCl₃, 400 MHz) δ: 7.80 (d, 1H, NH); 7.20-7.17 (m, 2H); 7.15-7.11 (m, 2H); 5.96-5.88 (m, 1H); 5.37-5.25 (m, 2H); 4.68-4.58 (m, 3H); 3.53 (d, 1H, J=5.05 Hz); 3.12-2.8 (m, 5H); 2.27-2.20 (m, 1H); 0.98 (d, 3H, J=6.85 Hz); 0.94 (d, 3H, J=6.88 Hz).

c) Cbz-Asp(O-tBu)-Indanylglycine-Val-OAllyl

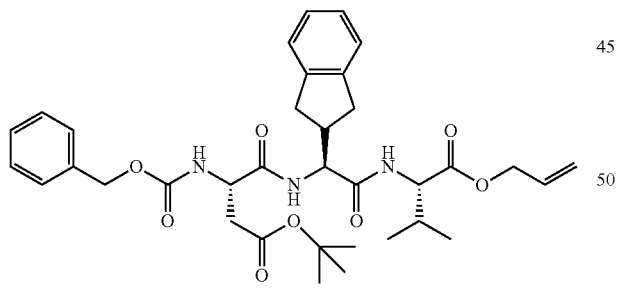

Indanylglycine-Val-OAllyl (0.46 g, 1.3 mmol) and Z-L-Asp(OtBu)-OH (0.425 g, 1.3 mmol) were solvated in CH₂Cl₂ (4.5 mL) followed by addition of 4-methylmorpholine (1.45 mL, 1.01 eq), DMAP (14 mg, 0.09 eq) then EDC (0.251 g, 1.01 eq). The mixture was stirred for 1 hour 40 min. Then it was extracted using CH₂Cl₂/brine. The organic layer was dried over MgSO₄, concentrates and purified by silica using a gradient of EtOAc/Hexane (10 to 80%) to get 0.578 g of the desired compound.

NMR ¹H (CD₃OD, 400 MHz) δ: 7.35-7.25 (m, 5H); 7.15-7.07 (m, 4H); 6.0-5.92 (m, 1H); 5.36 (dd, 1H, J=17.17 Hz, J=1.429 Hz); 5.24 (dd, 1H, J=10.45 Hz, J=1.251 Hz); 5.09-5.036 (m, 2H); 4.77-4.61 (m, 2H); 4.54-4.50 (m, 2H); 4.33 (d, 1H, J=6.04 Hz); 2.97-2.52 (m, 7H); 2.20-2.011 (m, 1H); 1.41 (s, 9H); 0.97 (d, 3H, J=1.78 Hz); 0.96 (d, 3H, J=1.78 Hz).

d) Cbz-Asp(O-tBu)Indanylglycine-Val-OH

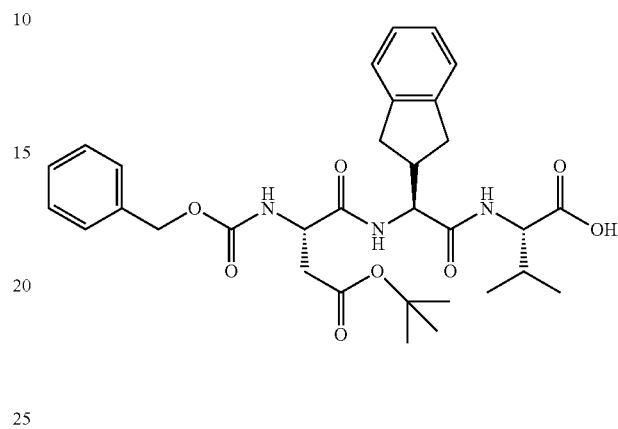

Z-Asp (O-tBu)-Indanylglycine-Val-(OAllyl) (0.102 g, 0.1611 mmol) was dissolved in THF (6 mL) and rotary evaporated to dryness, the sample was then redissolved in THF (6 mL) and vacuum aspirated (3*1 min of aspiration), followed by replacement of the atmosphere with Argon. Pd(PPh₃)₄ (0.017 g, 0.151 0.094 eq) was added in one shot, the flask was then evacuated with Argon. Morpholine (0.06 mL, 4.28 eq) was added and the flask covered with a tin foil. The mixture was kept under stirring for 2.5 days under Argon. The sample was evaporated to dryness and the obtained residue was subjected to purification on C₁₈ using a gradient MeOH/solution of H₂O at pH=3.5 (10 to 100%) to get 0.046 g of the desired compound.

NMR ¹H (CD₃OD, 400 MHz) δ: 7.4-7.23 (m, 5H); 7.18-7.03 (m, 4H); 5.20-5.0 (m, 2H); 4.58-4.50 (m, 2H); 4.3 (d, 1H, J=5.5 Hz); 3.0-2.7 (m, 6H); 2.6-2.50 (m, 1H); 1.4 (s, 9H); 0.97 (d, 3H, J=2.06 Hz); 0.96 (d, 3H, J=2.18 Hz).

Example 4

Synthesis of compound 16
(Z-Asp(β-tert-butyl)-Phg-Val-OH)

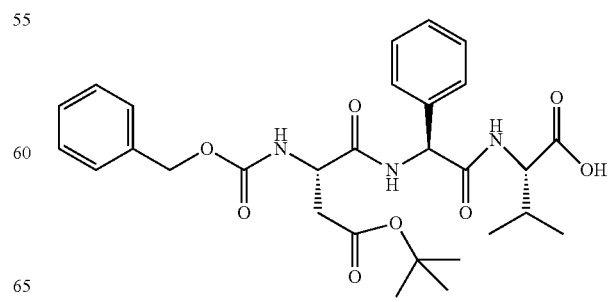

a) Fmoc-Phg-Val-OAllyl

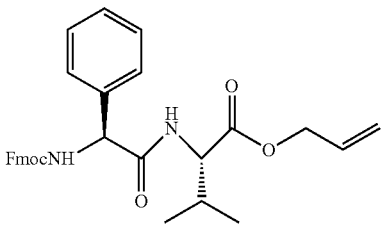

Fmoc-PhgOH (1 g, 2.678 mmol) was dissolved in a mix of anhydrous dichloromethane and DMF (9 ml/0.5 ml). Val(OAllyl) tosyl salt form (0.804 g, 2.44 mmol) in 1 ml of dichloromethane was added followed by diisopropylcarbodiimide (0.414 ml, 2.44 mmol) and N-methyl morpholine (0.270 ml, 2.44 mmol). The mixture was stirred for 2.20 hrs at RT, then filtered off on a path of celite (1 cm) and washed with dichloromethane. The filtrate was concentrated and the obtained residue was used as a crude material for the next step.

b) Phg-Val-OAllyl

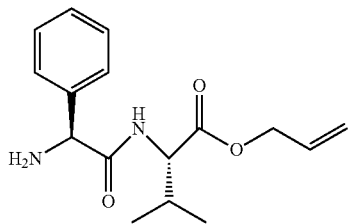 [SMILES: C=CCOC(=O)[C@@H](NC(=O)[C@@H](N)c1ccccc1)C(C)C]

1.45 g of the previous crude material (Fmoc-Phg-Val-OAllyl) was dissolved in a solution of 20% piperidine in dichloromethane (8.5 ml) and stirred at room temperature for 45 minutes. The mixture was then concentrated under vacuum, diluted with dichloromethane and filtered off through a path of celite (1 cm). The solvent was evaporated to dryness and then purified on silica gel, eluting first with ethyl acetate/hexane (20%) followed with a gradient of dichloromethane/methanol (0 to 10%) to get 0.72 g of the N-unprotected peptide Phg-Val-OAllyl.

c) Z-Asp(β-tert-Butyl)-Phg-Val-OAllyl

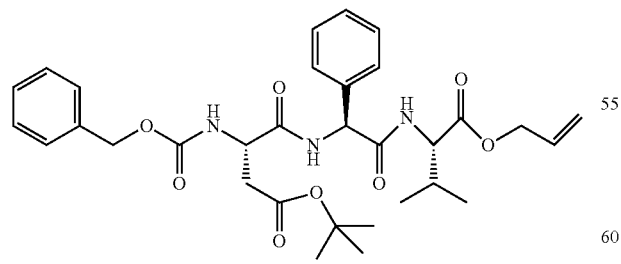

The Phg-Val-OAllyl (0.89 g, 2.74 mmol) was dissolved in anhydrous dichloromethane (7 ml). Then Z-Asp(β-tert-butyl)-OH (0.89 g, 2.74 mmol) in dichloromethane (2 ml) was added followed by diisopropyl carbodiimide (0.424 ml, 2.74 mmol). The mixture was stirred at RT for 2.45 hrs and then diluted with dichloromethane. The organic phase was washed twice with brine and dried over anhydrous magnesium sulphate. The solvent was evaporated and the obtained residue was purified on silica gel (gradient: ethyl acetate/hexane) to afford 0.4 g of Z-Asp(OtBu)-Phg-Val-OAllyl.

d) Z-Asp(β-tert-Butyl)-Phg-Val-OH

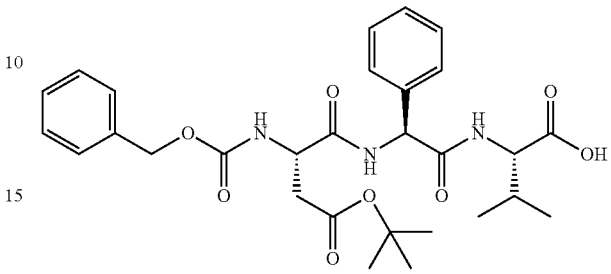

Z-Asp(β-tert-butyl)-Phg-Val-OAllyl (0.064 g; 0.107 mmol) was dissolved under argon in dry THF (3 ml, inhibitor free). The solvent was degassed three times under argon before adding morpholine (28 ul, 3 eq), followed by Tetrakis (13 mg). The mixture was stirred for 3.5 days at room temperature. The mixture was then concentrated under vacuum (12 mbar) and purified on silica gel (gradient methanol/dichloromethane: 1 to 14%) to afford 46 mg of the desired Z-Asp(β-tert-Butyl)-Phg-Val-OH.

NMR $^1$H (CD$_3$OD, 400 MHz) δ 7.43 (m, 2H); 7.34-7.26 (m, 8H); 5.57 (s, 1H); 5.10 (s, 2H); 4.60 (dd, J=8.28; 5.57 Hz, 1H); 4.24 (s, 1H); 2.81 (m, 1H); 2.58 (m, 1H); 1.41 (s, 9H); 0.96 (t, J=6 Hz, 6H).

LCMS negative (M-H)=554.2

Example 5

Synthesis of compound 20
Cbz-Asp(O-tBu)-Glu(O-tBu)-Val-OH

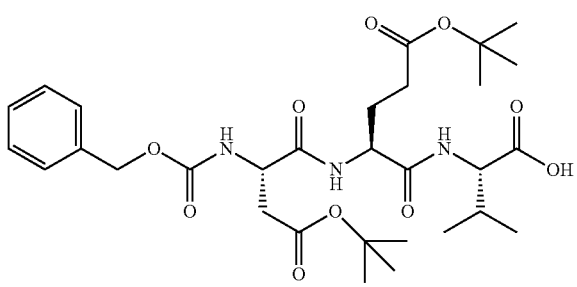 [SMILES: CC(C)[C@H](NC(=O)[C@H](CCC(=O)OC(C)(C)C)NC(=O)[C@H](CC(=O)OC(C)(C)C)NC(=O)OCc1ccccc1)C(=O)O]

a) Fmoc-Glu(O-tBu)-Val-OAllyl

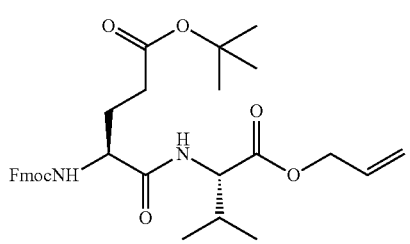

Fmoc-Glu (O-tBu)-OH (0.549 g, 1.292 mmol) was solvated in CH$_2$Cl$_2$ (5 mL) followed by addition of L-Val-allyl ester toluene-4-sulfonate (0.426 g, 1 eq), 4-methylmorpholine (0.145 mL, 1.02 eq), DMAP (11.53 mg, 0.13 eq) and finally EDC (0.252 g, 1.02 eq). The EDC vial was washed with CH$_2$Cl$_2$ (0.5 mL*2) and added to the reaction mixture. After 1 hour 10 min of stirring, the reaction mixture was extracted with CH$_2$Cl$_2$ (30 mL)/brine (5 mL). The organic layer was dried over MgSO$_4$, filtered off and concentrated. The obtained residue was purified on silica using a gradient Hex/EtOAc (0 to 40%) to get 0.396 g of the desired compound.

b) Glu(O-tBu)-Val-OAllyl

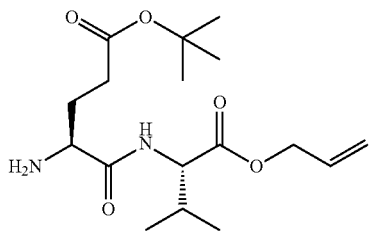 [SMILES: C=CCOC(=O)[C@@H](NC(=O)[C@@H](N)CCC(=O)OC(C)(C)C)C(C)C]

Fmoc-Glu(O-tBu)-Val(OAllyl) (0.394 g, 0.698 mmol) was solvated in CH$_2$Cl$_2$ (4 mL) followed by addition of piperidine (0.550 mL, 7.98 eq). After 40 min, the mixture was evaporated to dryness and co-evaporated with CH$_2$Cl$_2$ (20 mL*2) followed with high vacuum for 10 min to remove the excess of piperidine. The sample was purified on silica with a gradient of MeOH/CH$_2$Cl$_2$ (0 to 7%) to get 0.191 g of the desired compound.

c) Cbz-Asp(O-tBu)-Glu(O-tBu)-Val-OAllyl

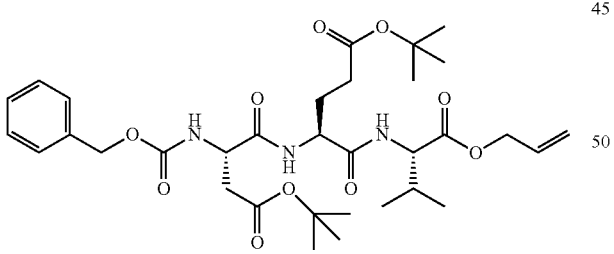

Glu-Val (OAllyl) (0.189 g, 0.55 mmol) was solvated in CH$_2$Cl$_2$ (2.5 ml) followed addition of Z-Asp (OtBu)-OH (0.187 g, 1.05 eq), DMAP (5.98 mg, 0.088 eq) and 4-methylmorpholine (0.065 ml, 1.07 eq), then EDC (0.109 g, 1.03 eq. The vial was rinsed with 0.5 ml of dichloromethane). The mixture was stirred for 2 hour at room temperature. Then it was extracted using CH$_2$Cl$_2$/brine. The organic layer was dried over MgSO$_4$, filtered off and concentrated. The obtained residue was purified on silica using a gradient EtOAc/Hex (10 to 100%) to get 0.300 g of the desired compound.

d) Cbz-Asp(O-tBu)-Glu(O-tBu)-Val-OH

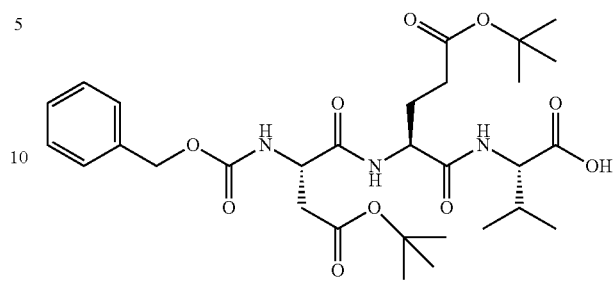

Cbz Asp (O-tBu)-Glu (OtBu)-Val-(OAllyl) (0.298 g, 0.46 mmol) was dissolved in THF (10 mL) and rotary evaporated to dryness, the sample was then redissolved in THF (10 mL) and vacuum aspirated (3*1 min of aspiration), followed by replacement of the atmosphere with Argon. Pd(PPh$_3$)$_4$ (0.052 g, 0.1 eq) was added in one shot, the flask was then evacuated with Argon. Morpholine (0.14 mL, 3.49 eq) was added and the flask covered with a tin foil. The mixture was kept under stirring for 2.5 days under Argon. The sample was evaporated to dryness and the obtained residue was subjected to purification on C$_{18}$ using a gradient MeOH/solution of H$_2$O at pH=3.5 (10 to 100%) to get 0.150 g of the desired compound.

NMR $^1$H (CD$_3$OD, 400 MHz) δ: 7.4-7.25 (m, 5H); 5.20-5.05 (m, 2H); 4.6-4.05 (m, 1H); 4.47-4.38 (m, 1H); 4.25-4.18 (m, 1H); 2.88-2.75 (m, 1H); 2.68-2.55 (m, 1H); 2.42-2.25 (m, 2H); 2.22-2.08 (m, 2H); 1.96-1.80 (m, 1H); 1.45 (2s, 18H); 0.93 (t, 6H).

Example 6

Synthesis of compound 23 (Asp (β-tert-butyl) Chlorovinyl-methyl vinyl sulfone tosyl salt)

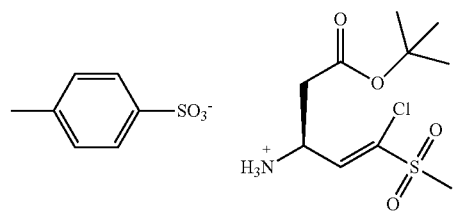

a) Diethyl chloro(methylsulfone) methylphosphonate

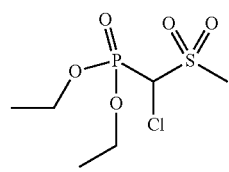

Diethyl (methylthio)methylphosphonate (1.45 g, 6.25 mmol) was solvated in acetic acid (5 mL, 14 eq) follow by addition of hydrogen peroxide (1.98 mL, 2.8 eq). The sample was then placed in a oil bath preheated to 70° C., vigour evolution of gas shortly followed. After 30 min the reaction was allowed to reach room temperature. Then NaHCO$_3$ was added in a small portion until the pH become neutral. The sample was then vacuum aspirated followed by extraction with Ether (30 mL). The organic layer was then washed with 20% of citric acid (5 mL) and then brine (2*5 mL). The organic layer was dried over MgSO$_4$ and purified on silica using a gradient EtOAc/Hexane (20 to 100%) to get 0.552 g of the desired compound.

NMR $^1$H (CDCl$_3$, 400 MHz) δ: 4.21-4.13 (m, 4H); 2.88-2.75 (m, 1H); 2.68 (d, 2H, J=12.83 Hz); 2.29 (s, 3H); 1.34 (t, 6H).

b) Boc-Asp (β-tert-butyl) αchlorovinyl methylsulfone

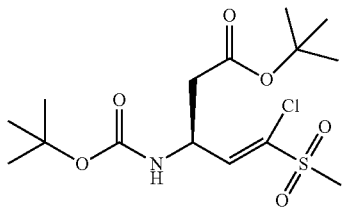 [SMILES: CC(C)(C)OC(=O)C[C@@H](/C=C(\Cl)S(C)(=O)=O)NC(=O)OC(C)(C)C]

Diethyl chloro(methylsulfone)methylphosphonate (0.327 g, 1.24 mmol) was solvated in THF (5 mL) and the solution was allowed to reach −78° C. NaH 60% (0.0519 g, 1.04 eq), which had been washed with Ether anhydrous (3*0.9 mL), was then added in suspension in THF (1.5 mL). The vial containing NaH in suspension was washed with THF (0.4 mL*2) and it was added to the solution. The mixture was stirred for 25 min, then Boc Asp (O-tBu)-H (0.326 g, 1 eq) solvated in THF (3 mL) was added dropwise to the solution over 1 min. The vial was rinsed with THF (0.3 mL*2) and added to the reaction mixture. After 45 min of stirring, the solution was quenched with a solution of saturated ammonium chloride (5 mL) and extracted with EtOAc (30 mL). The organic layer was washed with brine, dried over MgSO$_4$, filtered and concentrated. The residue was purified on silica using a gradient of EtOAc/Hex (0 to 40%) to get first the cis isomer and then 0.183 g of the trans isomer compound.

NMR $^1$H (CDCl$_3$, 400 MHz) δ: 7.1 (d, 1H, J=8.06 Hz); 5.5 (m, 1H); 4.8 (m, 1H); 3.05 (s, 3H); 2.62 (m, 2H); 1.45 (2s, 18H).

c) Asp(β-tert-butyl)αchlorovinyl methylsulfone tosyl salt

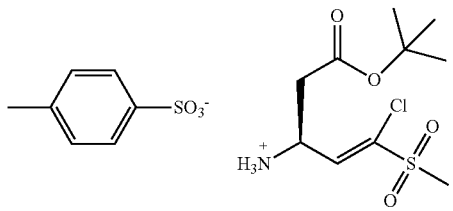

Boc-Asp (β-tert-butyl) Chlorovinyl-methyl vinyl sulfone (0.182 g, 0.4937 mmol) was solvated in CH$_2$Cl$_2$ (0.7 mL) followed by the addition of Et$_2$O (0.7 mL). p-Toluene sulfonic Acid monohydrate (0.101 g, 1.07 eq) was added in one shot. After 15 hours of stirring at room temperature, it was then diluted with Ether (8 mL) and filtered off. The while solid was then dried over vacuum, 0.12 g of the desired compound was obtained.

NMR $^1$H (DMSO, 400 MHz) δ: 8.2 (bs, 3H, NH$_3$); 7.48 (d, 2H, J=8.04 Hz); 7.12 (d, 2H, J=7.89 Hz); 7.02 (d, 1H, J=9.4 Hz); 4.4-4.3 (m, 1H); 3.2 (s, 3H); 2.85 (dd, 1H, J=16.39 Hz, J=5.55 Hz); 2.75 (dd, 1H, J=16.47 Hz, J=7.63 Hz); 2.28 (s, 3H); 1.42 (s, 9H).

Example 7

Synthesis of compound 26
(Asp(β-tert-butyl)αchlorovinyl phenylsulfone tosyl salt)

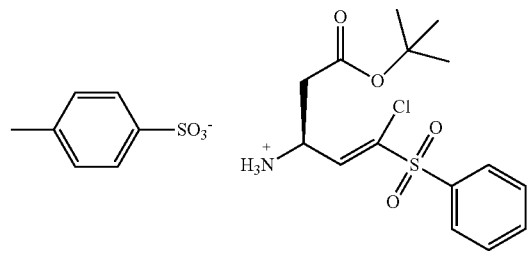

a) Diethyl chloro(phenylsulfone)methylphosphonate

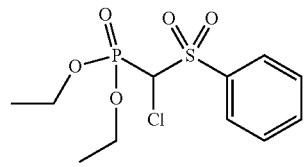 [SMILES: CCOP(=O)(OCC)C(Cl)S(=O)(=O)c1ccccc1]

Diethyl chloro(phenylthio)methylphosphonate (0.919 g, 3.12 mmol) was solvated in acetic acid (1.8 mL), followed by addition of hydrogen peroxide (0.78 mL, 2.8 eq). The sample was then placed in a oil bath preheated to 70° C. An additional portion of hydrogen peroxide (0.21 mL) was added after 5 min. After 30 min the reaction was allowed to reach room temperature. The sample was extracted with AcOEt/5% NaHCO$_3$ (30/5 mL). The organic layer was dried over MgSO$_4$, filtered and concentrated. The residue was purified on silica using a gradient EtOAc/Hexane (10 to 80%) to get 0.627 g of the desired compound.

b) Asp(β-tert-butyl)αchlorovinyl phenylsulfone

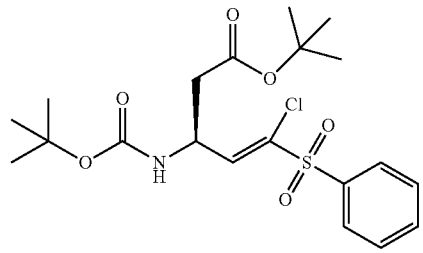 [SMILES: CC(C)(C)OC(=O)C[C@@H](/C=C(\Cl)S(=O)(=O)c1ccccc1)NC(=O)OC(C)(C)C]

Diethyl chloro(phenylsulfone)methylphosphonate (0.458 g, 1.03 eq) was solvated in THF (3 mL) and the solution was allowed to reach −78° C. NaH 60% (0.016 g, 1.11 eq), which had been washed with Ether anhydrous (3*0.9 mL), was then added in suspension in THF (1.5 mL). The vial containing NaH in suspension was washed with THF (0.4 mL*2) and added to the solution. The mixture was stirred for 25 min, then BocAsp(OtBu)-H (0.372 g, 1.36 mmol) solvated in THF (0.5 mL) was added dropwise to the solution over 1 min. The vial was rinsed with THF (2*0.5 ml) and added to the reaction mixture. After 45 min of stirring, the solution was quenched with a solution of ammonium chloride saturated (5 mL) and extracted with EtOAc (30 mL). The organic layer was washed with brine, dried over $MgSO_4$, filtered and concentrated. The residue was purified on silica using a gradient of Hex/EtOAc (0 to 30%), repurified using a gradient of $MeOH/CH_2Cl_2$ (0 to 3%) to elute first the cis product and then the trans product. Finally, a small amount of the desired compound was obtained.

NMR $^1H$ ($CDCl_3$, 400 MHz) δ: 8.13 (m, 2H); 7.67 (t, 1H, J=7.42 Hz); 7.57 (t, 2H); 6.55 (d, 1H, J=9.19 Hz); 5.75 (bs, 1H); 5.64 (bs, 1H); 2.86-2.77 (m, 2H); 1.47 (s, 9H); 1.45 (s, 9H).

c) Asp(β-tert-butyl)αchlorovinyl phenylsulfone tosyl salt

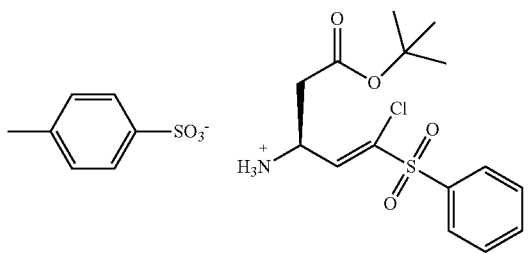

Asp(β-tert-butyl) αchlorovinyl phenylsulfone (0.018 g, 0.04 mmol) was solvated in $CH_2Cl_2$ (0.1 mL) followed by the addition of $Et_2O$ (0.1 mL). p-Toluene sulfonic Acid monohydrate (0.05 g, 0.1 eq) was added in one shot. After 15 hours of stirring at room temperature, it was then evaporated to dryness without heating to get 18 mg of the desired compound.

NMR $^1H$ (DMSO, 400 MHz) δ: 8.3 (s, 3H, $NH_3$); 8.08-8.02 (m, 2H); 7.8 (t, 1H, J=7.46 Hz); 7.76 (t, 2H, J=8.08 Hz); 7.48 (d, 2H, J=8.06 Hz); 7.1 (d, 2H, J=7.81 Hz); 6.73 (d, 1H, J=10.09 Hz); 5.3 (m, 1H); 2.87 (dd, 1H, J=16.67 Hz, J=6.13 Hz); 2.78 (dd, 1H, J=16.77 Hz, J=7.01 Hz); 2.28 (s, 3H); 1.43 (s, 9H).

Example 8

Synthesis of compound 30 (Asp(β-Methyl)methyl vinyl sulfone tosyl salt)

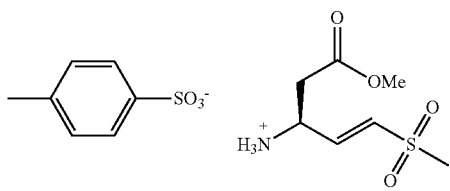

a) Boc-Asparamol(β-Methyl)

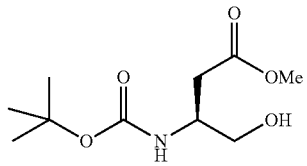 [SMILES: COC(=O)C[C@@H](CO)NC(=O)OC(C)(C)C]

a-Boc-L-Asp (β-Methyl)-OH (2.5 g, 0.0101 mol) was solvated in ethyl acetate (12.5 ml) and chilled at 0° c. N-hydroxysuccinimide (1.163 g, 1 eq) was added, followed with a dropwise addition of DCC (10.1 ml, 1 eq, 1M in $CH_2Cl_2$). The mixture was allowed to reach room temperature overnight (20 h), it was then diluted with ethyl acetate and filtered off on celite and washed with ethyl acetate (80 ml total volume). The organic layer was washed with 5% NaHCO3 (2*15 ml), brine (2*25 ml), dried over $MgSO_4$ and concentrated to dryness to get 3.58 g of the desired compound.

b-Boc-L-Asp (β-Methyl)-N-hydroxysuccinimide (1.81 g, 0.00526 mol) was dissolved in 24 mL of anhydrous THF under Argon. The mixture was chilled to 0° C., $NaBH_4$ (0.5 g, 2.51 eq) was added portion wise over a period of 25 min. The mixture was allowed to reach room temperature, and stirred for an extra 4 hours. A solution of ice water/brine (1/1, 15 mL) was added dropwise at 0° C. followed by caution addition of citric acid (0.5 M, 40 mL). The biphasic mixture was stirred and the product was extracted with EtOAc (4*40 mL). The combined organic layer were washed with 5% $NaHCO_3$ (15 mL) and brine (15 mL), dried over $MgSO_4$, filtered off and concentrated under vacuum. The crude material was then purified on silica with a gradient of $CH_2Cl_2$/MeOH (0 to 5%) to get 0.7 g of the desired compound.

NMR $^1H$ ($CDCl_3$, 400 MHz) δ: 5.20 (bs, 1H); 4.02-3.95 (m, 1H); 3.88-3.64 (m, 2H); 3.70 (s, 3H); 2.63 (d, 2H, J=5.86 Hz); 2.0 (bs, 1H, OH); 1.44 (s, 9H).

b) Boc-Asp(β-Methyl)-H

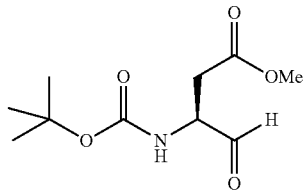 [SMILES: COC(=O)C[C@@H](C=O)NC(=O)OC(C)(C)C]

Oxalyl chloride 2M in $CH_2Cl_2$ (1.242 mL, 1.7 eq) dissolved in $CH_2Cl_2$ (2.4 mL) was cooled to −65° C. A solution of DMSO (0.4 mL, 3.9 eq) in $CH_2Cl_2$ (0.92 mL) was added dropwise over 20 min at −65° C. Boc Asp ($OCH_3$)—$CH_2OH$ in $CH_2Cl_2$ (2.6 mL) was added dropwise over a period of 20 min and the reaction was stirred for an extra 15 min at −65° C. TEA (1.33 mL, 6.54 eq) in $CH_2Cl_2$ (1.42 mL) was added dropwise over 20 min. The reaction was left for an extra 55 min at −65° C./−70° C. then quenched at this temperature with ether/0.5 N $KHSO_4$ (30/6 mL). The organic layer was washed 3 times with 0.5N $KHSO_4$ (3*6 mL) then brine, dried over $MgSO_4$, filtered off and concentrate, to get 0.29 g of the desired compound.

NMR ¹H (CDCl₃, 400 MHz) δ: 9.65 (s, 1H); 5.61 (d, 1H, J=7.04 Hz); 4.38-4.35 (q, 1H, J=4.3 Hz); 3.70 (s, 3H); 3.01 (dd, 1H, J=17.41 Hz, J=4.49 Hz); 2.83 (dd, 1H, J=17.41 Hz, J=4.69 Hz); 1.46 (s, 9H).

c) Boc-Asp(β-Methyl)methyl vinyl sulfone

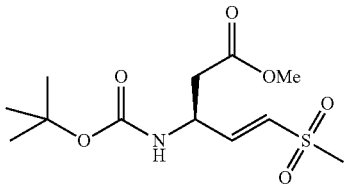 [SMILES: COC(=O)C[C@@H](/C=C/S(C)(=O)=O)NC(=O)OC(C)(C)C]

NaH 95% (0.038 g, 1.2 eq), which had been washed with Ether anhydrous (3*0.9 mL), was suspended in THF (1 mL). The NaH solution was added dropwise at 0° C. to Diethyl (methylsulfone) methylphosphonate (0.280 g, 1.08 eq) which was dissolved in a solution of THF (10 mL). The mixture was stirred for 20 min, then Boc Asp (OMethyl)-H (0.290 g, 1.255 mmol) solvated in THF (2.5 mL) was added dropwise to the solution over 1 min. After 15 min at 0° C., the reaction was allowed to reach room temperature. After 1 hour of stirring, the solution was quenched with a solution of saturated ammonium chloride (10 mL) and extracted with EtOAc (30 mL). The organic layer was washed with brine (20 mL), dried over MgSO₄, filtered and concentrate. The residue was purified on silica using a gradient of EtOAc/Hex (10 to 80%) to elute first the cis isomer then the trans isomer (0.174 g).

d) Boc-Asp(β-Methyl)methyl vinyl sulfone tosyl salt

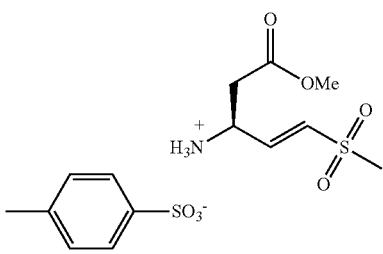

Boc-Asp(β-Methyl)methyl vinyl sulfone (0.172 g, 0.56 mmol) was solvated in CH₂Cl₂ (0.44 mL) followed by the addition of Et₂O (0.44 mL). p-Toluene sulfonic Acid monohydrate (0.19 g, 1.04 eq) was added in one shot. After 15 hours of stirring at room temperature, it was then diluted with Ether (2 mL) and filtered off. The while solid was then dried over vacuum, 0.140 g of the desired compound was obtained.

NMR ¹H (DMSO, 400 MHz) δ: 8.20 (bs, 3H, NH₃); 7.47-7.45 (m, 2H); 7.11 (dd, 2H, J=8.41 Hz, J=0.58 Hz); 7.03 (dd, 1H, J=15.45 Hz, J=1.17 Hz); 6.73 (dd, 1H, J=15.45 Hz, J=6.26 Hz); 4.34 (q, 1H, J=6.45 Hz); 3.66 (s, 3H); 3.05 (s, 3H); 2.92-2.82 (m, 2H); 2.28 (s, 3H).

Example 9

Synthesis of compound 33 (Asp(β-tert-butyl)methyl vinyl sulfone tosyl salt)

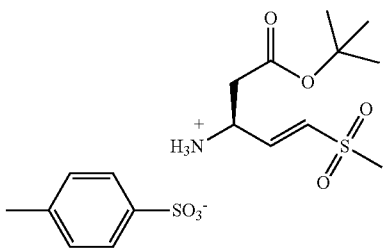

a) Diethyl (methylsulfone)methylphosphonate

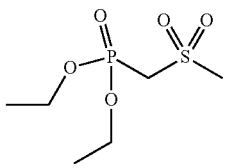

Diethyl (methylthio)methylphosphonate (4.0180 g, 20.3 mmol) was solvated in acetic acid (14 mL, 12 eq) follow by dropwise addition (10 min) of hydrogen peroxide (5.9 mL, 2.56 eq). The sample was then heated to 70° C., vigour evolution of gas shortly followed. After 25 min the reaction was allowed to reach room temperature. Then NaHCO₃ was added in a small portion until the pH become neutral. The sample was then vacuum aspirated followed by extraction with Ether. The organic layer was then washed with 20% of citric acid (5 mL) and then brine (2*10 mL). The organic layer was dried over MgSO₄ and purified on silica using a gradient EtOAc/Hexane (10 to 100%) to get 3.237 g of the desired compound.

NMR ¹H (DMSO, 400 MHz) δ: 4.18 (d, 2H, J=16.62 Hz); 4.10-4.03 (m, 4H); 3.10 (s, 3H); 1.23 (t, 6H, J=7.04 Hz).

b) Boc-Asp(β-tert-butyl)methyl vinyl sulfone

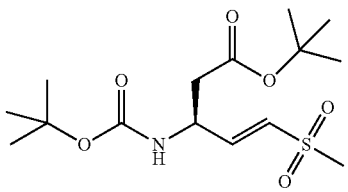 [SMILES: CC(C)(C)OC(=O)C[C@@H](/C=C/S(C)(=O)=O)NC(=O)OC(C)(C)C]

NaH 60% (0.087 g, 1.11 eq), which had been washed with Ether anhydrous (3*0.9 mL), was suspended in THF (1 mL). The NaH solution was added dropwise to Diethyl (methylsulfone)methylphosphonate (0.485 g, 1.08 eq) which was dissolved in a 0° C. solution of THF (20 mL). The mixture was stirred for 20 min, then Boc Asp (OtBu)-H (0.537 g, 1 eq) solvated in THF (2 mL) was added dropwise to the solution over 1 min. After 10 min at 0° C., the reaction was allowed to reach room temperature. After 1 hour of stirring, the solution was quenched with a solution of ammonium chloride saturated (45 mL) and extracted with EtOAc (100 mL). The organic layer was washed with brine (20 mL), dried over MgSO₄, filtered and concentrate. The residue was purified on silica using a gradient of Hex/EtOAc (10 to 80%) to elute 0.05 g of the cis compound and 0.480 g of the trans compound.

NMR $^1$H (CDCl₃, 400 MHz) δ: 6.86 (dd, 1H, J=15.08 Hz, J=4.60 Hz); 6.51 (dd, 1H, J=15.14 Hz, J=1.38 Hz); 5.41 (bs, 1H); 4.7 (bs, 1H); 2.91 (s, 3H); 2.64-2.52 (qd, 2H); 1.43 (s, 18H).

c) Asp(β-tert-butyl)methyl vinyl sulfone tosyl salt

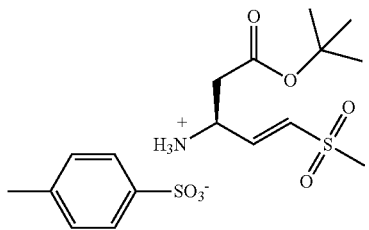

Boc-Asp(β-tert-butyl)methyl vinyl sulfone (0.158 g, 0.4534 mmol) was solvated in CH₂Cl₂ (0.7 mL) followed by the addition of Et₂O (0.7 mL). p-Toluene sulfonic Acid monohydrate (0.0878 g, 1.02 eq) was added in one shot. The use of excess of PTSA hydrate cleaves both boc and tert-butyl groups unlike what was reported by Palmer. After 15 hours of stirring at room temperature, it was then diluted with Ether (5 mL) and filtered off. The while solid was then dried over vacuum, 0.121 g of the desired compound was obtained.

NMR $^1$H (DMSO, 400 MHz) δ: 8.18 (bs, 3H, NH₃); 7.47 (d, 2H, J=8.14 Hz); 7.10 (d, 2H, J=7.85 Hz); 7.02 (d, 1H, J=15.42 Hz); 6.70 (dd, 1H, J=15.40 Hz, J=6.61 Hz); 4.27 (q, 1H, J=6.3 Hz); 3.04 (s, 3H); 2.81-2.70 (qd, 2H); 2.28 (s, 3H); 1.42 (s, 9H).

Example 10

Synthesis of Compound 37 (Asp-Vinyl Phenyl Sulfone Salt Form)

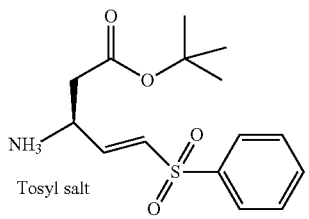

The commercially available N-tBoc-L-Asp(β-tert-Butyl)-O-succinimide was reduced to the corresponding alcohol in the presence of sodium borohydride in THF, as described in the literature (Ramond J. Begeron et al., 1999)

a) Boc-Asp(β-tert-Butyl)-H

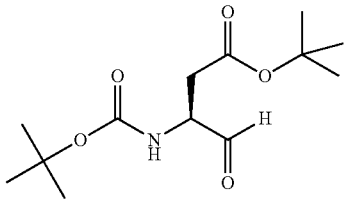 [SMILES: CC(C)(C)OC(=O)C[C@@H](C=O)NC(=O)OC(C)(C)C]

The alcohol is then oxidized to the corresponding Boc-L-Asp(β-tert-Butyl)-H in the presence of oxalyl chloride, DMSO and TEA in dichloromethane at −70° C. as described in the literature (William R. Ewing et al., 1999; Won Bum Jang. 2004 and Mancuso A et al., 1981)

b) Diethyl phenylsulfonylmethylphosphonate

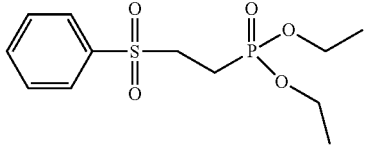 [SMILES: CCOP(=O)(CCS(=O)(=O)c1ccccc1)OCC]

The precursor of phenyl vinyl sulfone was obtained in one step from benzenesulfonyl fluoride and triethyl phosphorane in the presence of lithium hexamethyldisilazide at −78° C. to get diethyl phenylsulfonylmethylphosphonate as described in the literature (Won Bum Jang et al., 1998).

Boc-Asp(β-tert-Butyl)-vinyl phenyl sulfone (Gang Wang et al., 2003; Marion G. Gotz et al., 2004; Palmer, James T et al., 1995).

c) Boc-Asp-vinyl phenyl sulfone

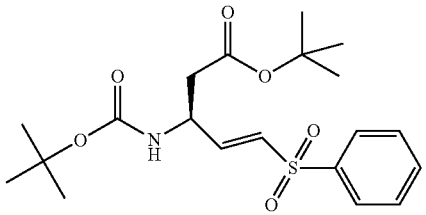 [SMILES: CC(C)(C)OC(=O)C[C@@H](/C=C/S(=O)(=O)c1ccccc1)NC(=O)OC(C)(C)C]

Sodium hydride (40 mg (60%), 1.09 eq) was added to a solution of diethyl phenylsulfonylmethylphosphonate (0.279 g, 1.09 eq) in dry THF (5.6 ml) at 0° C. The mixture was stirred for 20 minutes before adding, drop-wise, a solution of Boc-L-Asp(O-t-Bu)-H (0.24 g, 0.876 mmol) in 1.6 ml of THF. The mixture was stirred for 1.15 h at RT, then poured into a mix of ethyl acetate and ammonium chloride saturated solution (45/15 ml). The organic layer was dried over magnesium sulfate and the solvent was evaporated to dryness. The crude material was purified on silica gel (gradient: ethyl acetate/hexane) to make the desired compound with a high chemical yield.

NMR $^1$H (CD₃OD, 400 MHz) δ 7.87 (d, J=7.62 Hz, 2H); 7.61 (t, J=7.35 Hz, 1H); 7.53 (t, J=7.68 Hz, 2H); 6.92 (dd, J=15.08 and 4.28 Hz, 1H); 6.46 (d, J=15.12 Hz, 1H); 5.34 (m, 1H); 4.68 (m, 1H); 2.63-2.52 (m, 2H); 1.40 (s, 18H).

d) AspVinyl phenyl sulfone tosyl salt

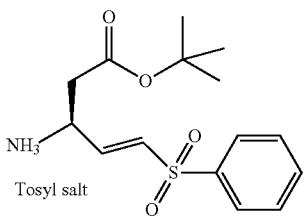 [SMILES: CC(C)(C)OC(=O)C[C@H](N)/C=C/S(=O)(=O)c1ccccc1]

Boc-L-Asp(β-tert-Butyl)-Vinyl phenyl sulfone (0.1 g, 0.243 mmol) was dissolved in a mix of dichloromethane and ether (0.7/0.7 ml), then PTSA hydrate (1 eq) was added. The use of excess of PTSA hydrate cleaves both boc and tert-butyl groups unlike what was reported by Palmer. The mixture was stirred at room temperature overnight. Then, it was diluted with ether (8 ml). The white precipitate was filtered off and dried to yield to the desired compound as a white powder.

Example 11

Synthesis of compound 40 (Asp(β-tert-butyl)phenoxy vinylsulfone tosyl salt)

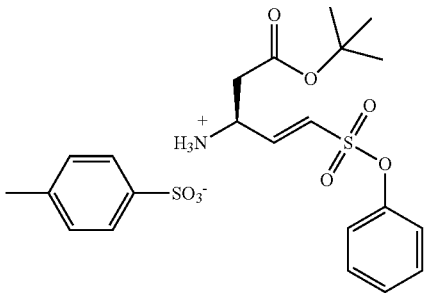

To a solution of phenol (1.62 g, 17.2 mmol) in Et$_2$O (50 mL) at –10° C. was added TEA (3.6 mL, 1.5 eq). After 15 min a solution of methanesulfonylchloride (1.6 mL, 1.2 eq) in Et$_2$O (4 mL) was added dropwise over 50 min. Then the solution was allowed to warm at room temperature and an additional portion of Et$_2$O (5 mL) was added. The reaction was quenched by addition of 1N HCl (12 mL, 4 C), the organic layer was then washed with saturated NaHCO$_3$, brine and dried over MgSO$_4$, filtered off and concentrate to give an oil which was recristallised for CH$_2$Cl$_2$/Hex (1/1). The resulting solid was filtered and the residual solvent removed.

a) Diethyl (phenoxysulfone)methylphosphonate

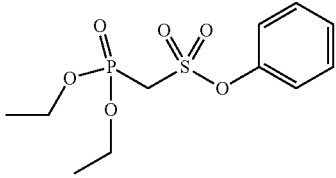 [SMILES: CCOP(=O)(CS(=O)(=O)Oc1ccccc1)OCC]

To a solution of methanesulfonyl phenoxy (1.938 g, 11.25 mmol) in THF (8 mL) at –78° C., was added dropwise a solution of potassium bis(trimethylsilyl)amide (2.36 g, 1 eq) in 11 mL of THF over a period of 40 min. Then the reaction was stirred for an extra 5 min. Diethyl chlorophosphonate (0.95 mL, 0.59 eq) was added dropwise over 7 min. After 1 hour, the reaction was quenched by dropwise addition of a solution of Acetic Acid (0.645 mL, 0.59 eq) over 5 min. The solution was allowed to warm to room temperature and the solvent was removed in vacuum. The product was extract with CH$_2$Cl$_2$ (30 mL) and H$_2$O (10 mL), dried over MgSO$_4$, filtered off and concentrate. The residue was purified on silica using a gradient EtOAc/Hexane (12 to 100%) to get 1.046 g of the desired compound.

NMR $^1$H (CDCl$_3$, 400 MHz) δ: 7.44-7.41 (m, 2H); 7.36-7.32 (m, 3H); 4.31-4.25 (m, 4H); 3.81 (d, 2H, J=17.14 Hz); 1.38 (t, 6H, J=7.11 Hz).

b) Asp(β-tert-butyl)phenoxy vinyl sulfone

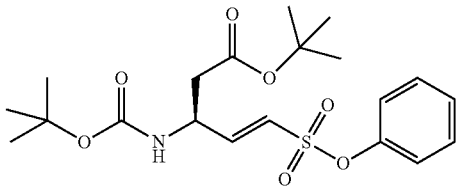 [SMILES: CC(C)(C)OC(=O)C[C@@H](/C=C/S(=O)(=O)Oc1ccccc1)NC(=O)OC(C)(C)C]

Diethyl (phenoxysulfone)methylphosphonate (0.36 g, 1.07 mmol) was solvated in THF (10 mL) and the solution was allowed to reach –0° C. NaH 60% (0.0539 g, 1.22 eq), which had been washed with Ether anhydrous (3*0.9 mL), was then added in suspension in THF (1 mL). The vial containing NaH in suspension was washed with THF (1 mL) and it was added to the solution. The mixture was stirred for 20 min, then Boc Asp (O-tBu)-H (0.30 g, 1 eq) solvated in THF (2 mL) was added dropwise to the solution over 1 min. The vial was rinsed with THF (1 mL) and added to the reaction mixture. After 2 hours of stirring at room temperature, the solution was quenched with a solution of ammonium chloride saturated (5 mL) and extracted with EtOAc (30 mL). The organic layer was washed with brine, dried over MgSO$_4$, filtered off and concentrated. The residue was purified on silica using a gradient of EtOAc/Hexane (0 to 30%, 30 to 80%) to get 0.359 g of the desired compound.

NMR $^1$H (CDCl$_3$, 400 MHz) δ: 7.38 (t, 2H, J=7.96 Hz); 7.29 (t, 1H, J=7.46 Hz); 7.23-7.21 (m, 2H); 6.79 (dd, 1H, J=15.14 Hz, J=4.67 Hz); 6.49 (dd, 1H, J=15.18 Hz, J=1.31 Hz); 5.37 (bs, 1H); 4.65 (bs, 1H); 2.60 (dd, 1H, J=16.04 Hz, J=5.46 Hz); 2.50 (dd, 1H, J=16.04 Hz, J=5.63 Hz); 1.46 (s, 9H); 1.43 (s, 9H).

c) Asp(β-tert-butyl)phenoxy vinyl sulfone tosyl salt

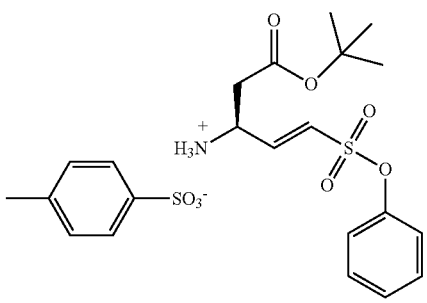

Asp(β-tert-butyl)phenoxy vinyl sulfone (0.187 g, 0.444 mmol) was solvated in CH$_2$Cl$_2$ (0.7 mL) followed by the addition of Et$_2$O (0.7 mL). p-Toluene sulfonic Acid monohydrate (0.084 g, 1.01 eq) was added in one shot. After 15 hours of stirring at room temperature, it was then diluted with Ether (8 mL) and filtered off. The while solid was then dried over vacuum to get the desired compound.

NMR $^1$H (DMSO, 400 MHz) δ: 8.25 (bs, 3H, NH$_3$); 7.49-7.46 (m, 4H); 7.39 (t, 1H, J=7.4 Hz); 7.31-7.29 (m, 2H); 7.22-7.17 (m, 1H); 7.10 (d, 2H, J=7.88 Hz); 6.82 (dd, 1H, J=15.41 Hz, J=6.15 Hz); 4.35 (m, 1H); 2.82-2.73 (m, 2H); 2.28 (s, 3H); 1.41 (s, 9H).

Example 12

Synthesis of compound 43 (Asp(β-tert-butyl) isopropyl vinyl sulfone tosyl salt)

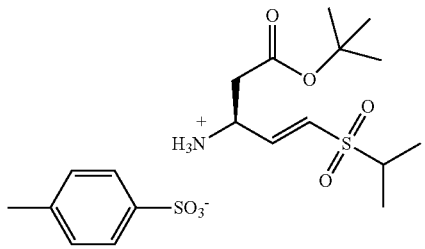

Chloromethyl isopropylsulfide (12.54 g, 100.6 mmol) was heated to 110° C. follow by dropwise addition of triethylphosphonyl (21 mL, 1.10 eq). After stirring for 8 hours, the reaction was allowed to reach to room temperature. The sample was purified by distillation (110° C./6 mmbar) to get 4.7 g of Diethyl (isopropylthio)methylphosphonate.

NMR $^1$H (CDCl$_3$, 400 MHz) δ: 4.21-4.13 (m, 4H); 3.19-3.14 (m, 1H); 2.76 (d, 2H, J=14.35 Hz); 1.34-1.27 (m, 12H).

Example 13

Synthesis of compound 41 (Diethyl (isopropylsulfone) methylphosphonate)

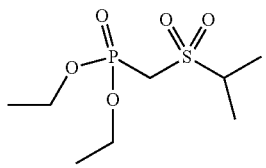

Diethyl (isopropylthio)methylphosphonate (4.746 g, 0.02 mol) was solvated in acetic acid (14.5 mL, 12.06 eq) followed by dropwise addition over 5 min of hydrogen peroxide (6 mL, 2.52 eq). The sample was then heated to 70° C., vigor evolution of gas shortly followed. After 30 min the reaction was allowed to reach room temperature. Then NaHCO$_3$ was added in a small portion until the pH become neutral. The sample was then vacuum aspirated followed by extraction with Ether (30 mL). The organic layer was then washed with 20% of citric acid (5 mL) and then brine (2*10 mL). The organic layer was combined and extract with CH$_2$Cl$_2$/water, dried over MgSO$_4$ and purified on silica using a gradient EtOAc/Hexane (20 to 100%) to get 4.689 g of the desired compound.

NMR $^1$H (CDCl$_3$, 400 MHz) δ: 4.23-4.50 (m, 4H); 3.67-3.63 (m, 1H); 3.53 (d, 2H, J=16.82 Hz); 1.37-1.30 (m, 12H).

Example 14

Synthesis of compound 42 (BocAsp(β-tert-butyl) isopropyl vinyl sulfone)

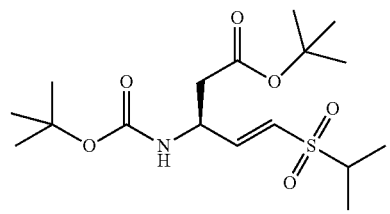 [SMILES: CC(C)S(=O)(=O)/C=C/[C@H](CC(=O)OC(C)(C)C)NC(=O)OC(C)(C)C]

Diethyl (isopropylsulfone)methylphosphonate (0.036 g, 0.1427 mmol) was solvated in THF (0.2 mL) and the solution was allowed to reach 0° C. NaH 60% (5.38 mg, 1.05 eq), which had been washed with Ether anhydrous (3*0.9 mL), was then added in suspension in THF (1.2 mL). The mixture was stirred for 25 min, then Boc Asp (O-tBu)-H (0.0351 g, 1 eq) solvated in THF (0.6 mL) was added dropwise to the solution over 1 min. After 45 min of stirring, the solution was quenched with a solution of ammonium chloride saturated (2 mL) and extracted with EtOAc (10 mL). The organic layer was washed with brine, dried over MgSO$_4$, filtered and concentrated. The residue was purified on silica using a gradient of EtOAc/Hexane (5 to 60%) to get 29.3 mg of the desired compound.

NMR $^1$H (CDCl$_3$, 400 MHz) δ: 6.82 (dd, 1H, J=15.24 Hz, J=4.78 Hz); 6.38 (dd, 1H, J=15.17 Hz, J=1.41 Hz); 5.43 (m, 1H); 4.67 (s, 1H); 3.07-3.0 (m, 1H); 2.64 (dd, 1H, J=16.07 Hz, J=5.5 Hz); 2.57 (dd, 1H, J=16.12 Hz, J=5.52 Hz); 1.48-1.32 (m, 24H).

Example 15

Synthesis of compound 43 (Asp(β-tert-butyl)isopropyl vinyl sulfone tosyl salt)

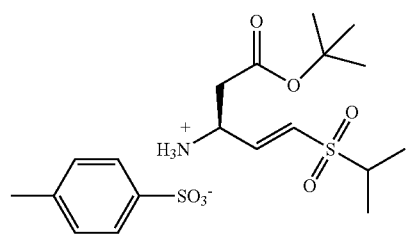

Boc-Asp(β-tert-butyl) isopropyl vinyl sulfone (0.028 g, 0.0741 mmol) was solvated in CH$_2$Cl$_2$ (0.2 mL) followed by the addition of Et$_2$O (0.2 mL). p-Toluene sulfonic Acid monohydrate (0.0154 g, 1.09 eq) was added in one shot. After 15 hours of stirring at room temperature, it was then diluted with Ether (8 mL) and filtered off. The while solid was then dried over vacuum, 11 mg of the desired compound was obtained.

NMR ¹H (DMSO, 400 MHz) δ: 8.21 (bs, 3H, NH₃); 7.46 (d, 2H, J=7.81 Hz); 7.10 (d, 2H, J=7.85 Hz); 6.92-6.85 (m, 1H); 6.71 (dd, 1H, J=15.42 Hz, J=6.34 Hz); 4.30 (m, 1H); 3.23-3.13 (m, 1H); 2.85-2.72 (m, 2H); 2.28 (s, 3H); 1.42 (s, 9H); 1.21 (m, 6H).

Example 16

Synthesis of compound 46 (Asp(β-tert-butyl) morpholine vinyl sulfone tosyl salt)

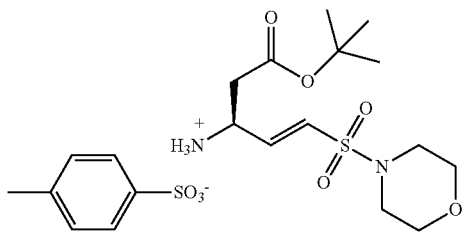

To a solution of morpholine (1.4 mL, 16.07 mmol) in CH₂Cl₂ (30 mL) at −10° C. was added TEA (3.4 mL, 1.5 eq). After 15 min a solution of methanesulfonylchloride (1.5 mL, 1.2 eq) in CH₂Cl₂ (4 mL) was added dropwise over 40 min. Then the solution was allowed to warm at room temperature and an additional portion of Et₂O (5 mL) was added. The reaction was quenched by addition of 1N HCl (12 mL, 4 C), the organic layer was then washed with saturated NaHCO₃, brine and dried over MgSO₄, filtered off and concentrate to give an oil which was purified on silica using a gradient of MeOH/CH₂Cl₂ (0 to 5%) to get 0.831 g of Diethyl (morpholinethio)methylphosphonate.

Example 16

Synthesis of compound 44 (Diethyl (morpholinesulfone)methylphosphonate)

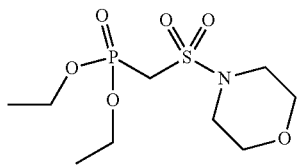 [SMILES: CCOP(=O)(CS(=O)(=O)N1CCOCC1)OCC]

To a solution of methane sulfonyl morpholine (0.719 g, 4.356 mmol) in THF (4 mL) at −78° C., was added dropwise a solution of potassium bis(trimethylsilyl)amide (0.748 g, 0.86 eq) in 11 mL of THF over a period of 40 min. Then the reaction was stirred for an extra 5 min. Diethyl chloromethylphosphonate (0.37 mL, 0.57 eq) was added dropwise over 7 min. After 1 hour, the reaction was quenched by dropwise addition of a solution of Acetic Acid (0.226 mL, 0.77 eq) over 5 min. The solution was allowed to warm to room temperature and the solvent was removed in vacuum. The product was extract with CH₂Cl₂ (30 mL) and H₂O (10 mL), dried over MgSO₄, filtered off and concentrate. The residue was purified on silica using a gradient MeOH/CH₂Cl₂ (0 to 4%) to get 0.247 g of the desired compound.

NMR ¹H (CDCl₃, 400 MHz) δ: 4.26-4.20 (m, 4H); 3.76 (t, 4H, J=4.6 Hz); 3.51 (d, 2H, J=17.33 Hz); 3.34 (t, 4H, J=4.74 Hz); 1.37 (t, 6H, J=7.11 Hz).

Example 17

Synthesis of compound 45 (Boc-Asp(β-tert-butyl)morpholine vinyl sulfone)

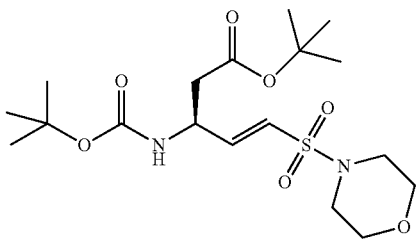 [SMILES: CC(C)(C)OC(=O)C[C@@H](/C=C/S(=O)(=O)N1CCOCC1)NC(=O)OC(C)(C)C]

Diethyl (morpholinesulfone)methylphosphonate (0.103 g, 1.07 mmol) was solvated in THF (1 mL) and the solution was allowed to reach −10° C. NaH 60% (0.013 g, 1.04 eq), which had been washed with Ether anhydrous (3*0.9 mL), was then added in suspension in THF (1 mL). The vial containing NaH in suspension was washed with THF (0.5 mL) and it was added to the solution. The mixture was stirred for 20 min, then Boc Asp (OtBu)-H (0.208 g, 1 eq) solvated in THF (1.5 mL) was added dropwise to the solution over 1 min, the vial was washed with DMF (0.5 ml) and added to the solution. After 3 hours of stirring at room temperature, the solution was quenched with a solution of ammonium chloride saturated (5 mL) and extracted with EtOAc (30 mL). The organic layer was washed with brine, dried over MgSO4, filtered off and concentrated. The residue was purified on silica using a gradient of first Hex/EtOAc (5 to 80%) then CH₂Cl₂/MeOH (0 to 10%) to get 0.075 g of the desired compound.

Example 18

Synthesis of compound 46 (Asp(β-tert-butyl)morpholine vinyl sulfone tosyl salt)

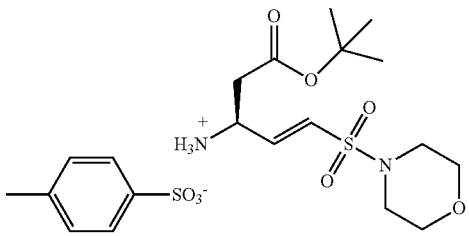

Boc-Asp(β-tert-butyl) morpholine vinyl sulfone (0.075 g, 0.178 mmol) was solvated in CH₂Cl₂ (0.2 mL) followed by the addition of Et₂O (0.2 mL). p-Toluene sulfonic Acid monohydrate (0.034 g, 1.0 eq) was added in one shot. After 15 hours of stirring at room temperature, it was then diluted with Ether (0.5 mL) and filtered off. The while solid was then dried over vacuum, 0.045 g of the desired compound was obtained.

NMR ¹H (DMSO, 400 MHz) δ: 8.20 (bs, 3H, NH₃); 7.47 (d, 2H, J=7.9 Hz); 7.10 (d, 2H, J=7.89 Hz); 6.88 (d, 1H, J=15.33 Hz); 6.60 (dd, 1H, J=15.00 Hz, J=6.36 Hz); 4.28 (s, 1H); 3.65 (t, 4H, J=4.43 Hz); 3.02 (m, 4H); 2.84-2.76 (m, 2H); 2.28 (s, 3H); 1.42 (s, 9H).

Example 18

Synthesis of compound 47 (Z-Asp(β-tert-Butyl)-Ala(2'-quinolyl)-Val-Asp(β-tert-Butyl)αchlorovinyl methylsulfone)

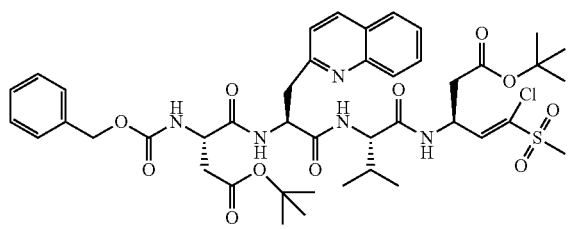 [SMILES: CC(C)[C@H](NC(=O)[C@H](Cc1ccc2ccccc2n1)NC(=O)[C@H](CC(=O)OC(C)(C)C)NC(=O)OCc1ccccc1)C(=O)N[C@H](/C=C(\Cl)S(C)(=O)=O)CC(=O)OC(C)(C)C]

The Z-Asp(β-tert-Butyl)-Ala(2'-quinolyl)-Val-OH (18 mg, 0.029 mmol) is dissolved in a mix of dichloromethane and DMF (0.39 ml/0.13 ml). The mixture was allowed to reach −15/−20° C. before adding N-methyl morpholine (8 µl) followed 3 min latter with isobutyl chloroformate (7 µl). The mixture was stirred at −15° C. for 10 minutes. Next, Asp (β-tert-butyl) αchloromethyl-methylsulfone tosyl salt (13 mg, 1 eq) was added in one shot, followed by N-methyl morpholine (8 µl). The mixture was stirred 35 minutes at −15/−20° C. and then diluted with 5 ml of dichloromethane and quenched with 1.5 ml of a saturated solution of sodium bicarbonate. The organic layer was dried over magnesium sulphate, the solvent was evaporated to dryness. The obtained residue was purified on silica gel (gradient: ethyl acetate/hexane: 5 to 100%) to afford 12 mg of the desired compound.

Example 19

Synthesis of compound 48 (Z-Asp-Ala(2'-quinolyl)-Val-Asp-αchlorovinyl methylsulfone)

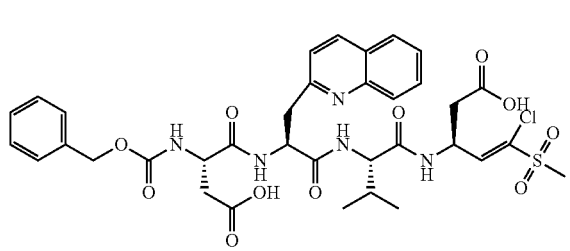 [SMILES: CC(C)[C@H](NC(=O)[C@H](Cc1ccc2ccccc2n1)NC(=O)[C@H](CC(=O)O)NC(=O)OCc1ccccc1)C(=O)N[C@H](/C=C(\Cl)S(C)(=O)=O)CC(=O)O]

Z-Asp(β-tert-Butyl)-Ala(2'-quinolyl)-Val-Asp(β-tert-Butyl)-αchlorovinyl methylsulfone (11.7 mg) was dissolved in dichloromethane (0.24 ml), followed by addition of trifluoroacetic acid (0.35 ml). The mixture was stirred at room temperature overnight (15 h). It was then quenched with diethyl ether (5 ml), the solvent was removed under vacuum. The obtained residue was diluted again with ether (5 ml) and the process was repeated twice. The precipitate was washed with 2*1 ml of ether, dried to give 9 mg of the desired compound.

NMR $^1$H (CD$_3$OD, 400 MHz) δ: 8.6-7.25 (m, 11H); 7.07 (d, 1H, J=8.61 Hz); 5.03-4.06 (m, 4H); 4.45-4.42 (m, 1H); 4.09-4.05 (m, 1H); 3.65-3.49 (m, 2H); 3.07 (s, 3H); 2.84-2.7 (m, 2H); 2.71-2.66 (m, 2H); 2.00 (m, 1H); 0.85 (t, 6H, J=8.2 Hz).

LCMS (M-H+)=772.4.

Example 20

Synthesis of compound 49 (Ts-Ala(2'quinolyl)-Val-Asp(β-tert-Butyl)-αchlorovinyl methylsulfone)

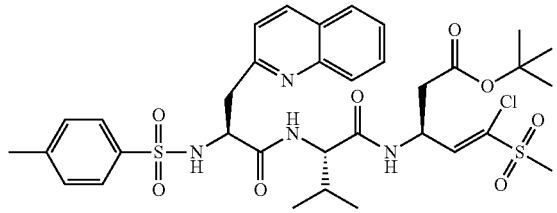

The Ts-Ala (2'-quinolyl)-OH (5.6 mg, 0.0123 mmol) was dissolved in a mix of CH$_2$Cl$_2$/DMF (0.15/0.13 mL). The mixture was allowed to reach −15° C./−20° C. (ice MeOH bath) before adding NMM (0.004 mL) followed 3 min later with isobutylchloroformate (0.004 mL). The mixture was stirred for 10 min at −15° C. before adding Asp (β-tert-butyl) Chlorovinyl-methyl vinyl sulfone tosyl salt (6.3 mg, 1 eq) in one shot, followed with 4-methylmorpholine (0.004 mL). The mixture was stirred at −15° C./−20° C. for 30 min, it was then diluted with CH$_2$Cl$_2$ (5 mL), then water (2 mL) and the mixture was allowed to reach room temperature, extracted. The organic layer was dried over MgSO$_4$, concentrated and purified by silica using Hex/EtOAc (15 to 100%) to get 6 mg of the desired compound.

Example 21

Synthesis of compound 50 (Ts-Ala(2'quinolyl)-Val-Asp-αchlorovinyl methylsulfone)

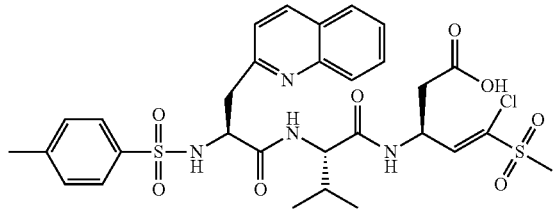

Ts-Ala(2'quinolyl)-Val-Asp(β-tert-Butyl)-αchlorovinyl methylsulfone (6 mg) was dissolved in dichloromethane (0.15 ml), followed by addition of trifluoroacetic acid (0.2 ml). The mixture was stirred at room temperature overnight (15 h). It was then quenched with diethyl ether (5 ml) and the solvent was removed under vacuum. The obtained residue was diluted again with ether and the process was repeated twice. The precipitate was washed with 2*1 ml of ether, dried to give 4 mg of the desired compound.

NMR $^1$H (CD$_3$OD, 400 MHz) δ: 8.37 (m, 1H); 8.01-7.99 (m, 1H); 7.96-7.94 (m, 1H); 7.90-7.94 (m, 1H); 7.90-7.88 (m, 1H); 7.71-7.63 (m, 1H); 7.46 (m, 1H); 7.37 (d, 2H, J=8.22 Hz); 7.08 (d, 1H, J=8.46 Hz); 6.88 (d, 2H, J=8.0 Hz); 5.04-5.01 (m, 1H); 4.37-4.34 (m, 1H); 4.08-4.07 (m, 1H); 3.44-3.4 (m, 1H); 3.2 (m, 1H); 3.08 (s, 3H); 2.83-2.78 (m, 1H); 2.73-2.684 (m, 1H); 2.17 (s, 3H); 2.07-2.03 (m, 1H); 0.91-0.89 (m, 6H).

Example 22

Synthesis of compound 51 (Z-Asp(1'-methyl)-Indanylglycine-Val-Asp(β-methyl)methyl vinyl sulfone)

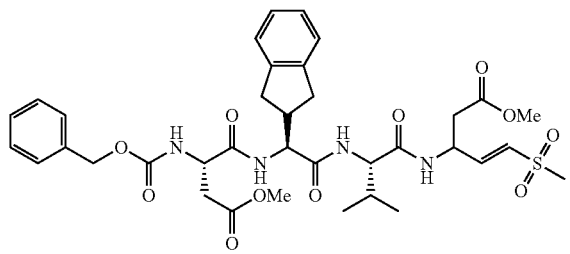 [SMILES: COC(=O)CC(/C=C/S(C)(=O)=O)NC(=O)[C@@H](NC(=O)[C@@H](NC(=O)[C@H](CC(=O)OC)NC(=O)OCc1ccccc1)C1Cc2ccccc2C1)C(C)C]

The Z-Asp(β-methyl)-Indanylglycine-Val-OH (16.7 mg, 0.0301 mmol) is dissolved in a mix of THF and DMF (0.5 ml/0.1 ml). The mixture was allowed to reach −15/−20° C. before adding N-methyl morpholine (9 µl) followed 3 min latter with isobutyl chloroformate (8 µl). The mixture was stirred at −15° C. for 10 minutes. Next, Asp (β-methyl) methyl vinyl sulfone tosyl salt (12 mg, 1 eq) was added in one shot, the vial was washed with THF (0.1 ml) and added to the solution, followed by the addition of N-methyl morpholine (9 µl). The mixture was stirred 35 minutes at −15/−20° C. and then diluted with 7 ml of dichloromethane and quenched with 1.5 ml of a saturated solution of sodium bicarbonate. After that, the organic layer was dried over magnesium sulphate. The solvent was evaporated to dryness. The obtained residue was purified on silica gel (ethyl acetate/hexane: 40% then dichloromethane/methanol: 5 to 15%) to afford 14 mg of Z-Asp(β-methyl)-Indanylglycine-Val-Asp(β-methyl)-methyl vinyl sulfone.

NMR $^1$H (DMSO, 400 MHz) δ: 8.31 (d, NH, J=7.82 Hz); 8.11 (d, NH, J=8.8 Hz); 7.93 (d, NH, J=8.21 Hz); 7.69 (d, NH, J=8.02 Hz); 7.37-7.08 (m, 9H); 6.74 (dd, 1H, J=15.45 Hz, J=4.30 Hz); 6.67 (d, 1H, J=15.59 Hz); 5.05 (s, 2H); 4.99 (m, 1H); 4.44 (m, 2H); 4.11 (m, 1H); 3.57 (s, 6H); 2.98 (s, 3H); 2.95-2.5 (m, 9H); 2.00-1.94 (m, 1H); 0.84 (t, 6H, J=6.06 Hz).

Example 23

Synthesis of compound 52 (Z-Asp(β-tert-Butyl)-Phg-Val-Asp(β-tert-Butyl)methyl vinyl sulfone)

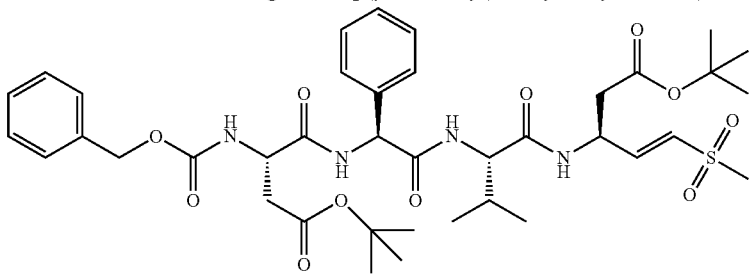

The Z-Asp(β-tert-Butyl)-Phg-Val-OH (17 mg, 0.0306 mmol) is dissolved in a mix of dichloromethane and DMF (0.39 ml/0.13 ml). The mixture was allowed to reach −15/−20° C. before adding N-methyl morpholine (8 nl) followed 3 min latter with isobutyl chloroformate (8 µl). The mixture was stirred at −15° C. for 10 minutes. Next, Asp (β-tert-butyl)methyl vinyl sulfone tosyl salt (12 mg, 1 eq) was added in one shot, followed by N-methyl morpholine (8 µl). The mixture was stirred 35 minutes at −15/−20° C. and then diluted with 5 ml of dichloromethane and quenched with 1.5 ml of a saturated solution of sodium bicarbonate. The organic layer was dried over magnesium sulphate. The solvent was evaporated to dryness. The obtained residue was purified on silica gel (gradient: ethyl acetate/hexane: 5 to 100%) to afford 8 mg of Z-Asp(β-tert-Butyl)-Phg-Val-Asp (β-tert-butyl)-methyl vinyl sulfone.

Example 24

Synthesis of compound 53
(Z-Asp-Phg-Val-Asp-methyl vinyl sulfone)

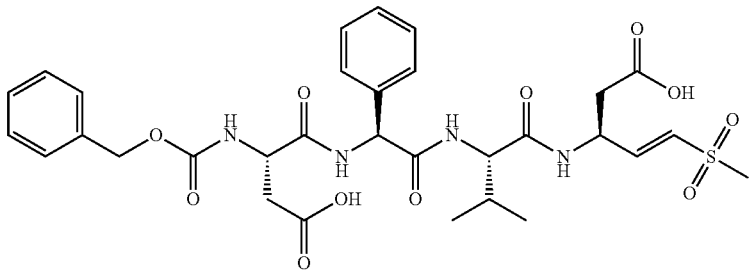 [SMILES: CC(C)[C@H](NC(=O)[C@@H](NC(=O)[C@H](CC(=O)O)NC(=O)OCc1ccccc1)c1ccccc1)C(=O)N[C@H](/C=C/S(C)(=O)=O)CC(=O)O]

Z-Asp(β-tert-Butyl)-Phg-Val-Asp(β-tert-butyl)-methyl vinyl sulfone (6.2 mg) was dissolved in dichloromethane (0.16 ml), followed by addition of trifluoroacetic acid (0.22 ml). The mixture was stirred at room temperature overnight (15 h). It was then quenched with diethyl ether (5 ml), then the solvent was removed under vacuum. The obtained residue was diluted again with ether (5 ml) and the process was repeated twice. The crude material was diluted once more with ether, the filtrate was removed and the precipitate was washed with 2*1 ml of ether, dried to give 5 mg of the desired compound.

NMR $^1$H (CD$_3$OD, 400 MHz) δ: 7.46-7.29 (m, 10H); 6.83 (dd, 1H, J=15.22 Hz, J=4.60 Hz); 6.68 (dd, 1H, J=15.229 Hz, J=1.36 Hz); 5.38 (s, 1H); 5.10 (q, 2H, J=12.73 Hz); 4.94-4.90 (m, 1H); 4.56 (t, 1H, J=6.75 Hz); 4.10 (d, 1H, J=7.07 Hz); 2.95 (s, 3H); 2.98-2.88 (m, 1H); 2.76-2.60 (m, 3H); 2.21-2.01 (m, 1H); 0.98 (t, 6H, J=6.3 Hz).

LCMS (M-H$^+$)=673.7

Example 26

Synthesis of compound 54 (Z-Asp(β-tert-Butyl)-Al (2'-quinolyl)-Val-Asp(β-tert-Butyl)methyl vinyl sulfone)

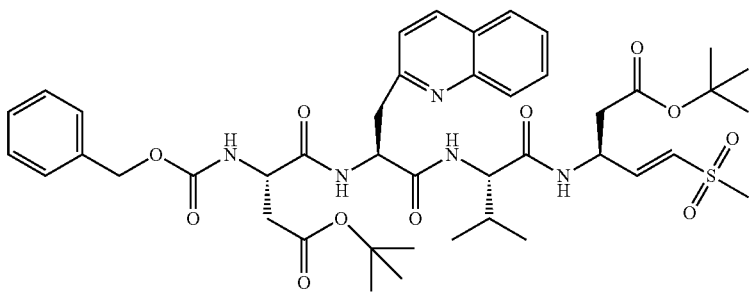 [SMILES: CC(C)[C@H](NC(=O)[C@H](Cc1ccc2ccccc2n1)NC(=O)[C@H](CC(=O)OC(C)(C)C)NC(=O)OCc1ccccc1)C(=O)N[C@H](/C=C/S(C)(=O)=O)CC(=O)OC(C)(C)C]

The Z-Asp(β-tert-Butyl)-Al(2'-quinolyl)-Val-OH (19 mg, 0.0306 mmol) is dissolved in a mix of dichloromethane and DMF (0.4 ml/0.14 ml). The mixture was allowed to reach −15/−20° C. before adding N-methyl morpholine (9 μl) followed 3 min latter with isobutyl chloroformate (9 μl). The mixture was stirred at −15° C. for 10 minutes. Next, Asp (β-tert-butyl)methyl vinyl sulfone tosyl salt (13.1 mg, 1 eq) was added in one shot, followed by N-methyl morpholine (9 μl). The mixture was stirred 35 minutes at −15/−20° C. and then diluted with 5 ml of dichloromethane and quenched with 1.5 ml of a saturated solution of sodium bicarbonate. After that, the organic layer was washed with sodium bicarbonate and dried over magnesium sulphate. The solvent was evaporated to dryness. The obtained residue was purified on silica gel (gradient: ethyl acetate/hexane: 5 to 100%) to afford 13.1 mg of Z-Asp(β-tert-Butyl)-Al(2'-quinolyl)-Val-Asp(β-tert-butyl)-methyl vinyl sulfone.

Example 27

Synthesis of compound 55
(Z-Asp-Ala(2'-quinolyl)-Val-Aspmethyl vinyl sulfone)

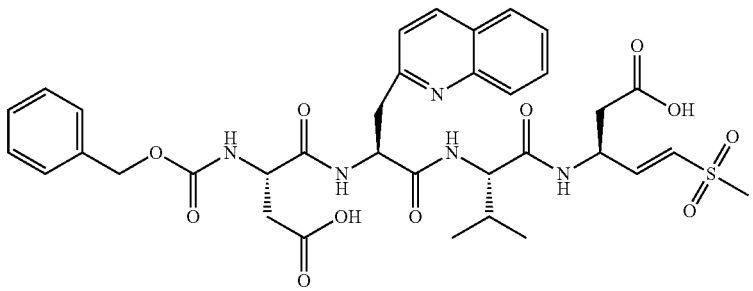 [SMILES: CC(C)[C@H](NC(=O)[C@H](Cc1ccc2ccccc2n1)NC(=O)[C@H](CC(=O)O)NC(=O)OCc1ccccc1)C(=O)N[C@H](/C=C/S(C)(=O)=O)CC(=O)O]

Z-Asp(β-tert-Butyl)-Phg-Val-Asp(β-tert-butyl)-methyl vinyl sulfone (13.1 mg) was dissolved in dichloromethane (0.32 ml), followed by addition of trifluoroacetic acid (0.44 ml). The mixture was stirred at room temperature overnight (15 h). It was then quenched with diethyl ether (5 ml), then the solvent was removed under vacuum. The obtained residue was diluted again with ether and the process was repeated twice. The precipitate was washed with 2*1 ml of ether, dried to give 12 mg of the desired compound.

NMR $^1$H (CD$_3$OD, 400 MHz) δ: 8.68 (m, 1H); 8.17 (d, 1H, J=8.9 Hz); 8.1 (d, 1H, J=8.2 Hz); 7.93 (t, 1H, J=7.85 Hz); 7.78 (m, 2H); 7.34-7.29 (m, 5H); 6.88 (dd, 1H, J=15.20 and 4.75 Hz); 6.7 (d, 1H, J=15.20 Hz); 5.03-4.83 (m, 4H); 4.44 (t, 1H, J=6.45 Hz); 4.1 (d, 1H, J=7.15 Hz); 3.70 (m, 1H); 3.52 (m, 1H); 2.98 (s, 3H); 2.90-2.68 (m, 4H); 0.92 (d, 3H, J=6.9 Hz), 0.89 (d, 3H, J=6.7 Hz).

LCMS (M-H$^+$)=738.3

Example 28

Synthesis of compound 56 (Z-Asp(β-tert-Butyl)-Indanylglycine-Val-Asp(β-tert-Butyl)methyl vinyl sulfone)

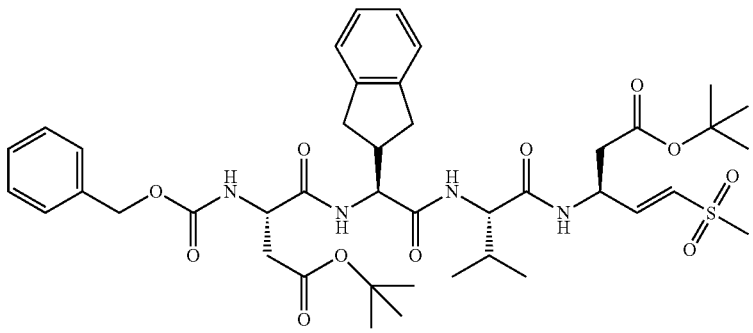 [SMILES: CC(C)[C@H](NC(=O)[C@@H](NC(=O)[C@H](CC(=O)OC(C)(C)C)NC(=O)OCc1ccccc1)C1Cc2ccccc2C1)C(=O)N[C@H](/C=C/S(C)(=O)=O)CC(=O)OC(C)(C)C]

The Z-Asp(β-tert-Butyl)-Indanylglycine-Val-OH (21 mg, 0.0353 mmol) is dissolved in a mix of dichloromethane and DMF (0.44 ml/0.15 ml). The mixture was allowed to reach −15/−20° C. before adding N-methyl morpholine (10 μl) followed by isobutyl chloroformate (9 μl). The mixture was stirred at −15° C. for 10 minutes. Next, Asp (β-tert-butyl) methyl vinyl sulfone tosyl salt (15 mg, 1 eq) was added in one shot, followed by N-methyl morpholine (10 μl). The mixture was stirred 35 minutes at −15/−20° C. and then diluted with 5 ml of dichloromethane and quenched with 1.5 ml of a saturated solution of sodium bicarbonate. After that, the organic layer was washed with sodium bicarbonate and dried over magnesium sulphate. The solvent was evaporated to dryness. The obtained residue was purified on silica gel (ethyl acetate/hexane: 40% then dichloromethane/methanol: 5 to 15%) to afford 10 mg of Z-Asp(β-tert-Butyl)-indanylglycine-Val-Asp(β-tert-butyl)-methyl vinyl sulfone.

Example 30

Synthesis of compound 57
(Z-Asp-Indanylglycine-Val-Aspmethyl vinyl sulfone)

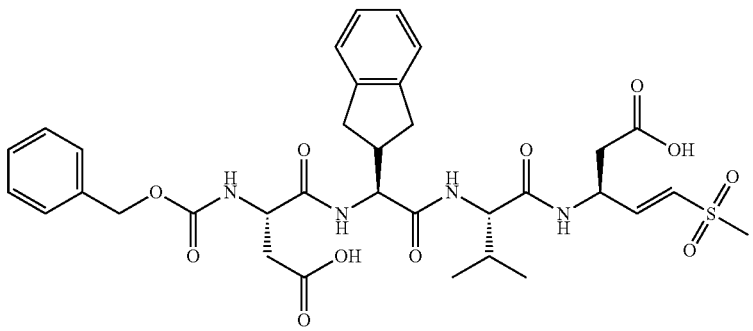 [SMILES: CC(C)[C@H](NC(=O)[C@@H](NC(=O)[C@H](CC(=O)O)NC(=O)OCc1ccccc1)C1Cc2ccccc2C1)C(=O)N[C@H](/C=C/S(C)(=O)=O)CC(=O)O]

Z-Asp(β-tert-Butyl)-Indanylglycine-Val-Asp(β-tert-butyl)-methyl vinyl sulfone (11 mg) was dissolved in dichloromethane (0.26 ml), followed by addition of trifluoroacetic acid (0.36 ml). The mixture was stirred at room temperature overnight (15 h). It was then quenched with diethyl ether (5 ml) and the solvent was removed under vacuum. The obtained residue was diluted again with ether and the process was repeated twice. The precipitate was washed with 2*1 ml of ether, dried to give 9 mg of the desired compound.

NMR $^1$H (DMSO, 400 MHz) δ: 12.35 (bs, 2H, 2*CO$_2$H); 8.21 (d, 1H, J=7.78 Hz); 8.06 (m, 1H); 7.89 (d, 1H, J=7.34 Hz); 7.61 (d, 1H, J=7.10 Hz); 7.34-7.31 (m, 5H); 7.17-6.95 (m, 4H); 6.75 (dd, 1H, J=15.33 Hz, J=4.8 Hz); 6.64 (d, 1H, J=15.58 Hz); 4.99 (s, 2H); 4.81 (m, 1H); 4.46-4.40 (m, 2H); 4.12 (t, 1H, J=6.28 Hz); 2.97 (s, 3H); 2.82-2.44 (m, 9H); 0.85 (t, 6H, J=5.95 Hz).

Example 32

Synthesis of compound 58 (Z-Asp(β-tert-Butyl)-Glu(β-tert-Butyl)-Val-Asp(β-tert-Butyl)methyl vinyl sulfone)

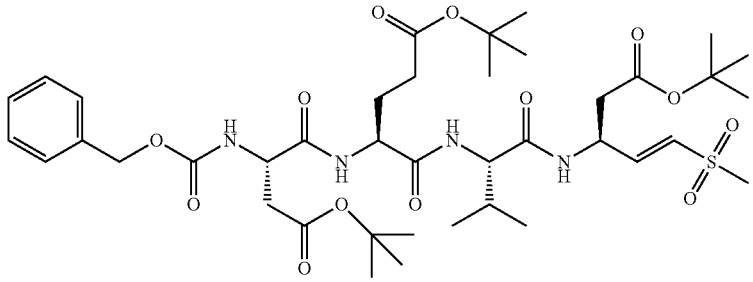 [SMILES: CC(C)[C@H](NC(=O)[C@H](CCC(=O)OC(C)(C)C)NC(=O)[C@H](CC(=O)OC(C)(C)C)NC(=O)OCc1ccccc1)C(=O)N[C@H](/C=C/S(C)(=O)=O)CC(=O)OC(C)(C)C]

The Z-Asp(β-tert-Butyl)-Glu(β-tert-Butyl)-Val-OH (18 mg, 0.029 mmol) is dissolved in a mix of dichloromethane and DMF (0.39 ml/0.13 ml). The mixture was allowed to reach −15/−20° C. before adding N-methyl morpholine (8 μl) followed 3 min latter with isobutyl chloroformate (7 μl). The mixture was stirred at −15° C. for 10 minutes. Next, Asp (β-tert-butyl)methyl vinyl sulfone tosyl salt (13 mg) was added in one shot, followed by N-methyl morpholine (8 μl). The mixture was stirred 35 minutes at −15/−20° C. and then diluted with 5 ml of dichloromethane and quenched with 1.5 ml of a saturated solution of sodium bicarbonate. After that, the organic layer was dried over magnesium sulphate. The solvent was evaporated to dryness. The obtained residue was purified on silica gel (ethyl acetate/hexane: 40% then dichloromethane/methanol: 5 to 15%) to afford 24 mg of the desired compound.

Example 33

Synthesis of compound 59
(Z-Asp-Glu-Val-Aspmethyl vinyl sulfone)

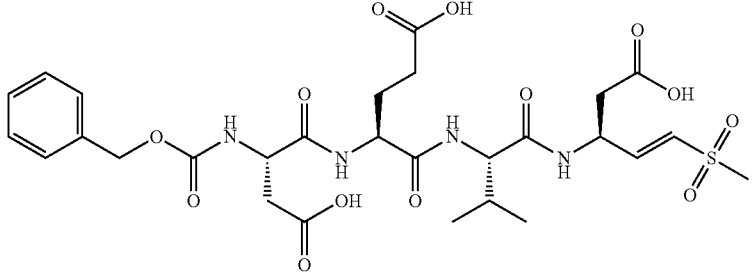 [SMILES: CC(C)[C@H](NC(=O)[C@H](CCC(=O)O)NC(=O)[C@H](CC(=O)O)NC(=O)OCc1ccccc1)C(=O)N[C@H](/C=C/S(C)(=O)=O)CC(=O)O]

Z-Asp(β-tert-Butyl)-Glu(β-tert-Butyl)-Val-Asp(β-tert-butyl)-methyl vinyl sulfone (22.7 mg) was dissolved in dichloromethane (0.55 ml), followed by addition of trifluoroacetic acid (0.7 ml). The mixture was stirred at room temperature overnight (15 h). It was then quenched with diethyl ether (7 ml) and the solvent was removed under vacuum. The obtained residue was diluted again with ether (5 ml) and the process was repeated twice. The precipitate was washed with 2*1 ml of ether, dried to give 19 mg of the desired compound.

Example 34

Synthesis of compound 60
Z-Val-Asp(β-tert-Butyl)methyl vinyl sulfone

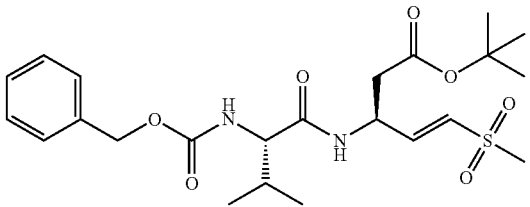 [SMILES: CC(C)[C@H](NC(=O)OCc1ccccc1)C(=O)N[C@H](/C=C/S(C)(=O)=O)CC(=O)OC(C)(C)C]

The Z-Val-OH (15 mg, 0.059 mmol) is dissolved in a mix of dichloromethane and DMF (0.5 ml/0.2 ml). The mixture was allowed to reach −15/−20° C. before adding N-methyl morpholine (10 μl) followed by isobutyl chloroformate (9 μl). The mixture was stirred at −15° C. for 10 minutes. Next, Asp (β-tert-butyl)methyl vinyl sulfone tosyl salt (25 mg, 1 eq) was added in one shot, followed by N-methyl morpholine (10 μl). The mixture was stirred 35 minutes at −15/−20° C. and then diluted with 5 ml of dichloromethane and quenched with 1.5 ml of a saturated solution of sodium bicarbonate. After that, the organic layer was dried over magnesium sulphate. The solvent was evaporated to dryness. The obtained residue was purified on silica gel (gradient: methanol/dichloromethane: 0 to 15%) to afford 24 mg of Z-Val-Asp-methyl vinyl sulfone.

NMR $^1$H (CD$_3$OD, 400 MHz) δ: 7.38-7.29 (m, 5H); 6.82 (m, 1H); 6.69 (m, 1H); 5.10 (m, 2H); 4.96 (m, 1H); 3.91 (m, 1H); 2.94 (s, 3H); 2.8-2.6 (m, 2H); 2.1-2.0 (m, 1H); 1.43 (s, 9H); 0.95 (t, 6H, J=6.7 Hz).

Example 35

Synthesis of compound 61 (Z-Val-Asp-methyl vinyl sulfone)

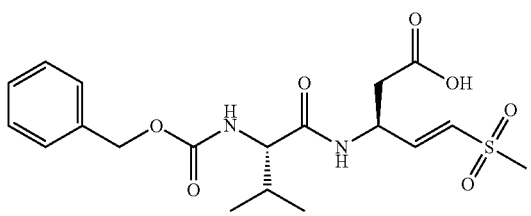 [SMILES: CC(C)[C@H](NC(=O)OCc1ccccc1)C(=O)N[C@H](/C=C/S(C)(=O)=O)CC(=O)O]

Z-Val-Asp(β-tert-butyl)-methyl vinyl sulfone (25 mg) was dissolved in dichloromethane (0.6 ml), followed by addition of trifluoroacetic acid (0.45 ml). The mixture was stirred at room temperature overnight (15 h). It was then quenched with diethyl ether (7 ml), the solvent was removed under vacuum. The obtained residue was diluted again with ether and the process was repeated twice. The precipitate was washed with 2*1 ml of ether, dried to give 22 mg of the desired compound.

NMR $^1$H (CD$_3$OD, 400 MHz) δ: 7.38-7.27 (m, 5H); 6.86 (m, 1H); 6.68 (m, 1H); 5.11 (m, 2H); 5.03 (m, 1H); 3.92 (m, 1H); 2.94 (s, 3H); 2.88-2.59 (m, 2H); 2.09-2.01 (m, 1H); 0.95 (t, 6H, J=6.49 Hz).

Example 36

Synthesis of compound 62 (Z-Asp(β-tert-Butyl)-Ala(2'-quinolyl)-Val-Asp(β-tert-Butyl)phenyl vinyl sulfone)

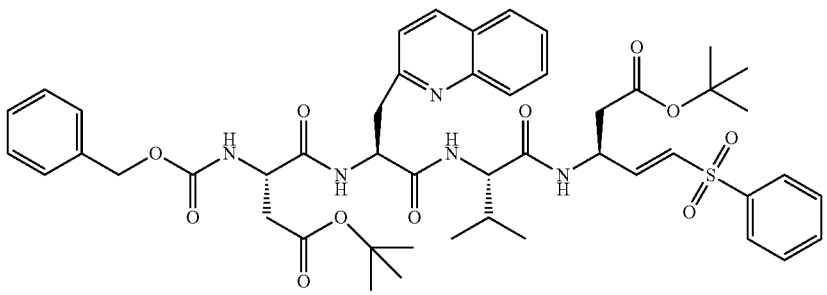 [SMILES: CC(C)[C@H](NC(=O)[C@H](Cc1ccc2ccccc2n1)NC(=O)[C@H](CC(=O)OC(C)(C)C)NC(=O)OCc1ccccc1)C(=O)N[C@H](/C=C/S(=O)(=O)c1ccccc1)CC(=O)OC(C)(C)C]

The Z-Asp(β-tert-Butyl)-Ala(2'-quinolyl)-Val-OH (19 mg, 0.0306 mmol) is dissolved in a mix of dichloromethane and DMF (0.39 ml/0.13 ml). The mixture was allowed to reach −15/−20° C. before adding N-methyl morpholine (8 μl) followed by isobutyl chloroformate (7 μl). The mixture was stirred at −15° C. for 10 minutes. Next, Asp (β-tert-butyl)phenyl vinyl sulfone tosyl salt (11 mg) was added in one shot, followed by N-methyl morpholine (8 nl). The mixture was stirred 35 minutes at −15/−20° C. and then diluted with 5 ml of dichloromethane and quenched with 1.5 ml of a saturated solution of sodium bicarbonate. After that, the organic layer was dried over magnesium sulphate. The solvent was evaporated to dryness. The obtained residue was purified on silica gel (gradient: ethyl acetate/hexane: 5 to 100%) to afford 13.7 mg of the desired compound.

Example 37

Synthesis of compound 63 (Z-Asp-Ala(2'-quinolyl)-Val-Aspphenyl vinyl sulfone)

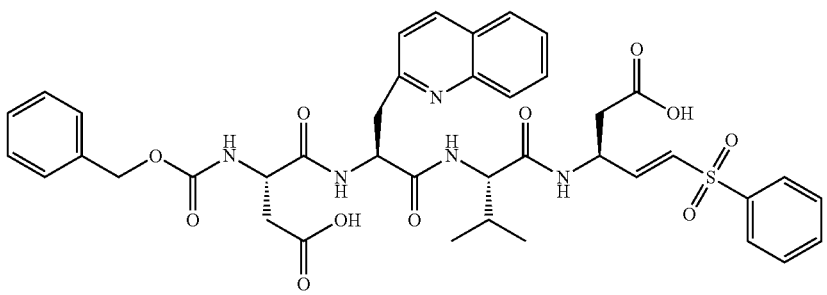 [SMILES: CC(C)[C@H](NC(=O)[C@H](Cc1ccc2ccccc2n1)NC(=O)[C@H](CC(=O)O)NC(=O)OCc1ccccc1)C(=O)N[C@H](/C=C/S(=O)(=O)c1ccccc1)CC(=O)O]

Z-Asp(β-tert-Butyl)-Ala(2'-quinolyl)-Val-Asp(β-tert-Butyl)-phenyl vinyl sulfone (13.7 mg) was dissolved in dichloromethane (0.3 ml), followed by addition of trifluoroacetic acid (0.4 ml). The mixture was stirred at room temperature overnight (15 h). It was then quenched with diethyl ether (5 ml), the solvent was removed under vacuum. The obtained residue was diluted again with ether and the process was repeated twice. The precipitate was washed with 2*1 ml of ether, dried to give 10 mg of the desired compound.

NMR $^1$H (CD$_3$OD, 400 MHz) δ: 8.58 (m, 1H); 8.11 (d, 1H, J=8.75 Hz); 8.04 (d, 1H, J=7.99 Hz); 7.85 (d, 3H, J=7.25 Hz); 7.72-7.6 (m, 3H); 7.56 (t, 2H, J=7.83 Hz); 7.31-7.28 (m, 5H); 6.93 (dd, 1H, J=15.24 Hz, J=5.15 Hz); 6.65 (d, 1H, J=14.87 Hz); 4.97-4.80 (m, 4H); 4.40 (m, 1H); 4.21-4.02 (m, 1H); 3.63-3.50 (m, 1H); 3.47-3.44 (m, 1H); 2.82-2.6 (m, 4H); 2.15-1.98 (m, 1H); 0.81 (t, 6H, J=6.38 Hz).

LCMS (M-H+)=800.5

Example 38

Synthesis of compound 64 (Z-Asp(β-tert-Butyl)-Ala(2'-quinolyl)-Val-Asp(β-tert-Butyl)phenoxy vinyl sulfone)

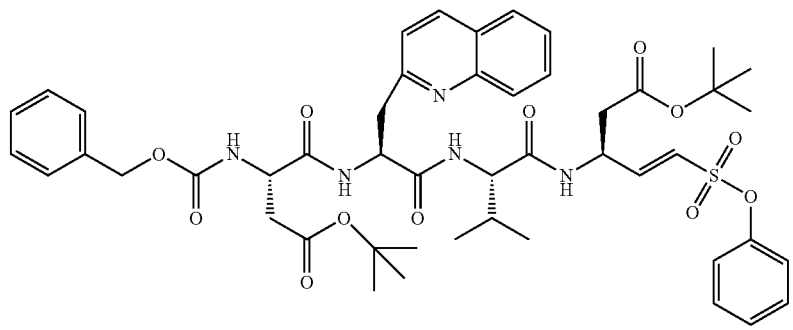 [SMILES: CC(C)[C@H](NC(=O)[C@H](Cc1ccc2ccccc2n1)NC(=O)[C@H](CC(=O)OC(C)(C)C)NC(=O)OCc1ccccc1)C(=O)N[C@H](/C=C/S(=O)(=O)Oc1ccccc1)CC(=O)OC(C)(C)C]

The Z-Asp(β-tert-Butyl)-Al(2'-quinolyl)-Val-OH (10 mg, 0.016 mmol) is dissolved in a mix of dichloromethane and DMF (0.24 ml/0.080 ml). The mixture was allowed to reach −15/−20° C. before adding N-methyl morpholine (5 n1) followed 3 min latter with isobutyl chloroformate (5 μl). The mixture was stirred at −15° C. for 10 minutes. Next, Asp (β-tert-butyl)phenoxy vinyl sulfone tosyl salt (11.3 mg, 0.023 mmol) was added in one shot, the vial was washed with DMF (0.04 ml), followed by the addition of N-methyl morpholine (5 μl). The mixture was stirred 35 minutes at −15/−20° C. and then diluted with 5 ml of dichloromethane and quenched with 1.5 ml of a saturated solution of sodium bicarbonate. After that, the organic layer was dried over magnesium sulphate. The solvent was evaporated to dryness. The obtained residue was purified on silica gel (gradient: ethyl acetate/hexane: 12 to 100%) to afford 4.7 mg of the desired compound.

Example 39

Synthesis if compound 65 (Z-Asp-Ala(2'-quinolyl)-Val-Aspphenoxy vinyl sulfone)

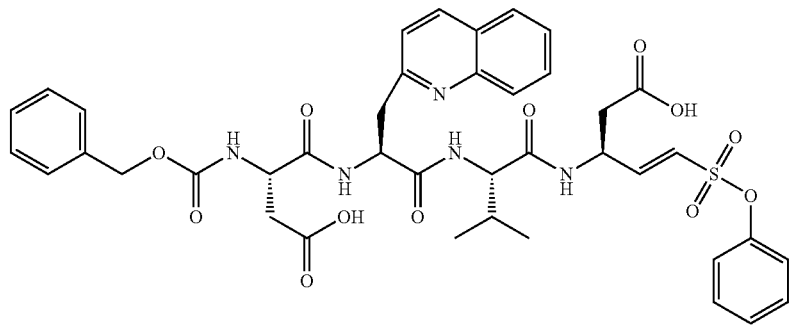 [SMILES: CC(C)[C@H](NC(=O)[C@H](Cc1ccc2ccccc2n1)NC(=O)[C@H](CC(=O)O)NC(=O)OCc1ccccc1)C(=O)N[C@H](/C=C/S(=O)(=O)Oc1ccccc1)CC(=O)O]

Z-Asp(β-tert-Butyl)-Ala(2'-quinolyl)-Val-Asp(β-tert-Butyl)-phenoxy vinyl sulfone (4.7 mg) was dissolved in dichloromethane (0.15 ml), followed by addition of trifluoroacetic acid (0.2 ml). The mixture was stirred at room temperature overnight (15 h). It was then quenched with diethyl ether (5 ml) and the solvent was removed under vacuum. The obtained residue was diluted again with ether (5 ml) and the process was repeated twice. The precipitate was washed with 2*1 ml of ether, dried to give 4 mg of the desired compound.

NMR $^1$H (CD$_3$OD, 400 MHz) δ: 8.25 (d, 1H, J=7.9 Hz); 8.05 (d, 1H, J=8.66 Hz); 7.88 (d, 1H, J=8.25 Hz); 7.63 (d, 1H, J=6.82 Hz); 7.53 (t, 1H, J=7.46 Hz); 7.45-7.33 (m, 3H); 7.33-7.20 (m, 8H); 6.75 (dd, 1H, J=15.33 Hz, J=4.33 Hz); 6.65 (d, 1H, J=15.55 Hz); 5.1-4.8 (m, 4H); 4.49 (t, 1H, J=6.17 Hz); 4.06 (d, 1H, J=6.45 Hz); 3.6-3.4 (m, 2H); 2.9 (dd, 1H, J=17.02 Hz, J=5.39 Hz); 2.73 (dd, 1H, J=16.57 Hz, J=6.53 Hz); 2.59 (d, 2H, J=6.97 Hz); 2.08 (m, 1H); 0.75 (m, 6H).

Example 40

Synthesis of compound 66 (Z-Asp(β-tert-Butyl)-Ala(2'-quinolyl)-Val-Asp(β-tert-Butyl)morpholine vinyl sulfone)

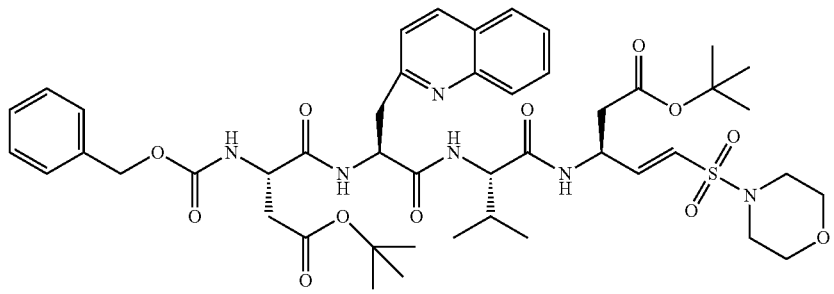 [SMILES: CC(C)[C@H](NC(=O)[C@H](Cc1ccc2ccccc2n1)NC(=O)[C@H](CC(=O)OC(C)(C)C)NC(=O)OCc1ccccc1)C(=O)N[C@H](/C=C/S(=O)(=O)N1CCOCC1)CC(=O)OC(C)(C)C]

Z-Asp(β-tert-Butyl)-Ala(2'-quinolyl)-Val-OH (13 mg, 0.0209 mmol) is dissolved in a mix of dichloromethane and DMF (0.28/0.094 ml). The mixture was allowed to reach −15/−20° C. before adding N-methyl morpholine (6 μl) followed by isobutyl chloroformate (5 μl). The mixture was stirred at −15° C. for 10 minutes. Next, Asp (β-tert-butyl) morpholine vinyl sulfone tosyl salt (10.2 mg, 1 eq) was added in one shot, followed by N-methyl morpholine (6 μl). The mixture was stirred 35 minutes at −15/−20° C. and then diluted with 5 ml of dichloromethane and quenched with 1.5 ml of a saturated solution of sodium bicarbonate. After that, the organic layer was washed with sodium bicarbonate and dried over magnesium sulphate. The solvent was evaporated to dryness. The obtained residue was purified on silica gel (gradient: ethyl acetate/hexane: 12 to 100%) to afford 10 mg of the desired compound.

Example 41

Synthesis of compound 67 (Z-Asp-Ala(2'-quinolyl)-Val-Aspmorpholine vinyl sulfone)

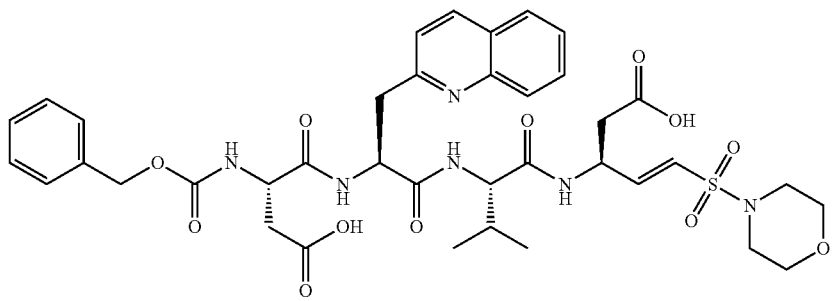 [SMILES: CC(C)[C@H](NC(=O)[C@H](Cc1ccc2ccccc2n1)NC(=O)[C@H](CC(=O)O)NC(=O)OCc1ccccc1)C(=O)N[C@H](/C=C/S(=O)(=O)N1CCOCC1)CC(=O)O]

Z-Asp(β-tert-Butyl)-Al(2'-quinolyl)-Val-Asp(β-tert-Butyl)-morpholine vinyl sulfone (4.7 mg) was dissolved in dichloromethane (0.15 ml), followed by addition of trifluoroacetic acid (0.2 ml). The mixture was stirred at room temperature overnight (15 h). It was then quenched with diethyl ether (5 ml) and the solvent was removed under vacuum. The obtained residue was diluted again with ether and the process was repeated twice. The precipitate was washed with 2*1 ml of ether, dried to give 4 mg of the desired compound.

NMR $^1$H (CD$_3$OD, 400 MHz) δ: 8.39 (s, 1H); 8.08 (d, 1H, J=8.56 Hz); 7.94 (d, 1H, J=8.29 Hz); 7.74 (m, 1H); 7.66-7.55 (m, 2H); 7.31-7.29 (m, 5H); 6.69 (dd, 1H, J=14.98 Hz, J=4.59 Hz); 6.41 (d, 1H, J=14.86 Hz); 5.0-4.7 (m, 4H); 4.45 (m, 1H); 4.05 (d, 1H, J=6.65 Hz); 3.70-3.64 (m, 4H); 3.55-3.44 (m, 2H); 3.16-3.08 (m, 4H); 2.89-2.70 (m, 4H); 2.17-2.07 (m, 1H); 0.85-0.81 (m, 6H).

LCMS (M-H+)=809.6

Example 42

Synthesis of compound 68
(Z-Asp-Indanylglycine-Val-Aspisopropyl vinyl sulfone)

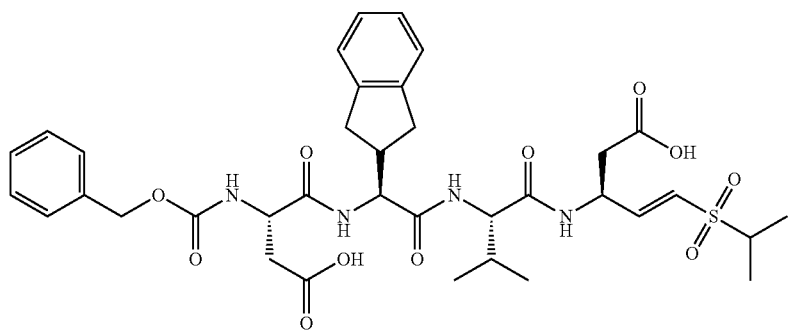 [SMILES: CC(C)[C@H](NC(=O)[C@@H](NC(=O)[C@H](CC(=O)O)NC(=O)OCc1ccccc1)C1Cc2ccccc2C1)C(=O)N[C@H](/C=C/S(=O)(=O)C(C)C)CC(=O)O]

This compound was synthesized from Asp(β-tert-butyl) isopropyl vinyl sulfone tosyl salt (43) and Cbz-Asp(O-tBu) Indanylglycine-Val-OH (12) via anhydride mixture method as for Z-Asp-Indanylglycine-Val-Aspmethyl vinyl sulfone (57).

Example 43

Synthesis of compound 69
(Z-Asp-Phg-Val-Asp-phenyl vinylsulfone)

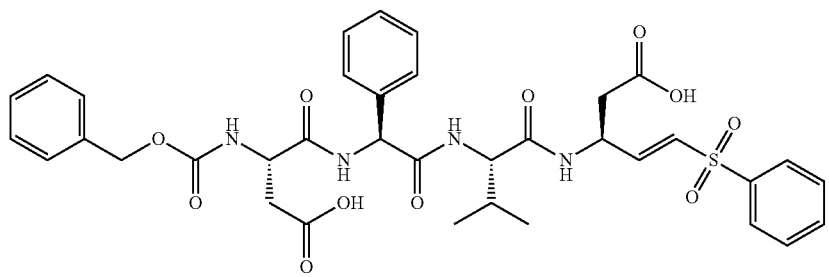 [SMILES: CC(C)[C@H](NC(=O)[C@@H](NC(=O)[C@H](CC(=O)O)NC(=O)OCc1ccccc1)c1ccccc1)C(=O)N[C@H](/C=C/S(=O)(=O)c1ccccc1)CC(=O)O]

This compound was synthesized from Z-Asp(β-tert-Butyl)-Phg-Val-OH (16) and Asp(OtBu)-Vinyl phenyl sulfone tosyl salt (37) via anhydride mixture method as for Z-Asp-Ala(2'-quinolyl)-Val-Aspphenyl vinyl sulfone (63).

Example 44

Synthesis of compound 70 (Z-Asp-(D, L Ala(2'-quinolyl))-Val-Aspphenyl vinylsulfone)

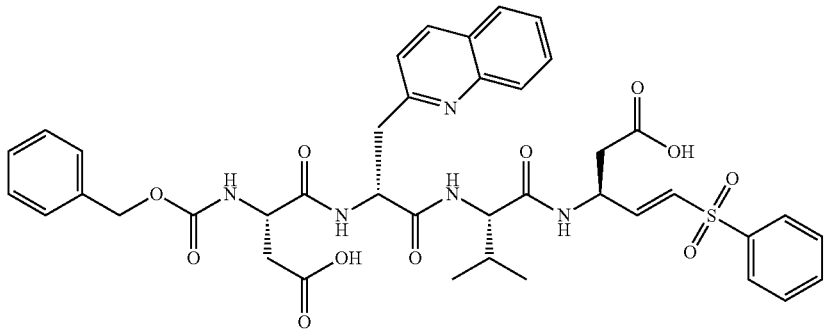 [SMILES: CC(C)[C@H](NC(=O)[C@@H](Cc1ccc2ccccc2n1)NC(=O)[C@H](CC(=O)O)NC(=O)OCc1ccccc1)C(=O)N[C@H](/C=C/S(=O)(=O)c1ccccc1)CC(=O)O]

This compound was synthesized as the corresponding Z-Asp-Ala(2'-quinolyl)-Val-Aspphenyl vinyl sulfone (63).

Example 45

Synthesis of compound 71 (Z-Asp-(D, L Ala(2'-quinolyl))-Val-Aspmethyl vinylsulfone)

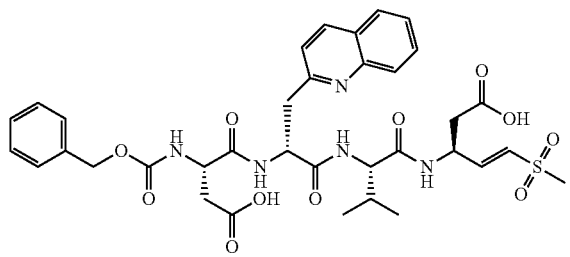 [SMILES: CC(C)[C@H](NC(=O)[C@@H](Cc1ccc2ccccc2n1)NC(=O)[C@H](CC(=O)O)NC(=O)OCc1ccccc1)C(=O)N[C@H](/C=C/S(C)(=O)=O)CC(=O)O]

This compound was synthesized as the corresponding Z-Asp-Ala(2'-quinolyl)-Val-Aspmethyl vinyl sulfone (55).

Example 46

Synthesis of compound 76 (Z-Asp-Tyr-Val-Aspmethyl vinyl sulfone)

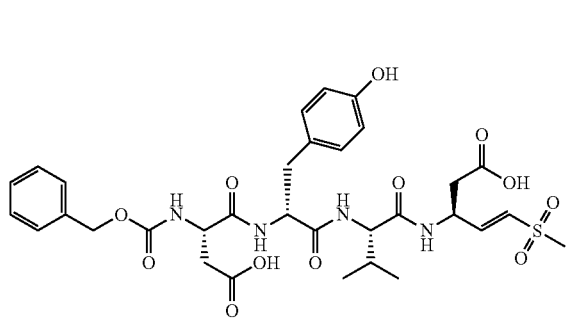 [SMILES: CC(C)[C@H](NC(=O)[C@@H](Cc1ccc(O)cc1)NC(=O)[C@H](CC(=O)O)NC(=O)OCc1ccccc1)C(=O)N[C@H](/C=C/S(C)(=O)=O)CC(=O)O]

This compound was synthesized from Z-Asp-Tyr(OtBu)-Val-OH (75) and Asp(OtBu)-Vinyl methy sulfone tosyl salt (33) via anhydride mixture method as for Z-Asp-Phg-Val-Aspmethyl vinyl sulfone (53).

Z-Asp-Tyr(OtBu)-Val-OH was synthesized as Cbz-Asp (O-tBu)-Glu(O-tBu)-Val-OH (20).

Example 47

Synthesis of compound 82 (Z-Tyr-Glu-Val-Aspmethyl vinyl sulfone)

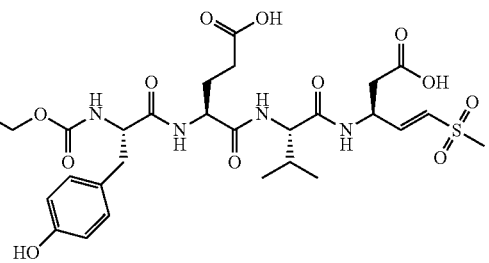

This compound was synthesized from Z-Tyr(OtBu)-Glu(OtBu)-Val-OH (80) and Asp(OtBu)-Vinyl methy sulfone tosyl salt (33) via anhydride mixture method as for Z-Asp-Phg-Val-Aspmethyl vinyl sulfone (53).

Z-Tyr(OtBu)-Glu(OtBu)-Val-OH (80) was synthesized as Cbz-Asp(O-tBu)-Glu(O-tBu)-Val-OH (20).

Example 48

Synthesis of compound 88 (Z-Asp-Trp-Val-Aspmethyl vinyl sulfone)

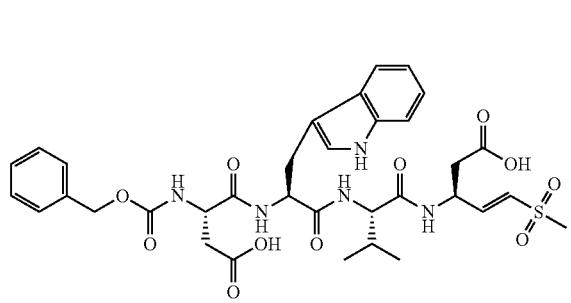 [SMILES: CC(C)[C@H](NC(=O)[C@H](Cc1c[nH]c2ccccc12)NC(=O)[C@H](CC(=O)O)NC(=O)OCc1ccccc1)C(=O)N[C@H](/C=C/S(C)(=O)=O)CC(=O)O]

This compound was synthesized from Z-Asp(OtBu)-Trp-Val-OH (86) and Asp(OtBu)-Vinyl methy sulfone tosyl salt (33) via anhydride mixture method as for Z-Asp-Phg-Val-Aspmethyl vinyl sulfone (53).

Example 49

Synthesis of compound 85
(Z-Asp-Ala(2'-pyridyl)-Val-Aspmethyl vinylsulfone)

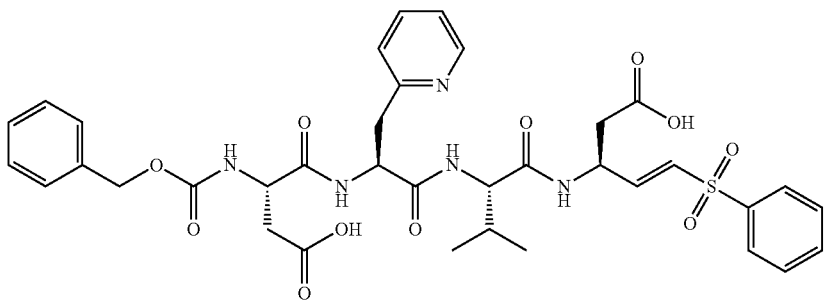 [SMILES: CC(C)[C@H](NC(=O)[C@H](Cc1ccccn1)NC(=O)[C@H](CC(=O)O)NC(=O)OCc1ccccc1)C(=O)N[C@H](/C=C/S(=O)(=O)c1ccccc1)CC(=O)O]

This compound was synthesized from Z-Asp(OtBu)-Ala(2'-pyridyl)-Val-OH (83) and Asp(OtBu)-Vinyl phenyl sulfone tosyl salt (37) via anhydride mixture method as for Z-Asp-Ala(2'-quinolyl)-Val-Aspphenyl vinyl sulfone (63).

Example 50

Selectivity of exemplary compounds for caspase-3 relative to caspase-1, caspase-5, caspase-7, and caspase-9

Selectivity of compound 55, compound 63, compound 48, compound 57, compound 88 toward caspase-1 (pro-inflammatory group), caspase-5 (group I), caspase-9 (group II) and caspase-3 and caspase-7 (group III) was evaluated by using fluorometric methods using the Caspase-1, -3, -5, -7, -9 Inhibitor Drug Screening Kit™ (Catalog #: K151-100, K153-100, K155-100, K157-100, K159-100 respectively, BioVision™). Briefly, using instructions of the manufacturer, a wide range of different concentrations of the compound: 3333, 1000, 333, 100, 33, 10, 3, and 1 nM (final concentration) was added directly to the reaction mixtures containing the substrate and the enzyme in a final volume of 10 μl. After a 30-minute incubation at 37° C., the liberation of AFC was measured as an endpoint assay using the Flexstation3™ (Molecular Devices) with an excitation wavelength of 400 nm and an emission wavelength of 505 nm. The level of inhibition of caspase-1, -3, -5, -7, -9 activity was determined by comparison of the relative fluorescence intensity in samples with or without the compound. Results are summarized in Table 2 herein after.

As shown in Table 2, Compound 55 showed an inhibitory effect on both caspase-3 and -7 activity. However, based on the IC50 values calculated, it was about 200 fold more selective of Caspase-3 over Caspase-7 (see Table 2). No significant inhibitory activity of the compound was observed for caspase-1, -5, and -9 at the tested dose-range. Inhibition of Caspase-1, -5, and -9 was achieved (25%, 21%, and 57% respectively) but at extremely high concentration (about 10,000 nM).

Similar to Compound 55, Compound 63 also showed high selectivity in caspase-3 activity inhibition relative to caspase-1, -5, -7, and -9. Compound 63 also showed an inhibitory effect on caspase-3 and -7, with about a 50 fold selectivity of caspase-3 over caspase-7. No significant inhibitory activity was observed for caspase-1, -5, and -9 at the tested dose-range of Compound 63. The data indicates that both Compound 55 and Compound 63 are highly potent and selective compounds for caspase-3 activity inhibition.

Compound 48 was able to inhibit specific groups of caspases. The compound was able to inhibit caspase-3, -7, and -9 with IC50 values of about 8-30 nM, 0.4-0.9 uM and 1-1.8 uM respectively. Thus Compound 48 shows inhibition of Group III caspases (caspase-3 and -7) with high potency, and inhibition of Group II caspase (caspase-9) with a lower yet significant efficacy.

From the inhibition profile of Compound 57 on caspase-1, -3, -5, -7, and -9 activity, it can be appreciated that Compound 57 is a potent inhibitor of Group III caspases (caspase-3 and -7). Compound 57 inhibited caspase-3 and -7 activities with IC50 values of about 30-90 nM and about 180-300 nM respectively. Therefore, data indicates that Compound 48 and Compound 57 are not specific inhibitors for caspase-3 activity, but are in fact inhibitors targeted at specific groups of caspases.

Compound 88 has a dual inhibition effect on both caspase-1 and caspase-3 activity. It is a potent inhibitor of caspase-3 activity, with an IC50 value of about 30-90 nM. It also inhibits caspase-1 activity with an IC50 value of about 0.6-1.2 uM.

Example 51

In Vitro Inhibitory Activity of Caspase-3 Inhibitors

To test the efficacy of caspase-3 inhibitors at the cellular level, the ability of selected compounds to inhibit the proteolytic cleavage of PARP (poly ADP-ribose polymerase) was evaluated in live Hela cells.

Briefly, in this assay Hela cells are seeded in 96 well plates and incubated for 4 hours with staurosporine, a well characterized inducer of apoptosis, alone or together with different concentrations of compound (50, 25, 10 and 3 uM). After formaldehyde-based fixation, the cells are stained with a fluorescein-labeled anti-cleaved PARP antibody (Cell signaling, Cat#: 9547) and counterstained with Hoechst33342 (Invitrogen, Cat#: H3570) to mark all nuclei. Fluorescence images are taken on a Cellomics™ microscope system (Thermo Scientific, Pittsburgh, USA) with the Hoechst stain in the blue channel and the cleaved PARP antibody stain in the green channel. The percentage of cleaved PARP positive cells is determined by calculating the ratio between nuclei with a cleaved PARP antibody staining above a certain threshold and all (Hoechst positive) nuclei. The efficacy of caspase-3 inhibition is determined by calculating the ratio between cleaved PARP positive cells after staurosporine incubation together with compounds and staurosporine incubation without compounds. Results are summarized in Table 2.

As shown in Table 2, results of this assay show that compounds that inhibited Caspase-3 activity in the enzymatic assay with an IC50 below 100 nM were generally also effective in inhibiting PARP cleavage in vitro, although a major factor contributing to a compound's activity/effectivity in this assay is the compound's cell membrane permeability coefficient (the higher the permeability coefficient, the greater the amount of the compound in the media reaching inside the cell). Certain modifications in the molecular composition of the compounds improved the inhibitory activity further; for example Compound 51, Compound 53, Compound 57, and Compound 76 reduced the percentage of PARP positive cells after staurosporine treatment by more than 50%, with Compound 51 and Compound 57 being the most effective compounds reaching values of about 65% inhibition, and Compound 53 also being highly effective relative to DEVD-fmk (positive control compound with low caspase-3 selectivity but highly cell membrane permeable with general caspase inhibitory activity), and Compounds 48, 55, and 59 also showing effectivity especially relative to DEVD-fmk. These results indicate that inhibitory compounds identified in a primary enzymatic assay screen retain their activity in a cellular environment and that molecular modifications allow to further improve their activity as caspase-3 inhibitors.

TABLE 2

Activity assays for caspase inhibitors. Values given are approximations of the average values obtained from the assays.

| | Compound | Caspase enzymatic activity, IC50 (uM) | | | | | % inhibition of PARP cleavage at 50 uM compound | % inhibition of PARP cleavage at 50 uM DEVDFMK (positive control) | % of inhibition with compound relative to DFVDFMK | IC50 (uM) Glo3/7 |
|---|---|---|---|---|---|---|---|---|---|---|
| No | Name | Caspase 1 | Caspase 3 | Caspase 5 | Caspase 7 | Caspase 9 | | | | |
| 48 | Z-Asp-Ala(2'-quinolyl)-Val-Asp alpha chlorovinyl methylsulfone | >3.33 | 0.01 | >3.33 | 0.4 | 1.2 | 45 | 70 | 65 | 0.1 |
| 50 | Tosyl-Ala(2'-quinolyl)-Val-Asp alpha chlorovinyl methylsulfone | >3.33 | >3.33 | | | | | | | |
| 36 | Boc-Asp(O-tBu)VSphenyl | | >2 | | | | | | | |
| 37 | Asp(O-tBu)VSphenyl salt | | >2 | | | | | | | |
| 16 | Z-Asp(O-tBu)-Phg-Val-OH | | >2 | | | | | | | |
| 51 | Z-Asp(O-Methyl)-Indanylglycine-Val-Asp(O-Methyl)VSmethyl | >3.0 | 1 | >3.0 | >3.0 | >3.0 | 65 | 80 | 80 | |
| 53 | Z-Asp-Phg-Val-AspVSmethyl | 2 | 0.06 | >10 | 0.8 | >10 | 55 | 70 | 80 | 0.1 |
| 93 | AspVSmethyl salt | | >10 | | | | | | | |
| 33 | Asp(O-tBu)VSmethyl salt | | >10 | | | | | | | |
| 71 | Z-Asp-d,l Ala(2'-quinolyl)-Val-AspVSmethyl | >10 | 0.1 | >10 | 8.9 | >10 | | | | |
| 55 | Z-Asp-Ala(2'-quinolyl)-Val-AspVSmethyl | >10 | 0.01 | >10 | 1.4 | >3.33 | 40 | 65 | 60 | 0.1 |
| 65 | Z-Asp-Ala(2'-quinolyl)-Val-AspVSphenoxy | 1.2 | 0.01 | >3.33 | 0.4 | 0.3 | 30 | 75 | 40 | 0.2 |
| 70 | Z-Asp-d,l Ala(2'-quinolyl)-Val-AspVSphenyl | | 0.3 | >10 | >10 | >10 | | | | |
| 63 | Z-Asp-Ala(2'-quinolyl)-Val-AspVSphenyl | >3.33 | 0.04 | >3.33 | 1.8 | >3.33 | 10 | 70 | 15 | 0.9 |
| 66 | Z-Asp-Ala(2'-quinolyl)-Val-AspVSmorpholine | | 0.2 | | | | 25 | | | |
| 85 | Z-Asp-Ala(2'-pyridyl)-Val-AspVSphenyl | >3.33 | 0.03 | >3.33 | 1.0 | >3.33 | 40 | | | |
| 69 | Z-Asp-Phg-Val-AspVSphenyl | 0.1 | | | | | | | | |
| 76 | Z-Asp-Tyr-Val-AspVSmethyl | >3.33 | 0.03 | >3.33 | 0.7 | >3.33 | 55 | 90 | 60 | 0.04 |
| 57 | Z-Asp-Indanylglycine-Val-AspVSmethyl | 0.9 | 0.03 | >3.33 | 0.2 | >3.33 | 65 | 90 | 70 | 0.1 |
| 88 | Z-Asp-Trp-Val-AspVSmethyl | 0.7 | 0.04 | >3.33 | 1.1 | >3.33 | 45 | 90 | 50 | |
| 59 | Z-Asp-Glu-Val-AspVSmethyl | 1.4 | 0.02 | >3.33 | 0.04 | 0.5 | 45 | 65 | 70 | |
| 61 | Z-Val-AspVSmethyl | >3.33 | >3.33 | >3.33 | >3.33 | >3.33 | 5 | 70 | 5 | |
| 68 | Z-Asp-Indanylglycine-Val-AspVSisopropyl | >3.33 | 0.2 | >3.33 | 1.5 | >3.33 | 30 | 60 | 50 | |
| 96 | Z-Tyr-Val-Ala-AspVSphenyl | 1.3 | >10 | >3.33 | >10 | >10 | | | | |
| 82 | Z-Tyr-Glu-Val-AspVSmethyl | 0.5 | 0.3 | >3 | >5 | 1.6 | | | | |
| | DEVD-fmk (positive control compound) | 0.4 | 0.6 | >3.33 | 1 | 0.5 | 85 (20 uM IC50) | | | |

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A compound of Formula I:

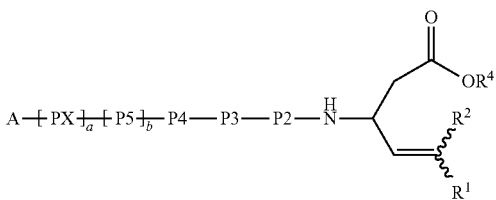

wherein
a is 0 or 1;
b is 0 or 1 provided that when b is 0, a is 0;
A is
1) H,
2) $C_1$-$C_6$ alkyl,
3) aryl,
4) heteroaryl,
5) heterocyclyl,
6) PhCH$_2$OC(O)—
7) $R^3$—OC(O)—,
or
8) $R^3$—S(O)$_2$—;
P2, P3, P4, and, when present, P5 and PX, are any (D) or (L) amino acid residue or non-natural amino acid residue;
the line "–" when located between P2, P3, P4, P5 or PX represents a peptide bond or a peptidomimetic bond;
the wavy line represents either cis or trans orientation of $R^1$ and $R^2$;
$R^1$ is
1) aryl,
2) heteroaryl,
3) heterocyclyl,
4) $C_2$-$C_6$ alkene-$R^{20}$,
5) $SO_2R^5$,
6) $SO_3R^5$,
7) $SOR^5$,
8) $SONHR^5$,
9) $SO_2NHR^5$,
10) CN,
11) $CO_2R^5$,
12) $COR^5$,
13) $PO_3R^5$,
14) $PO(OR^5)_2$, or
15) $PO(OR^5)$,
wherein the aryl, the heteroaryl, or the heterocyclyl are optionally substituted with one or more $R^{30}$;
$R^2$ is
1) $R^1$; or
2) H,
3) halogen,
4) haloalkyl,
5) $C_1$-$C_6$ alkyl,
6) $C_2$-$C_6$ alkene,
7) $C_3$-$C_7$ cycloalkyl,
8) $OR^9$;

9) $OCOR^6$,
10) $OCO_2R^6$,
11) $NR^7R^8$,
12) $NHSO_2R^6$,
13) $NHCOR^6$,
14) aryl,
15) heteroaryl, or
16) heterocyclyl;
$R^3$ is
1) $C_1$-$C_6$ alkyl,
2) aryl,
3) heteroaryl, or
4) heterocyclyl;
$R^4$ is
1) H, or
2) $C_1$-$C_6$ alkyl;
$R^5$ is
1) H,
2) $C_1$-$C_6$ alkyl,
3) $C_2$-$C_6$ alkene,
4) $C_3$-$C_7$ cycloalkyl,
5) aryl,
6) heteroaryl,
7) heterocyclyl, or
8) any optionally protected (D) or (L) amino acid residue or non-natural amino acid residue;
$R^6$ is
1) any (D) or (L) amino acid residue or non-natural amino acid residue,
2) $C_1$-$C_6$ alkyl,
3) $C_3$-$C_7$ cycloalkyl,
4) aryl,
5) heteroaryl, or
6) heterocyclyl,
in which the alkyl or the cycloalkyl are optionally substituted with one or more $R^{10}$ substituents; and in which the aryl, heteroaryl or heterocyclyl are optionally substituted with one or more $R^{20}$ substituents;
$R^7$ and $R^8$ are independently selected from:
1) H,
2) $C_1$-$C_6$ alkyl,
3) $C_3$-$C_7$ cycloalkyl,
4) haloalkyl,
5) aryl,
6) heteroaryl, or
7) heterocyclyl,
wherein the alkyl and the cycloalkyl are optionally substituted with one or more $R^{10}$ substituents, and the aryl, the heteroaryl and the heterocyclyl are optionally substituted with one or more $R^{20}$ substituents;
$R^9$ is
1) H,
2) $C_1$-$C_6$ alkyl,
3) $C_3$-$C_7$ cycloalkyl,
4) aryl,
5) heteroaryl, or
6) heterocyclyl,
in which the alkyl or the cycloalkyl are optionally substituted with one or more $R^{10}$ substituents; and in which the aryl, heteroaryl or heterocyclyl are optionally substituted with one or more $R^{20}$ substituents;
$R^{10}$ is independently selected from:
1) halogen,
2) $C_1$-$C_6$ alkyl,
3) $C_3$-$C_7$ cycloalkyl,
4) haloalkyl, 5) aryl,
6) heteroaryl,
7) heterocyclyl,
8) $OR^9$,
9) $S(O)_mR^9$,
10) $NR^7R^8$,
11) $COR^9$,
12) $C(O)OR^9$,
13) $OC(O)R^9$,
14) $SC(O)R^9$,
15) $CONR^7R^8$, or
16) $S(O)_2NR^7R^8$;
$R^{20}$ is independently selected from:
1) halogen,
2) $NO_2$,
3) CN,
4) $C_1$-$C_6$ alkyl,
5) haloalkyl,
6) $C_3$-$C_7$ cycloalkyl,
7) $OR^7$,
8) $NR^7R^8$,
9) $SR^7$,
10) aryl,
11) heteroaryl,
12) heterocyclyl,
13) $SO_2R^5$,
14) $SO_3R^5$,
15) $SOR^5$,
16) $SONHR^5$,
17) $SO_2NHR^5$,
18) $PO_3R^5$,
19) $PO(OR^5)_2$,
20) $PO(OR^5)$,
21) $COR^7$,
22) $CO_2R^7$,
23) $S(O)_mR^7$,
24) $CONR^7R^8$, or
25) $S(O)_2NR^7R^8$,
wherein the alkyl and the cycloalkyl are optionally substituted with one or more $R^6$ substituents; and wherein the aryl, the heteroaryl, or the heterocyclyl are optionally substituted with one or more $R^{30}$;
$R^{30}$ is
1) $NO_2$,
2) $C_2$-$C_6$ alkene-$R^{20}$,
3) $SO_2R^5$,
4) $SOR^5$,
5) $SONHR^5$,
6) $SO_2NHR^5$,
7) CN,
8) $CO_2R^5$,
9) $COR^5$,
10) $PO_3R^5$, 11) $PO(OR^5)_2$, or
12) $PO(OR^5)$;
or a pharmaceutically acceptable salt thereof.

2. The compound, according to claim 1, in which A is H.

3. The compound, according to claim 1, in which A is $PhCH_2OC(O)—$.

4. The compound according to claim 1, in which $R^4$ is H, $CH_3$, or $CH_3CH_2$.

5. The compound, according to claim 1, in which $R^4$ is H.

6. The compound, according to claim 1, in which a and b are both 0.

7. The compound, according to claim 1, in which a is 0 and b is 1.

8. The compound, according to claim 1, in which $R^1$ is in the trans or E configuration.

9. The compound, according to claim 1, $R^1$ is
1) $SO_2R^5$,
2) $SO_3R^5$; or
3) $SOR^5$,
wherein $R^5$ is $C_1$-$C_6$ alkyl, aryl, or heterocylyl.

10. The compound, according to claim 1, in which $R^2$ is
1) H,
2) halogen,
3) haloalkyl,
4) $C_1$-$C_6$ alkyl, or
5) $C_3$-$C_7$ cycloalkyl.

11. The compound, according to claim 10, in which $R^2$ is H or Cl.

12. The compound, according to claim 11, in which $R^2$ is Cl.

13. A compound of Formula IA

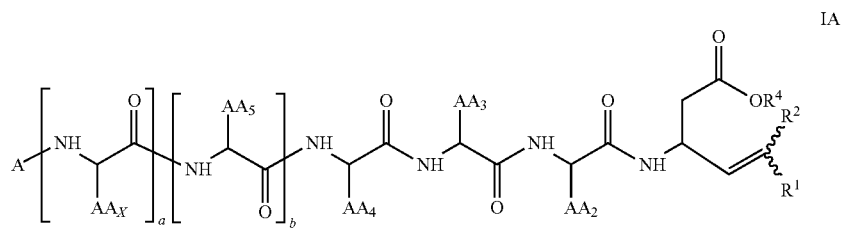

wherein
a is 0 or 1;
b is 0 or 1 provided that when b is 0, a is 0;
A is
1) H,
2) $C_1$-$C_6$ alkyl,
3) aryl,
4) heteroaryl,
5) heterocyclyl,
6) $R^3$—$OC(O)—$,
7) $R^3$—$S(O)_2—$, or
8) $PhCH_2OC(O)—$;
$AA_2$ is an amino acid side chain of Val, Leu, Pro, Met, Ala, Thr, His, Ser, Lys Trp, or Ile and wherein the carbon bearing $AA_2$ is of the (R) or (S) configuration;
$AA_3$ is an amino acid side chain of Trp, Tyr, Ala, Asp, Gln, Glu, Phe, Ser, Thr, Val, Gly, Leu, His, or Ile; or $AA_3$ is phenylglycine, indanylglycine, or Ala-(2'-quinolyl) and wherein the carbon bearing $AA_3$ is of the (R) or (S) configuration;
$AA_4$ is an amino acid side chain of Asp, Ile, Leu, Glu, Ala, Val, Tyr, Trp, Phe, or Pro and wherein the carbon bearing $AA_4$ is of the (R) or (S) configuration;

AA$_5$, when present, is an amino acid side chain of Val or Leu and wherein the carbon bearing AA$_5$ is of the (R) or (S) configuration;

AA$_x$, when present, is an amino acid side chain of any D or L amino acid residue and wherein the carbon bearing AA$_x$ is of the (R) or (S) configuration;

the wavy line represents either cis or trans orientation of R$^1$ and R$^2$;

R$^1$ is
1) aryl,
2) heteroaryl,
3) heterocyclyl,
4) C$_2$-C$_6$ alkene-R$^{20}$,
5) SO$_2$R$^5$,
6) SO$_3$R$^5$,
7) SOR$^5$,
8) SONHR$^5$,
9) SO$_2$NHR$^5$,
10) CN,
11) CO$_2$R$^5$,
12) COR$^5$,
13) PO$_3$R$^5$,
14) PO(OR$^5$)$_2$, or
15) PO(OR$^5$),
wherein the aryl, the heteroaryl, or the heterocyclyl are optionally substituted with one or more R$^{30}$;

R$^2$ is
1) R$^1$; or
2) H,
3) halogen,
4) haloalkyl,
5) C$_1$-C$_6$ alkyl,
6) C$_2$-C$_6$ alkene,
7) C$_3$-C$_7$ cycloalkyl,
8) OR$^9$;
9) OCOR$^6$,
10) OCO$_2$R$^6$,
11) NR$^7$R$^8$,
12) NHSO$_2$R$^6$,
13) NHCOR$^6$,
14) aryl,
15) heteroaryl, or
16) heterocyclyl;

R$^3$ is
1) C$_1$-C$_6$ alkyl,
2) aryl,
3) heteroaryl, or
4) heterocyclyl;

R$^4$ is
1) H, or
2) C$_1$-C$_6$ alkyl;

R$^5$ is
1) H,
2) C$_1$-C$_6$ alkyl,
3) C$_2$-C$_6$ alkene,
4) C$_3$-C$_7$ cycloalkyl,
5) aryl,
6) heteroaryl,
7) heterocyclyl, or
8) any optionally protected (D) or (L) amino acid residue;

R$^6$ is
1) any (D) or (L) amino acid residue,
2) C$_1$-C$_6$ alkyl,
3) C$_3$-C$_7$ cycloalkyl,
4) aryl,
5) heteroaryl, or
6) heterocyclyl,
in which the alkyl or the cycloalkyl are optionally substituted with one or more R$^{19}$ substituents; and in which the aryl, heteroaryl or heterocyclyl are optionally substituted with one or more R$^{20}$ substituents;

R$^7$ and R$^8$ are independently selected from:
1) H,
2) C$_1$-C$_6$ alkyl,
3) C$_3$-C$_7$ cycloalkyl,
4) haloalkyl,
5) aryl,
6) heteroaryl, or
7) heterocyclyl,
wherein the alkyl and the cycloalkyl are optionally substituted with one or more R$^{19}$ substituents, and the aryl, the heteroaryl and the heterocyclyl are optionally substituted with one or more R$^{20}$ substituents;

R$^9$ is
1) H,
2) C$_1$-C$_6$ alkyl,
3) C$_3$-C$_7$ cycloalkyl,
4) aryl,
5) heteroaryl, or
6) heterocyclyl,
in which the alkyl or the cycloalkyl are optionally substituted with one or more R$^{10}$ substituents; and in which the aryl, heteroaryl or heterocyclyl are optionally substituted with one or more R$^{20}$ substituents;

R$^{10}$ is independently selected from:
1) halogen,
2) C$_1$-C$_6$ alkyl,
3) C$_3$-C$_7$ cycloalkyl,
4) haloalkyl,
5) aryl,
6) heteroaryl,
7) heterocyclyl,
8) OR$^9$,
9) S(O)$_m$R$^9$,
10) NR$^7$R$^8$,
11) COR$^9$,
12) C(O)OR$^9$,
13) OC(O)R$^9$,
14) SC(O)R$^9$,
15) CONR$^7$R$^8$, or
16) S(O)$_2$NR$^7$R$^8$;

R$^{20}$ is independently selected from:
1) halogen,
2) NO$_2$,
3) CN,
4) C$_1$-C$_6$ alkyl,
5) haloalkyl,
6) C$_3$-C$_7$ cycloalkyl,
7) OR$^7$,
8) NR$^7$R$^8$,
9) SR$^7$,
10) aryl,
11) heteroaryl,
12) heterocyclyl,
13) SO$_2$R$^5$,
14) SO$_3$R$^5$,
15) SOR$^5$,
16) SONHR$^5$,
17) SO$_2$NHR$^5$,
18) PO$_3$R$^5$,
19) PO(OR$^5$)$_2$,
20) PO(OR$^5$), 21) COR$^7$,
22) CO$_2$R$^7$,
23) S(O)$_m$R$^7$,
24) CONR$^7$R$^8$, or
25) S(O)$_2$NR$^7$R$^8$,
   wherein the alkyl and the cycloalkyl are optionally substituted with one or more R$^6$ substituents; and wherein the aryl, the heteroaryl, or the heterocyclyl are optionally substituted with one or more R$^{30}$;
R$^{30}$ is
1) NO$_2$,
2) C$_2$-C$_6$ alkene-R$^{20}$,
3) SO$_2$R$^5$,
4) SOR$^5$,
5) SONHR$^5$,
6) SO$_2$NHR$^5$,
7) CN,
8) CO$_2$R$^5$,
9) COR$^5$,
10) PO$_3$R$^5$,
11) PO(OR$^5$)$_2$, or
12) PO(OR$^5$);
or a prodrug, or a pharmaceutically acceptable salt, or the compound is labeled with a detectable label or an affinity tag thereof.

14. The compound according to claim 13 which conforms to Formula IIA

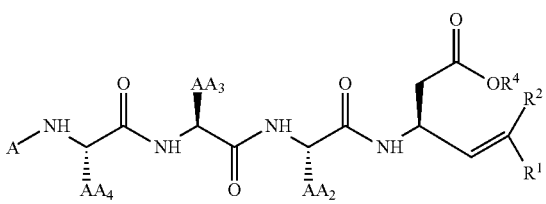

wherein
AA$_2$ is the amino acid side chain of Val, Leu, Pro, Met, Ala, Thr, His, Ser, or Lys;
AA$_3$ is the amino acid side chain of Trp, Tyr, Ala, Asp, Gln, Phe, Ser, Thr, Val, Gly, Leu, Glu; or AA$_3$ is phenylglycine, indanylglycine, or Ala-(2'-quinolyl);
AA$_4$ is the amino acid side chain of Asp;
and wherein A, R$^1$, R$^2$ and R$^4$ are as defined in claim 13.

15. The compound according to claim 13 which conforms to Formula IIA

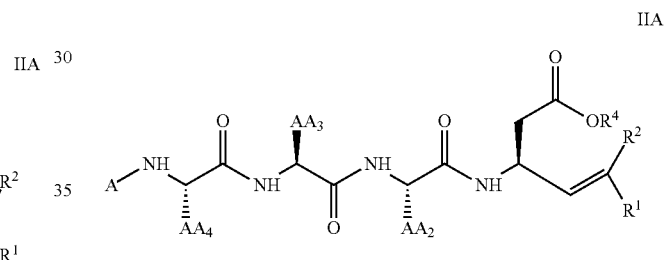

wherein
AA$_2$ is the amino acid side chain of Thr, His, Val, Trp, Ile, or Ala
AA$_3$ is the amino acid side chain of Glu or AA$_3$ is Ala-(2'-quinolyl);
AA$_4$ is the amino acid side chain of Ile, Leu, Glu, Asp, Ala, Pro or Val;
and wherein A, R$^1$, R$^2$ and R$^4$ are as defined in claim 13.

16. The compound, according to claim 13, includes compounds of Formula IIIA

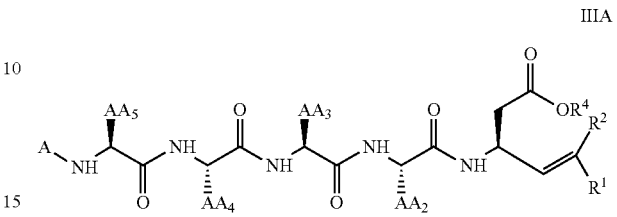

wherein
AA$_2$ is the amino acid side chain of Ile, Ala, Ser, Lys or Val;
AA$_3$ is the amino acid side chain of Val, Glu, Thr, or Gln;
AA$_4$ is the amino acid side chain of Val, Asp, or Leu;
AA$_5$ is the amino acid side chain of Pro, Val, or Leu;
and wherein A, R$^1$, R$^2$ and R$^4$ are as defined in claim 13.

17. The compound, according to claim 13, includes compounds of Formula IIA

IIA wherein
AA$_2$ is the amino acid side chain of Ile, Val, Ala, Thr, or His;
AA$_3$ is the amino acid side chain of Glu, Gln, Asp, Ala, Gly, Thr, Val, Trp; or AA$_3$ is phenylglycine or indanylglycine;
AA$_4$ is the amino acid side chain of Val, Tyr, Trp, Phe, or Asp;
and wherein A, R$^1$, R$^2$ and R$^4$ are as defined in claim 13.

18. An Intermediate compound selected from the group consisting of: compound #4, compound #12, compound #16, and compound #20.

19. A pharmaceutical composition comprising a compound according to claim 1 and one or more pharmaceutically acceptable carriers.

20. The compound, according to claim 1, in which the pharmaceutically acceptable salt is one that allows the compound to penetrate cells.

21. A method for treating, or reducing the risk of developing, a caspase-related disease in a subject in need thereof, comprising administering to said subject an effective amount of a compound according to claim 1, wherein the disease is selected from the group consisting of osteoarthritis, pancreatitis, rheumatoid arthritis, diabetes, inflammatory bowel disease, Crohn's disease, psoriasis, Graft vs host disease, organ transplant rejection, osteoporosis, sepsis, septic shock, Huntington's disease, cerebral ischemia, myocardial ischemia, multiple sclerosis, neurological damage due to stroke, ulcerative colitis, traumatic brain injury, Alzheimer's disease, Parkinson's disease, spinal cord injury, spinal muscular atrophy, retinal disorders, leukemias and related disorders, multiple myeloma-related diseases, metastatic melanomas, and Kaposi's sarcoma.

22. The compound of claim 1 wherein P4 is a natural or non-natural alpha amino acid.

23. pharmaceutical composition comprising a compound according to claim 13 and one or more pharmaceutically acceptable carriers.

24. A method for treating, or reducing the risk of developing, a caspase-related disease in a subject in need thereof, comprising administering to said subject an effective amount of a compound according to claim 1, wherein the disease is Alzheimer's disease.

25. A method for treating, or reducing the risk of developing, a caspase-related disease in a subject in need thereof, comprising administering to said subject an effective amount of a compound according to claim 13, wherein the disease is Alzheimer's disease.

* * * * *